United States Patent
Rabin et al.

(12) 
(10) Patent No.: US 6,344,321 B1
(45) Date of Patent: *Feb. 5, 2002

(54) NUCLEIC ACID LIGANDS WHICH BIND TO HEPATOCYTE GROWTH FACTOR/SCATTER FACTOR (HGF/SF) OR ITS RECEPTOR C-MET

(75) Inventors: Ross Rabin, Lafayette; Michael Lochrie, Louisville; Nebojsa Janjic; Larry Gold, both of Boulder, all of CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/364,539

(22) Filed: Jul. 29, 1999

Related U.S. Application Data

(63) Continuation-in-part of application No. 09/502,344, filed on Aug. 27, 1998, which is a continuation of application No. 08/469,609, filed on Jun. 6, 1995, now Pat. No. 5,843,653, which is a continuation of application No. 07/714,131, filed on Jun. 10, 1991, now Pat. No. 5,475,096, which is a continuation-in-part of application No. 07/536,428, filed on Jun. 10, 1990, now abandoned.

(51) Int. Cl.[7] .................... C07H 21/04; C07H 21/02; C12Q 1/68; C12P 19/34
(52) U.S. Cl. .................... 435/6; 435/91.1; 536/23.1; 536/24.3
(58) Field of Search .............. 435/6, 91.1; 536/23.1, 536/24.3

(56) References Cited

U.S. PATENT DOCUMENTS

| | | | |
|---|---|---|---|
| 5,723,323 A | 3/1998 | Kauffman et al. | 435/172.3 |
| 5,731,424 A * | 3/1998 | Toothman et al. | 536/23.1 |
| 5,734,034 A * | 3/1998 | Jayasena et al. | 536/23.1 |
| 5,837,834 A * | 11/1998 | Pagratis et al. | 536/23.1 |

FOREIGN PATENT DOCUMENTS

| | | |
|---|---|---|
| GB | 2 183 661 A | 6/1987 |
| WO | WO89/06694 | 7/1989 |
| WO | WO 91/19813 | 12/1991 |
| WO | WO92/14843 | 9/1992 |
| WO | WO94/06909 * | 3/1994 |

OTHER PUBLICATIONS

Joyce (1989) Gene 82:83.
Joyce & Inoue (1989) Nucleic Acids Research 17:711.
Ellington & Szostak (1990) Abstracts of papers presented at the 1990 meeting on RNA Processing, Cold Spring Harbor Laboratory, Cold Spring Harbor, NY, p. 84.
Kinzler & Vogelstein (1989) Nucleic Acids Research 17:3645.
Kramer et al. (1974) J. Mol. Biol. 89:719.
Levisohn & Spiegelman (1969) Proc. Natl. Acad. Sci. USA 63:805.
Levisohn & Spiegelman (1968) Proc. Natl. Acad. Sci. USA 60:866.
Oliphant et al. (1989) Mol. Cell. Biol. 9:2944.

(List continued on next page.)

Primary Examiner—Andrew Wang
Assistant Examiner—Karen A. Lacourciere
(74) Attorney, Agent, or Firm—Swanson & Bratschun, L.L.C.

(57) ABSTRACT

The invention provides nucleic acid ligands to hepatocyte growth factor/scatter factor (HGF) and its receptor c-met. The nucleic acid ligands of the instant invention are isolated using the SELEX method. SELEX is an acronym for Systematic Evolution of Ligands by EXponential enrichment. The nucleic acid ligands of the invention are useful as diagnostic and therapeutic agents for diseases in which elevated HGF and c-met activity are causative factors.

3 Claims, 23 Drawing Sheets

OTHER PUBLICATIONS

Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Thiesen & Bach (1990) Nucleic Acids Research 18:3203.
Szostak, "Structure and Activity of Ribozymes," in *Redesigning the Molecules of Life*, (S.A. Benner ed.) Springer–Verlag Berline Heidelberg, pp. 87–113 (1988).

* cited by examiner

N7 series

Synthetic 307 or 40N7 DNA template: SEQ ID NO:1 (N = 30) and
SEQ ID NO:15 (N = 40)

5'-TAATACGACTCACTATAGGGAUGACGAUGCGG-[N]$_{30,40}$-CAGACGACUCGCCCGA-3'

Starting random 30N7 or 40N7 RNA: SEQ ID NO:2 (N = 30) and
SEQ ID NO:308 (N = 40

5'-GGGAGGACGAUGCGG-[N]$_{30,40}$-CAGACGACUCGCCCGA-3'

N7 primers

5p7: 5'-TAATACGACTCACTATAGGGAUGACGAUGCGG-3'    SEQ ID NO:3

3p7: 5'-TCGGGCGAGTCGTCTG-3'    SEQ ID NO:4

N8 series

Synthetic 30N8 or 40N8 DNA template:

5'-TAATACGACTCACTATAGGGAGACAAGAATAAACGCTCAA-[N]$_{30,40}$-

TTCGACAGGAGGCTCACAACAGGC-3'    SEQ ID NO:5

Starting random 30N8 or 40N8 RNA:
5'-GGGAGAUAAGAAUAAACGCUCAA-[N]$_{30,40}$-UUCGACAGGAGGCUCACAACAGGC-3'
SEQ ID NO:6 (N = 30) and
SEQ ID NO:309 (N = 40)

N8 primers

5p8: 5'-TAATACGACTCACTATAGGGAGACAA-3'    SEQ ID NO:7

3p8: 5'-GCCTGTTGTGAGCCTCCTGTCGAA-3'    SEQ ID NO:8

Fig. 1

```
                        vv        v
N7 RNA    5'-gggaggacgaugcgg-[N]-cagacgacucgcccga-3'
             cccuccugcuacgcc-5'   gtctgcugagcgggcu-5'
             SEQ ID NO:9              SEQ ID NO:10

Cleaved RNA         5'-(g)g-[N]-ca-3'  SEQ ID NO:11
```

Fig. 2

APTAMER 8-102

SEQ ID NO:12

SEQ ID NO:13

SEQ ID NO:14

APTAMER 8-17
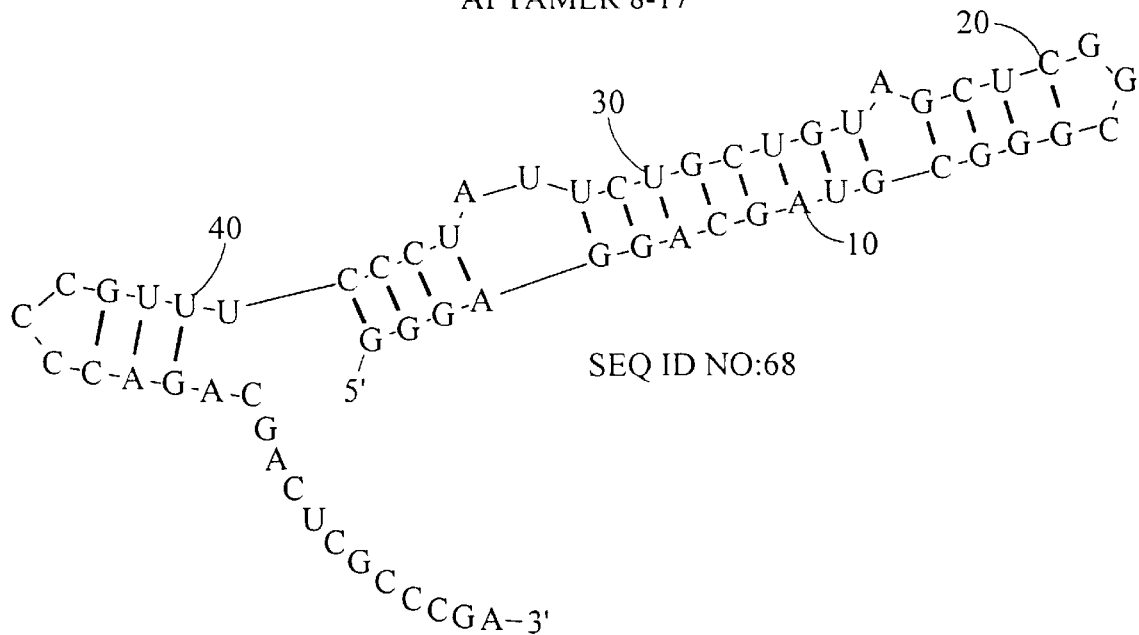
SEQ ID NO:68
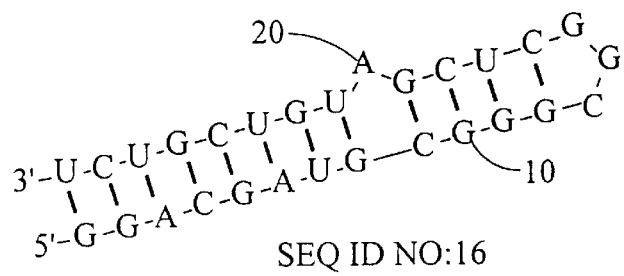
SEQ ID NO:16
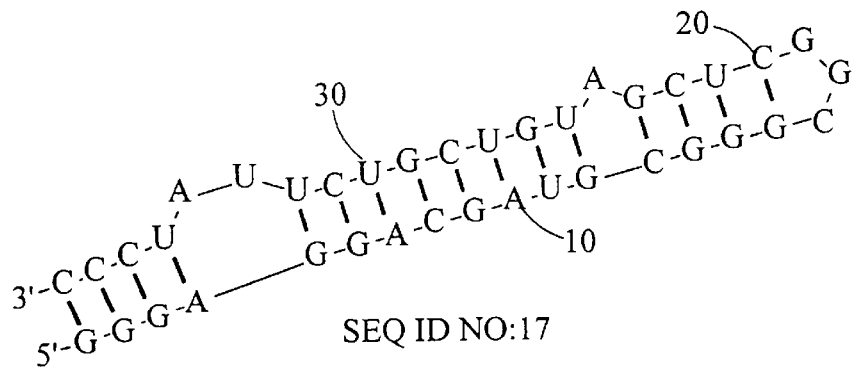
SEQ ID NO:17
FIG. 8A

NUCLEIC ACID LIGANDS WHICH BIND TO HEPATOCYTE GROWTH FACTOR/SCATTER FACTOR (HGF/SF) OR ITS RECEPTOR C-MET

CROSS REFERENCE TO RELATED APPLICATIONS

This application is a continuation-in-part of U.S. patent application Ser. No. 09/502,344, filed Aug. 27, 1998, entitled "Nucleic Acid Ligands," which is a continuation of U.S. patent application Ser. No. 08/469,609, filed Jun. 6, 1995, entitled "Method for Detecting a Target Molecule in a Sample Using a Nucleic Acid Ligand," now U.S. Pat. No. 5,843,653, which is a continuation of U.S. patent application Ser. No. 07/714,131, filed Jun. 10, 1991, entitled "Nucleic Acid Ligands," now U.S. Pat. No. 5,475,096, which is a continuation-in-part of U.S. patent application Ser. No. 07/536,428, filed Jun. 10, 1990, now abandoned.

FIELD OF THE INVENTION

This invention is directed towards obtaining nucleic acid ligands of hepatocyte growth factor/scatter factor (HGF) and its receptor c-met. The method used in the invention is called SELEX, which is an acronym for Systematic Evolution of Ligands by EXponential enrichment. The invention is also directed towards therapeutic and diagnostic reagents for diseases in which elevated HGF and c-met activity are causative factors.

BACKGROUND OF THE INVENTION

Hepatocyte growth factor/scatter factor (abbreviated herein as HGF) is a potent cytokine which, through interaction with its receptor c-met, stimulates proliferation, morphogenesis, and migration of a wide variety of cell types, predominantly epithelial. HGF and c-met are involved in several cellular processes involved in tumorigenesis, notably angiogenesis and motogenesis, the latter having been implicated in the migration of cells required for metastasis (reviewed in references Jiang and Hiscox 1997, Histol Histopathol. 12:537–55; Tamagnone and Comoglio 1997, Cytokine Growth Factor Rev. 8:129–42; Jiang, Hiscox et al. 1999, Crit Rev Oncol Hematol. 29:209–48). Interestingly, proteases that degrade the extracellular matrix also activate HGF, which in turn up-regulates urokinase type plasminogen activator (uPA) and its receptor, resulting in an activating loop feeding the invasive and migratory processes required for metastatic cancer.

HGF and the c-met receptor are expressed at abnormally high levels in a large variety of solid tumors. In addition to numerous demonstrations in vitro of the effects of HGF/c-met on the behavior of tumor cell lines, the levels of HGF and/or c-met have been measured in human tumor tissues (reviewed in reference Jiang 1999, Crit Rev Oncol Hematol. 29:209–48). High levels of HGF and/or c-met have been observed in liver, breast, pancreas, lung, kidney, bladder, ovary, brain, prostate, gallbladder and myeloma tumors in addition to many others.

For several of the cancer types listed above, the prognostic value of measuring HGF/c-met levels has been evaluated and found to be potentially useful for determining the progression and severity of disease. The correlative data are strongest in the case of breast cancer (Ghoussoub, Dillon et al. 1998, Cancer. 82:1513–20; Toi, Taniguchi et al. 1998, Clin Cancer Res. 4:659–64), and non-small cell lung cancer (Siegfried, Weissfeld et al. 1997, Cancer Res. 57:433–9; Siegfried, Weissfeld et al. 1998, Ann Thorac Surg. 66:1915–8).

Elevated levels of HGF and c-met have also been observed in non-oncological settings, such as hypertension (Morishita, Aoki et al. 1997, J Atheroscler Thromb. 4:12–9; Nakamura, Moriguchi et al. 1998, Biochem Biophys Res Commun. 242:238–43), arteriosclerosis (Nishimura, Ushiyama et al. 1997, J Hypertens. 15:1137–42; Morishita, Nakamura et al. 1998, J Atheroscler Thromb. 4:128–34), myocardial infarction (Sato, Yoshinouchi et al. 1998, J Cardiol. 32:77–82), and rheumatoid arthritis (Koch, Halloran et al. 1996, Arthritis Rheum. 39:1566–75), raising the possibility of additional therapeutic and diagnostic applications.

The role of HGF/c-met in metastasis has been elucidated in mice using cell lines transformed with HGF/c-met (reviewed in reference Jeffers, Rong et al. 1996, J Mol Med. 74:505–13). In another metastasis model, human breast carcinoma cells expressing HGF/c-met were injected in the mouse mammary fat pad, resulting in eventual lung metastases in addition to the primary tumor (Meiners, Brinkmann et al. 1998, Oncogene. 16:9–20). Also, transgenic mice which overexpress HGF become tumor-laden at many loci (Takayama, LaRochelle et al. 1997, Proc Natl Acad Sci U S A. 94:701–6).

None of the data mentioned above provide proof of a direct causative role of HGF/c-met in human cancer, although the accumulated weight of the correlative data are convincing. However, a causal connection was established between germ-line c-met mutations, which constitutively activate its tyrosine kinase domain, and the occurrence of human papillary renal carcinoma (Schmidt, Duh et al. 1997, Nat Genet. 16:68–73).

Recent work on the relationship between inhibition of angiogenesis and the suppression or reversion of tumor progression shows great promise in the treatment of cancer (Boehm, Folkman et al. 1997, Nature. 390:404–7). In this report, it was shown that the use of multiple angiogenesis inhibitors confers superior tumor suppression/regression compared to the effect of a single inhibitor. Angiogenesis is markedly stimulated by HGF, as well as vascular endothelial growth factor (VEGF) and basic fibroblast growth factor (bFGF) (Rosen, Lamszus et al. 1997, Ciba Found Symp. 212:215–26). HGF and VEGF were recently reported to have an additive or synergistic effect on mitogenesis of human umbilical vein endothelial cells (HUVECs) (Van Belle, Witzenbichler et al. 1998, Circulation. 97:381–90). Similar combined effects are likely to contribute to angiogenesis and metastasis.

Human HGF protein is expressed as a single peptide chain of 728 amino acids (reviewed in references Mizuno and Nakamura 1993, Exs. 65:1–29; Rubin, Bottaro et al. 1993, Biochim Biophys Acta. 1155:357–71; Jiang 1999, Crit Rev Oncol Hematol. 29:209–48). The amino-terminal 31 residue signal sequence of HGF is cleaved upon export, followed by proteolytic cleavage by uPA and/or other proteases. The mature protein is a heterodimer consisting of a 463 residue α-subunit and a 234 residue β-subunit, linked via a single disulfide bond. HGF is homologous to plasminogen: its α-subunit contains an N-terminal plasminogen-activator-peptide (PAP) followed by four kringle domains, and the β-subunit is a serine protease-like domain, inactive because it lacks critical catalytic amino acids. The recently solved crystal structure of an HGF fragment containing PAP and the first kringle domain indicate that this region is responsible for heparin binding and dimerization (Chirgadze, Hepple et al. 1999, Nat Struct Biol. 6:72–9), in addition to receptor interaction.

Human c-met protein is exported to the cell surface via a 23 amino acid signal sequence (reviewed in references Comoglio 1993, Exs. 65:131–65; Rubin 1993, Biochim Biophys Acta. 1155:357–71; Jiang 1999, Crit Rev Oncol Hematol. 29:209–48). The exported form of c-met is initially a pro-peptide which is proteolytically cleaved. The mature protein is a heterodimer consisting of an extracellular 50 kDa α-subunit bound by disulfide bonds to a 140 kDa β-subunit. In addition to its extracellular domain, the β-subunit has a presumed membrane-spanning sequence and a 435 amino acid intracellular domain containing a typical tyrosine kinase.

HGF is produced primarily by mesenchymal cells, while c-met is mainly expressed on cells of epithelial origin. HGF is very highly conserved at the amino acid level between species. This homology extends into the functional realm as observed in mitogenic stimulation of hepatocytes in culture by HGF across species, including human, rat, mouse, pig and dog. This indicates that human HGF can be used cross-specifically in a variety of assays.

Given the roles of HGF and c-met in disease, it would be desirable to have agents that bind to and inhibit the activity of these proteins. It would also be desirable to have agents that can quantitate the levels of HGF and c-met in individual in order to gather diagnostic and prognostic information.

The dogma for many years was that nucleic acids had primarily an informational role. Through a method known as Systematic Evolution of Ligands by EXponential enrichment, termed the SELEX process, it has become clear that nucleic acids have three dimensional structural diversity not unlike proteins. The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. Pat. No. 5,475,096 entitled "Nucleic Acid Ligands", U.S. Pat. No. 5,270,163 (see also WO 91/19813) entitled "Methods For Identifying Nucleic Acid Ligands" each of which is specifically incorporated by reference herein. Each of these applications, collectively referred to herein as the SELEX Patent Applications, describes a fundamentally novel method for making a nucleic acid ligand to any desired target molecule. The SELEX process provides a class of products which are referred to as nucleic acid ligands or aptamers, each having a unique sequence, and which has the property of binding specifically to a desired target compound or molecule. Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands,", now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8, 1998, entitled "Systematic Evolution of Ligands by Exponential Enrichment: Photoselection of Nucleic Acid Ligands and Solution SELEX" describe a SELEX based method for selecting nucleic acid ligands containing photoreactive groups capable of binding and/or photocrosslinking to and/or photoinactivating a target molecule. U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, which can be non-peptidic, termed Counter-SELEX. U.S. Pat. No. 5,567,588 entitled "Systematic Evolution of Ligands by EXponential Enrichment: Solution SELEX," describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,580,737, supra, describes highly specific nucleic acid ligands containing one or more nucleotides modified with 2'-amino ($2'-NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," now abandoned, describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by EXponential Enrichment: Chimeric SELEX,"

and U.S. Pat. No. 5,683,867 entitled "Systematic Evolution of Ligands by EXponential Enrichment: Blended SELEX," respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. patent application Ser. No. 08/434,465, filed May 4, 1995, entitled "Nucleic Acid Ligand Complexes". Each of the above described patent applications which describe modifications of the basic SELEX procedure are specifically incorporated by reference herein in their entirety.

It is an object of the present invention to obtain nucleic acid ligands to HGF and c-met using the SELEX process.

It is a further object of the invention to obtain nucleic acid ligands that act as inhibitors of HGF and c-met.

It is a further object of the invention to provide therapeutic and diagnostic agents for tumorigenic conditions in which HGF and c-met are implicated.

It is yet a further object of the invention to use nucleic acid ligands to HGF and c-met to diagnose and treat hypertension, arteriosclerosis, myocardial infarction, and rheumatoid arthritis.

It is an even further object of the invention to use nucleic acid ligands to HGF singly or in combination with other nucleic acid ligands that inhibit VEGF and/or bFGF, and/or possibly other angiogenesis factors.

SUMMARY OF THE INVENTION

Methods are provided for generating nucleic acid ligands to HGF and c-met. The methods use the SELEX process for ligand generation. The nucleic acid ligands provided by the invention are useful as therapeutic and diagnostic agents for a number of diseases.

BRIEF DESCRIPTION OF THE DRAWINGS

FIG. 1 illustrates the template and primer oligonucleotides used 2'-F-pyrimidine RNA SELEX experiments. The 5' fixed region of the template and primers contains a T7 promoter to facilitate transcription of RNA by T7 RNA polymerase.

FIG. 2 illustrates RNaseH cleavage primers used in hybridization truncate SELEX. Bases depicted in bold-type are 2'-O-methyl modified and bases underlined are deoxyribonucleosides. The random region is designated as "N". Upon treatment with RNaseH, the fixed regions are removed at the positions indicated by the carets. Note that the there are two possible cleavage sites at the 5-prime end of the fixed region, resulting in RNA which has one or two fixed G residues.

FIG. 3(A,B) illustrates binding of SELEX pools to HGF.

FIG. 4(A,B) illustrates two methods of evaluating HGF SELEX 3 30N7 pool binding to HGF.

FIG. 5(A,B) illustrates two methods of evaluating HGF SELEX 3 30N7 pool binding to HGF.

FIG. 6(A,B) illustrates inhibition of 10 ng/ml HGF stimulation of starved HUVECs by aptamers.

FIG. 7(A,B) illustrates truncates of aptamer 8–102.

FIG. 8(A,B) illustrates truncates of aptamer 8–17. FIG. 8A shows a predicted two-dimensional structures of full-length and truncated sequences.

FIG. 9(A,B) illustrates binding of HGF truncate SELEX pools.

FIG. 11(A,B) illustrates aptamer inhibition of 50 ng/ml HGF stimulation of 4MBr5 cells.

FIG. 14(A–C) illustrates aptamer-mediated inhibition of HUVEC mitogenesis.

FIG. 17(A–C) illustrates binding of SELEX pools to c-met.

FIG. 19(A,B) shows binding of c-met 40N7 cloned aptamers to c-met and KDR Ig fusion proteins.

DETAILED DESCRIPTION OF THE PREFERRED EMBODIMENTS

Figure 3A:
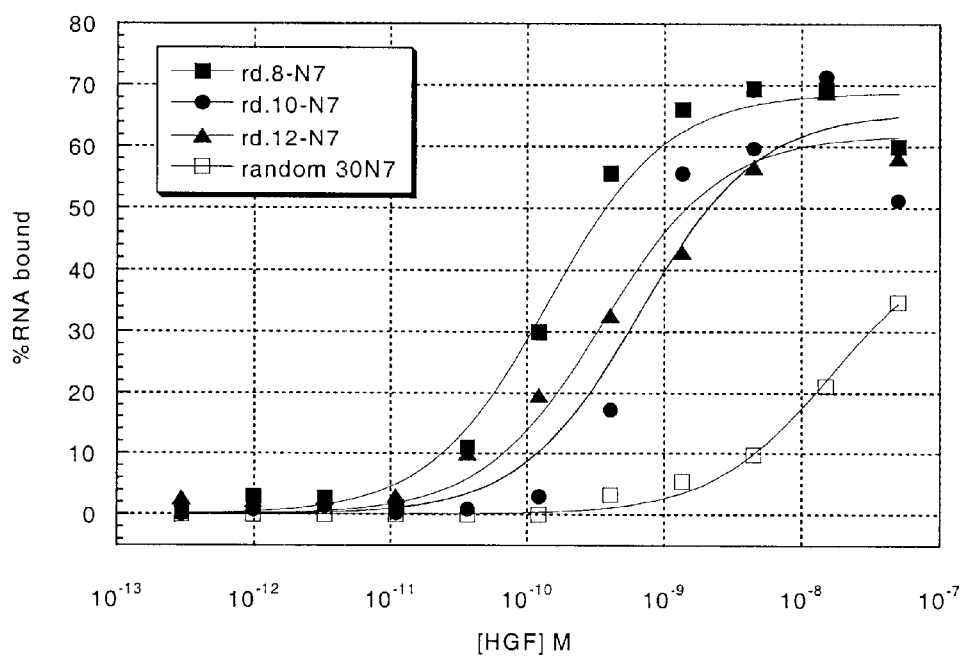
FIG. 3A shows HGF SELEX 1 30N7 pools.

The central method utilized herein for identifying nucleic acid ligands to HGF and c-met is called the SELEX process, an acronym for Systematic Evolution of Ligands by Exponential enrichment and involves (a) contacting the candidate mixture of nucleic acids with HGF or c-met, or expressed domains or peptides corresponding to HGF or c-met, (b) partitioning between members of said candidate mixture on the basis of affinity to HGF or c-met, and c) amplifying the selected molecules to yield a mixture of nucleic acids enriched for nucleic acid sequences with a relatively higher affinity for binding to HGF or c-met.

Definitions

Various terms are used herein to refer to aspects of the present invention. To aid in the clarification of the description of the components of this invention, the following definitions are provided:

As used herein, "nucleic acid ligand" is a non-naturally occurring nucleic acid having a desirable action on a target. Nucleic acid ligands are often referred to as "aptamers". The term aptamer is used interchangeably with nucleic acid ligand throughout this application. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. In the present invention, the targets are c-met and HGF or portions thereof. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to obtain nucleic acid ligands to HGF and c-met.

The SELEX methodology is described in the SELEX Patent Applications.

"SELEX target" or "target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the SELEX targets are HGF and c-met. In particular, the SELEX targets in this application include purified HGF and c-met, and fragments thereof, and short peptides or expressed protein domains comprising HGF or c-met. Also includes as targets are fusion proteins comprising portions of HGF or c-met and other proteins.

As used herein, "solid support" is defined as any surface to which molecules may be attached through either covalent or non-covalent bonds. This includes, but is not limited to, membranes, microtiter plates, magnetic beads, charged paper, nylon, Langmuir-Bodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces and grooved surfaces.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-met" refers to the receptor for HGF. This includes purified receptor, fragments of receptor, chemically synthesized fragments of receptor, derivatives or mutated versions of receptor, and fusion proteins comprising the receptor and another protein. "c-met" as used herein also includes the HGF receptor isolated from a species other than humans.

Note that throughout this application, various references are cited. Every reference cited herein is specifically incorporated in its entirety.

A. Preparing Nucleic Acid Ligands to HGF and c-met

In the preferred embodiment, the nucleic acid ligands of the present invention are derived from the SELEX methodology. The SELEX process is described in U.S. patent application Ser. No. 07/536,428, entitled Systematic Evolution of Ligands by Exponential Enrichment, now abandoned, U.S. Pat. No. 5,475,096 entitled Nucleic Acid Ligands, and U.S. Pat. No. 5,270,163 (see also WO 91/19813) entitled Methods for Identifying Nucleic Acid Ligands. These applications, each specifically incorporated herein by reference, are collectively called the SELEX Patent Applications.

The SELEX process provides a class of products which are nucleic acid molecules, each having a unique sequence, and each of which has the property of binding specifically to a desired target compound or molecule. Target molecules are preferably proteins, but can also include among others carbohydrates, peptidoglycans and a variety of small molecules. SELEX methodology can also be used to target biological structures, such as cell surfaces or viruses, through specific interaction with a molecule that is an integral part of that biological structure.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are chosen either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity for the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The basic SELEX method has been modified to achieve a number of specific objectives. For example, U.S. patent application Ser. No. 07/960,093, filed Oct. 14, 1992, now abandoned, and U.S. Pat. No. 5,707,796 both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands,", now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8, 1998, entitled "Systematic Evolution of Ligands by Exponential Enrichment: Photoselection of Nucleic Acid Ligands and Solution SELEX" all describe a SELEX based method for selecting nucleic acid ligands containing photoreactive groups capable of binding and/or photocrosslinking to and/or photoinactivating a target molecule. U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. Pat. No. 5,567,588 entitled "Systematic Evolution of Ligands by Exponential Enrichment: Solution SELEX," describes a SELEX-based method which achieves highly efficient partitioning between oligonucleotides having high and low affinity for a target molecule. U.S. Pat. No. 5,496,938 entitled "Nucleic Acid Ligands to HIV-RT and HIV-1 Rev," describes methods for obtaining improved nucleic acid ligands after SELEX has been performed. U.S. Pat. No. 5,705,337 entitled "Systematic Evolution of Ligands by Exponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,637,459, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," now abandoned, describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by Exponential Enrichment: Chimeric SELEX," and U.S. Pat. No. 5,683,867 entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules.

In U.S. Pat. No. 5,496,938 methods are described for obtaining improved nucleic acid ligands after the SELEX process has been performed. This patent, entitled Nucleic Acid Ligands to HIV-RT and HIV-1 Rev, is specifically incorporated herein by reference.

One potential problem encountered in the diagnostic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 8, 1993, now abandoned, and U.S. Pat. No. 5,660,985, both entitled "High Affinity Nucleic Acid Ligands Containing Modified Nucleotides", and the U.S. Patent Application entitled "Transcription-free SELEX", U.S. patent application Ser. No. 09/362,578 filed Jul. 28, 1999, each of which is specifically incorporated herein by reference. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodouracil; backbone modifications, phosphorothioate or alkyl phosphate modifications, methylations, unusual base-pairing combinations such as the isobases isocytidine and isoguanidine and the like. Modifications can also include 3' and 5' modifications such as capping. In preferred embodiments of the instant invention, the nucleic acid ligands are RNA molecules that are 2'-fluoro (2'-F) modified on the sugar moiety of pyrimidine residues.

The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand.

Other modifications are known to one of ordinary skill in the art. Such modifications may be made post-SELEX process (modification of previously identified unmodified ligands) or by incorporation into the SELEX process.

The nucleic acid ligands of the invention are prepared through the SELEX methodology that is outlined above and thoroughly enabled in the SELEX applications incorporated herein by reference in their entirety. The SELEX process can be performed using purified HGF or c-met, or fragments thereof as a target. Alternatively, full-length HGF or c-met, or discrete domains of HGF or c-met, can be produced in a suitable expression system. Alternatively, the SELEX process can be performed using as a target a synthetic peptide that includes sequences found in HGF or c-met. Determination of the precise number of amino acids needed for the optimal nucleic acid ligand is routine experimentation for skilled artisans.

In some embodiments, the nucleic acid ligands become covalently attached to their targets upon irradiation of the nucleic acid ligand with light having a selected wavelength. Methods for obtaining such nucleic acid ligands are detailed in U.S. patent application Ser. No. 08/123,935, filed Sep. 17, 1993, entitled "Photoselection of Nucleic Acid Ligands,", now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8, 1998, entitled "Systematic Evolution of Ligands by Exponential Enrichment: Photoselection of Nucleic Acid Ligands and Solution SELEX" each of which is specifically incorporated herein by reference in its entirety.

In preferred embodiments, the SELEX process is carried out using HGF or c-met attached to a solid support. A candidate mixture of single stranded RNA molecules is then contacted with the solid support. In especially preferred embodiments, the single stranded RNA molecules have a 2'-fluoro modification on C and U residues, rather than a 2'-OH group. After incubation for a predetermined time at a selected temperature, the solid support is washed to remove unbound candidate nucleic acid ligand. The nucleic acid ligands that bind to the HGF or c-met protein are then released into solution, then reverse transcribed by reverse transcriptase and amplified using the Polymerase Chain Reaction. The amplified candidate mixture is then used to begin the next round of the SELEX process.

In the above embodiments, the solid support can be a nitrocellulose filter. Nucleic acids in the candidate mixture that do not interact with the immobilized HGF or c-met can be removed from this nitrocellulose filter by application of a vacuum. In other embodiments, the HGF or c-met target is adsorbed on a dry nitrocellulose filter, and nucleic acids in the candidate mixture that do not bind to the HGF or c-met are removed by washing in buffer. In other embodiments, the solid support is a microtiter plate comprised of, for example, polystyrene.

In still other embodiments, the HGF or c-met protein is used as a target for Truncate SELEX, described in U.S. patent application Ser. No. 09/275,850, filed Mar. 24, 1999, entitled "The Truncation SELEX Method", incorporated herein by reference in its entirety.

In preferred embodiments, the nucleic acid ligands thus obtained are assayed for their ability to inhibit the HGF/c-met interaction. In one embodiment, this is performed by performing a cell migration assay. Certain cell types, such as A549 lung carcinoma cells, will show increased migration through a Matrigel-coated filter insert (Becton Dickinson) in the presence of HGF. Thus, the degree of inhibition of HGF activity in the presence of an HGF or c-met nucleic acid ligand can be assayed by determining the number of cells that have migrated through the filter in the presence of HGF.

B. Methods and Compositions For Using Nucleic Acid Ligands to Treat and Diagnose Disease Given that elevated levels of c-met and HGF are observed in hypertension, arteriosclerosis, myocardial infarction, and rheumatoid arthritis, nucleic acid ligands will serve as useful therapeutic and diagnostic agents for these diseases. In some embodiments, inhibitory nucleic acid ligands of HGF and c-met are administered, along with a pharmaceutically accepted excipient to an individual suffering from one of these diseases. Modifications of these nucleic acid ligands are made in some embodiments to impart increased stability upon the nucleic acid ligands in the presence of bodily fluids. Such modifications are described and enabled in the SELEX applications cited above.

In other embodiments, nucleic acid ligands to HGF and c-met are used to measure the levels of these proteins in an individual in order to obtain prognostic and diagnostic information. Elevated levels of c-met and HGF are associated with tumors in the liver, breast, pancreas, lung, kidney, bladder, ovary, brain, prostrate, and gallbladder. Elevated levels of HGF and c-met are also associated with myeloma.

In other embodiments, nucleic acid ligands that inhibit the HGF/c-met interaction are used to inhibit tumorigenesis, by inhibiting, for example, angiogenesis and motogenesis.

In one embodiment of the instant invention, a nucleic acid ligand to HGF is used in combination with nucleic acid ligands to VEGF (vascular endothelial growth factor) and/or bFGF (basic fibroblast growth factor) to inhibit tumor metastasis and angiogenesis. The use of multiple nucleic acid ligands is likely to have an additive or synergistic effect on tumor suppression. Nucleic acid ligands that inhibit VEGF are described in U.S. Pat. Nos. 5,849,479, 5,811,533, and U.S. patent application Ser. No. 09/156,824, filed Sep. 18, 1998, each of which is entitled "High Affinity Oligonucleotide Ligands to Vascular Endothelial Growth Factor", and each of which is specifically incorporated herein by reference in its entirety. Nucleic acid ligands to VEGF are also described in U.S. Pat. No. 5,859,228, U.S. patent application Ser. No. 08/870,930, filed Jun. 6, 1997, U.S. patent application Ser. No. 08/897,351, filed Jul. 21, 1997, and U.S. patent application Ser. No. 09/254,968, filed Mar. 16 1999, each of which is entitled "Vascular Endothelial Growth Factors (VEGF) Nucleic Acid Ligand Complexes, and each of which is specifically incorporated by reference in its entirety. Nucleic acid ligands to bFGF are described in U.S. Pat. No. 5,639,868 entitled "High Affinity RNA ligands for Basic Fibroblast Growth Factor", and U.S. patent application Ser. No. 08/442,423, filed May 16, 1995, entitled "High Affinity RNA Ligands for Basic Fibroblast Growth Factor", each of which is specifically incorporated herein by reference in its entirety.

EXAMPLES

The following examples are given by way of illustration only. They are not to be taken as limiting the scope of the invention in any way.

Materials and Methods

In the sections below entitled "Results: HGF" and "Results: c-met", the following materials and methods were used:

Proteins

The HGF protein and c-met-IgG$_1$-His$_6$ fusion protein, which were used in the SELEX process, and the KDR-IgG$_1$-His$_6$ proteins were purchased from R&D Systems, Inc. (Minneapolis, Minn.). The human c-met-IgG$_1$-His$_6$ fusion protein—described from the amino to the carboxyl terminus—consists of 932 amino acids from the extracellular domains of the α and β chains of c-met, a factor Xa cleavage site, 231 amino acids from human IgG$_1$ (Fc domain), and a (His)$_6$ tag. This protein is referred to in the text and figures as c-met. A similar fusion protein containing the vascular endothelial growth factor receptor KDR will be referred to as KDR.

Anti-HGF monoclonal antibody MAB294 was purchased from R&D Systems, Inc. Human IgG$_1$ was produced in-house by stable expression from Chinese hamster ovary cells.

SELEX Templates and Primers

Standard SELEX templates carrying 30 or 40 random nucleotides flanked by fixed regions of the N7 or N8 series and associated primers (FIG. 1) were used as described (Fitzwater and Polisky 1996, Methods Enzymol. 267:275–301). Truncate SELEX was done by the hybridization method described in U.S. patent application Ser. No. 09/275,850, filed Mar. 24 1999, entitled "The Truncation SELEX Method", incorporated herein by reference in its entirety, using RNaseH cleavage primers (FIG. 2).

SELEX Methods

Initial HGF SELEX experiments were done by two closely-related partitioning methods, both involving separating free from bound RNA on nitrocellulose filters. Conventional SELEX involves mixing target protein and RNA library in HBSMC buffer (hepes-buffered saline, 25 mM hepes, 137 mM NaCl, 5 mM KCl plus 1 mM CaCl$_2$, 1 mM MgCl$_2$, pH 7.4), followed by filtration on nitrocellulose under vacuum. Maintaining vacuum, the filter is washed in buffer, followed by vacuum release and RNA extraction. In spot filter SELEX, the protein is applied to a dry nitrocellulose 13 mm filter, allowed to adsorb for several minutes, then pre-incubated in Buffer S (HBSMC buffer plus 0.02% each of ficoll, polyvinylpyrrolidone, and human serum albumin) for 10 minutes at 37° C. to remove unbound protein. The wash buffer is removed, and then the RNA library is added in the same buffer, and incubated with the protein-bound filter. The filters are washed by repeated incubations in fresh buffer, followed by RNA extraction.

SELEX was initiated with between 1 and 5 nmoles of 2'-fluoro-pyrimidine RNA sequence libraries containing either a 30 or 40 nucleotide randomized region sequence (FIG. 1). The RNA libraries were transcribed from the corresponding synthetic DNA templates that were generated by Klenow extension (Sambrook, Fritsch et al. 1989, 3:B.12). The DNA templates were transcribed in 1 ml reactions, each containing 0.25 nM template, 0.58 µM T7 RNA polymerase, 1 mM each of ATP and GTP, 3 mM each of 2'-F-CTP and 2'-F-UTP, 40 mM Tris-HCl (pH 8.0), 12 mM MgCl$_2$, 1 mM spermidine, 5 mM DTT, 0.002% Triton X-100 and 4% polyethylene glycol (w/v) for at least 4 hours at 37° C. The full-length transcription products were purified by denaturing polyacrylamide gel electrophoresis. Radiolabeled RNA was obtained from transcription reactions as described above, but containing 0.2 nM ATP and 100 µCi of α-$^{32}$P-ATP. Alternatively, radiolabeled RNA was obtained by labeling the 5'-end of RNA with α-$^{32}$P-ATP (NEN-DuPont), catalyzed by T4 polynucleotide kinase (New England Biolabs). To prepare RNA containing 5'-OH groups for kinase reactions, transcription reactions included 5 mM guanosine.

For conventional filter SELEX, radiolabeled RNA pools were suspended in HBSMC buffer to which HGF protein was added, and incubated at 37° C for 30 minutes to 3 hours depending on the round. Binding reactions were then filtered under suction through 0.45 µm nitrocellulose filters (Millipore), pre-wet with binding buffer. The filters were immediately washed with at least 5 ml of HBSMC buffer. For each binding reaction, a protein-minus control reaction was done in parallel in order to determine the amount of background binding to the filters. The amount of RNA retained on the filters was quantified by Cherenkov counting, and compared with the amount input into the reactions. Filter-retained RNA was extracted with phenol and chloroform, and isolated by ethanol precipitation in the presence of 1–2 µg glycogen.

The isolated RNA was subsequently used as a template for avian myeloblastosis virus reverse transcriptase (AMV-RT, Life Sciences) to obtain cDNA. One hundred pmoles of the 3'-primer (FIG. 1) was added to the RNA and annealed by heating for 3 minutes at 70° C., followed by chilling on ice. The 50 µl reaction contained 5 U AMV-RT, 0.4 mM each of dNTPs, 50 mM Tris-HCl (pH 8.3), 60 mM NaCl, 6 mM Mg(OAc)$_2$, and 10 mM DTT, which was incubated for 45 minutes at 48° C. The cDNA was amplified by PCR with the 5'- and the 3'-primers (FIG. 1), and the resulting DNA template was transcribed to obtain RNA for the next round of SELEX.

To minimize selection of undesirable nitrocellulose-binding sequences, beginning in round three, we pre-soaked pools with nitrocellulose filters before incubating with the target protein. This treatment worked well to control background binding and helped ensure that each SELEX round had a positive signal/noise ratio. The progress of SELEX was monitored by nitrocellulose filter-binding analysis of the enriched pools (see below).

Truncate SELEX was performed by the hybridization method described in U.S. patent application Ser. No. 09/275, 850, filed Mar. 24 1999, entitled "The Truncation SELEX Method", incorporated herein by reference in its entirety. Briefly, 2'-F-RNA pools were body-labeled during transcription and cleaved by RNaseH using specific cleavage primers to remove the fixed sequences from the SELEX pool (FIG. 2). This RNA was then bound to target protein HGF and recovered following partitioning as in a conventional filter SELEX experiment. The recovered RNA was then biotinlyated at its 3-prime end and hybridized overnight under appropriate conditions with single-stranded full-length complementary strand DNA obtained from the starting SELEX pool, from which the RNA had been transcribed. The RNA/DNA complexes were then captured on streptavidin-coated magnetic beads and extensively washed to remove non-hybridized DNA. The bound DNA in the captured RNA/DNA complexes was then eluted by heat denaturation and amplified using conventional SELEX PCR primers. To complete the cycle, the resulting DNA was then used as a transcription template for generating RNA to be cleaved by RNaseH, and used in the next round of truncate SELEX.

For plate SELEX, a polystyrene well was pre-blocked in 400 µl of blocking agent for 60 minutes at 37° C. The blocking agent was removed and the desired amount of RNA in 100 µl binding buffer was added and incubated for 60 minutes at 37° C. White, polystyrene breakaway wells (catalog #950-2965) used for partitioning were from VWR (Denver, Colo.). The blocking agents, I-block and Superblock, were purchased from Tropix (Bedford, Mass.) and Pierce (Rockford, Ill.), respectively. The preadsorbtion was done to remove any nucleic acids which might bind to the well or the blocking agent. The random and round one libraries were not preadsorbed to plates to avoid loss of unique sequences. C-met protein was diluted in HBSMCK (50 mM HEPES, pH 7.4, 140 mM NaCl, 3 mM KCl, 1 mM $CaCl_2$, 1 mM $MgCl_2$), and was adsorbed to polystyrene wells by incubating 100 µl of diluted protein per well for 60 minutes at 37° C. The wells were each washed with three 400 µl aliquots of HIT buffer (HBSMCK, 0.1% I-block, 0.05% Tween 20), and then blocked in 400 µl of blocking agent for 60 minutes at 37° C. SELEX was initiated by incubating 100 µl of RNA in the protein-bound well for 60 minutes at 37° C. The RNA was removed and the wells were washed with 400 µl aliquots of HIT buffer. Increasing numbers of washes were used in later rounds. The wells were then washed twice with 400 µl water. RNA bound to c-met was eluted by adding 100 µl water and heating at 95° C. for 5 minutes and then cooled on ice, followed by reverse transcription.

Nitrocellulose Filter-binding

In binding reactions, RNA concentrations were kept as low as possible—between 1 and 20 pM—to ensure equilibrium in conditions of protein excess. Oligonucleotides were incubated for 15 minutes at 37° C. with varying amounts of the protein in 43 µl of the binding buffer. Thirty-two microliters of each binding mixture placed on pre-wet 0.45 µm nitrocellulose filters under suction. Each well was immediately washed with 0.5 ml binding buffer. The amount of radioactivity retained on the filters was quantitated by imaging. The radioactivity that bound to filters in the absence of protein was used for background correction. The percentage of input oligonucleotide retained on each filter spot was plotted against the corresponding log protein concentration. The nonlinear least square method was used to obtain the dissociation constant ($K_d$; reference Jellinek, Lynott et al. 1993, Proc. Natl. Acad. Sci. USA. 90:11227–31).

Competitor titration curves were generated essentially as a standard binding curve, except that the protein and RNA concentrations were kept constant, and the competitor concentration was varied. Competitors were also added at a fixed concentration in binding experiments to increase stringency for purposes of comparing pool binding affinities. In these experiments, the competitor concentration was chosen based on the results from the competitor titration curves.

Molecular Cloning and DNA Sequencing

To obtain individual sequences from the enriched pools, we cloned the PCR products from the final SELEX rounds using one of two blunt-end cloning kits, Perfectly Blunt (Novagen, Madison, Wis.), or PCR-Script (Stratagene, La Jolla, Calif.). Clones were sequenced with the ABI Prism Big Dye Terminator Cycle Sequencing kit (Perkin-Elmer Applied Biosystems, Foster City, Calif.). Sequences were obtained from an automated ABI sequencer, and text files were collated and analyzed by computer alignment and inspection.

Boundary Determinations

Five-prime and 3-prime boundaries of RNA aptamers were determined by the method of partial alkaline hydrolysis as described (Jellinek, Green et al. 1994, Biochemistry. 33:10450–6).

Cell Assays

Standard cell culture procedures were employed in the course of performing in vitro experiments to test aptamermediated inhibition of HGF activity. For cell migration assays, monolayers of A549 (lung carcinoma) cells were grown on the top-sides of Matrigel-coated filter inserts (Becton Dickinson, Franklin Lakes, N.J.) in 24-well plates. The cells adhere to the upper surface of the filter, which is placed in growth medium containing HGF. After two days, the cells are physically removed from the top surface of the filter. The filter is then removed from the insert and stained with crystal violet. Since all cells on the top of the filter are gone, the only cells that remain are those that are have migrated to the bottom of the filter. In the presence of HGF, significantly more cells are found on the bottom of the filter compared to controls without HGF.

Oligonucleotide Synthesis and Modification

RNA was routinely synthesized by standard cyanoethyl chemistry as modified (Green, Jellinek et al. 1995, Chem Biol. 2:683–95). Two-prime-fluoro-pyrimidine phosphoramidite monomers were obtained from JBL Scientific (San Luis Obispo, Calif.); 2'-OMe purine, 2'-OH purine, hexyl amine, and the dT polystyrene solid support were obtained from Glen Research (Sterling, Va.).

For addition of 40K-PEG, RNA oligomers were synthesized with an amino-linker at the 5'-position. This was subsequently reacted with NHS-ester 40K-PEG manufactured by Shearwater Polymers, Inc. (Huntsville, Ala.), and purified by HPLC on a reverse-phase preparative column.

2'-O-methyl Purine Substitution

Determination of which 2'-OH-purines can be substituted by 2'-O-methyl-purine was done as described (Green 1995, Chem Biol. 2:683–95). Briefly, a set of oligonucleotides was synthesized with a mixture of 2'-O-methyl amidites and 2'-OH amidites at defined purine positions. The set was designed so that each oligonucleotide contains a subset of partially-substituted purines, and the complete set encompasses all purines. Each aptamer was 5'-end labeled and subjected to limited alkaline hydrolysis followed by binding to HGF protein at two different concentrations, 50 and 100 pM. Following binding, protein-bound RNA was separated by standard nitrocellulose filtration. Bound RNA was recovered and analyzed by high-resolution gel electrophoresis. The fragmented alkaline-hydrolyzed aptamers which were not exposed to HGF were run to establish the cleavage patterns of the unselected aptamers. Hydrolysis occurs only at 2'-OH-purines. If a given position requires 2'-OH for optimal binding to HGF, it appears as a relatively darker band compared to the unselected aptamer at that position.

Results—HGF

Five HGF SELEX experiments were done in total. The first three were done by conventional filter SELEX, while the latter two were done by the hybridization truncate SELEX method described in U.S. patent application Ser. No. 09/275,850, filed Mar. 24 1999, entitled "The Truncation SELEX Method", incorporated herein by reference in its entirety. HGF SELEX 1 was done with 30N7 2'-F-RNA for thirteen rounds of conventional filter binding. HGF SELEX 2 was done with 30N8 2'-F-RNA for thirteen rounds of conventional filter binding. HGF SELEX 3 was done with 30N7 2'-F-RNA for seven rounds by spot filter binding, followed by eight rounds of filter binding. HGF SELEX 4 was done by hybridization filter SELEX for three rounds, starting with pool 8 from HGF SELEX 1. HGF SELEX 5 was done by hybridization filter SELEX for three rounds, starting with pool 11 from HGF SELEX 3. HBSMC buffer was used in conventional SELEX reactions, and in spot filter SELEX, blocking agents were added as described in Materials and Methods.

RNA Pool Binding With and Without Competitors Heparin and tRNA

Figure 3B:
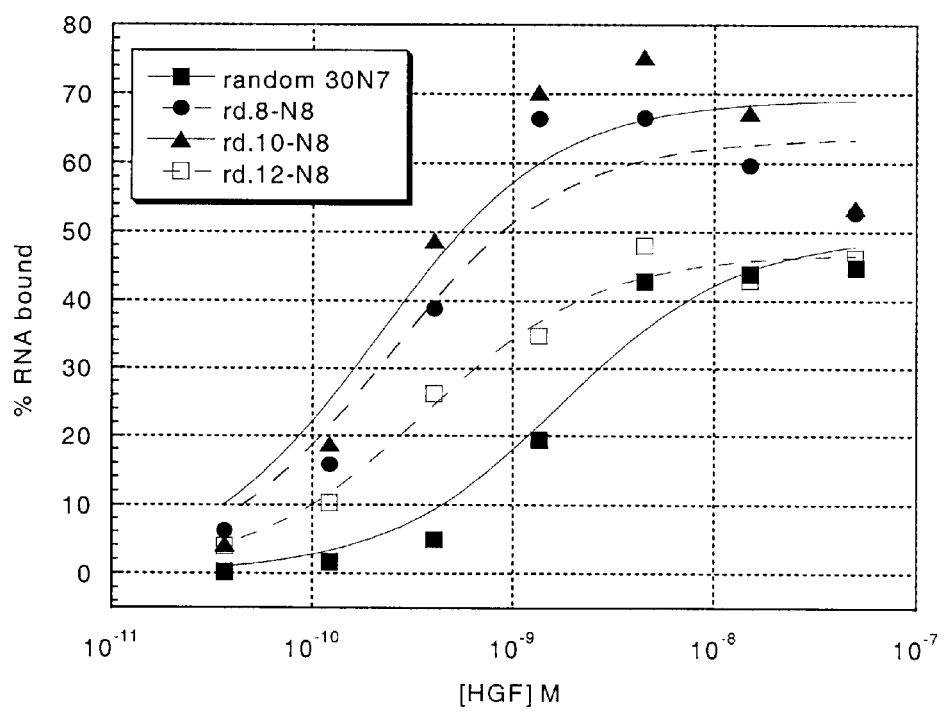
FIG. 3B shows HGF SELEX 2 30N8 pools.

To evaluate SELEX progress, binding curves with purified HGF protein were routinely done with evolved pools during the course of these experiments. Representative binding curves are shown for HGF SELEX experiments 1 and 2 (FIG. 3). These data were used to ascertain when a SELEX was complete in that further progress was not likely to occur by performing additional rounds. HGF SELEX 1 reached its maximal binding by round 8, with a binding affinity of approximately 0.1 nM (FIG. 3A; earlier rounds and round 9 were examined in other experiments). HGF SELEX 2 reached its maximal binding by round 10, with a binding affinity of approximately 0.1 nM (FIG. 3B). HGF SELEX 3 reached its maximal binding by round 11, after seven rounds of spot filter partitioning followed by four rounds of conventional filter SELEX (see FIG. 4B). A SELEX experiment which was deemed complete was characterized by cloning and sequencing (see below).

HGF, like other proteins which have large clusters of positively charged amino acids, exhibits a high degree of non-specific binding to polyanionic compounds. For example, random RNA pools bind to HGF with low nanomolar affinity, similar to the value reported for HGF binding to heparin, a polyanionic sulfated polysaccharide known to have an important biological role in HGF function (Zioncheck, Richardson et al. 1995, J Biol Chem. 270:16871–8). Competition binding to heparin as well as the non-specific competitor tRNA was done to provide an additional means of evaluating SELEX progress. We did this because the binding of random and evolved RNA pools to HGF occurs in a high-affinity range which makes it difficult to monitor progress. In other words, random RNA binds so well to HGF that the affinity enhancement of the evolved pools may not be adequately assessed in conventional binding experiments in the absence of competitor.

Figure 4A:
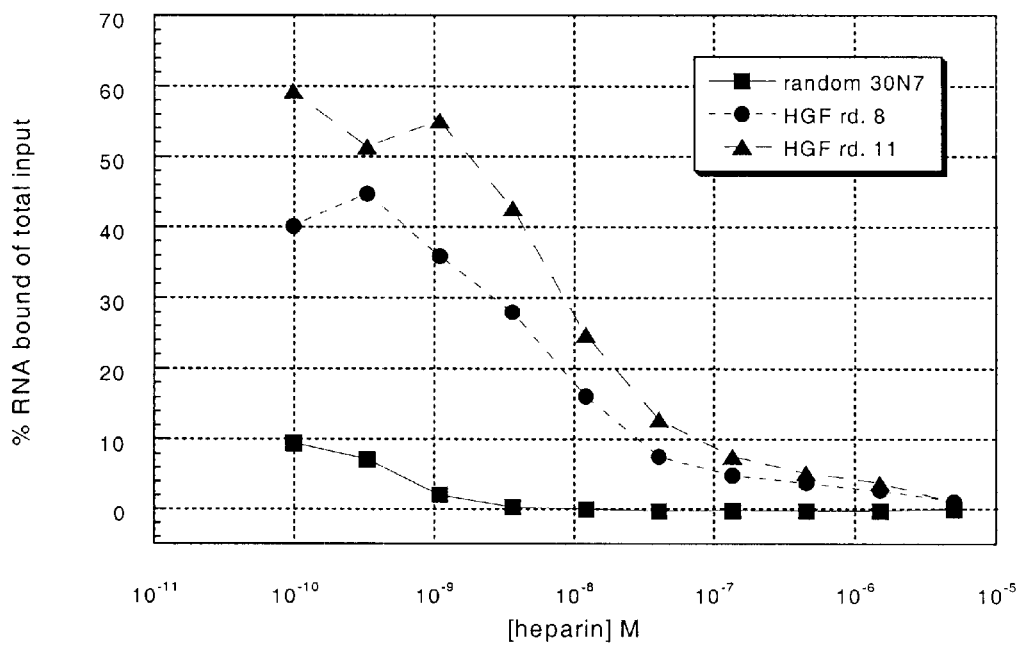
In FIG. 4A, heparin competes with RNA pools for binding to 2.7 nM HGF.
Figure 4B:
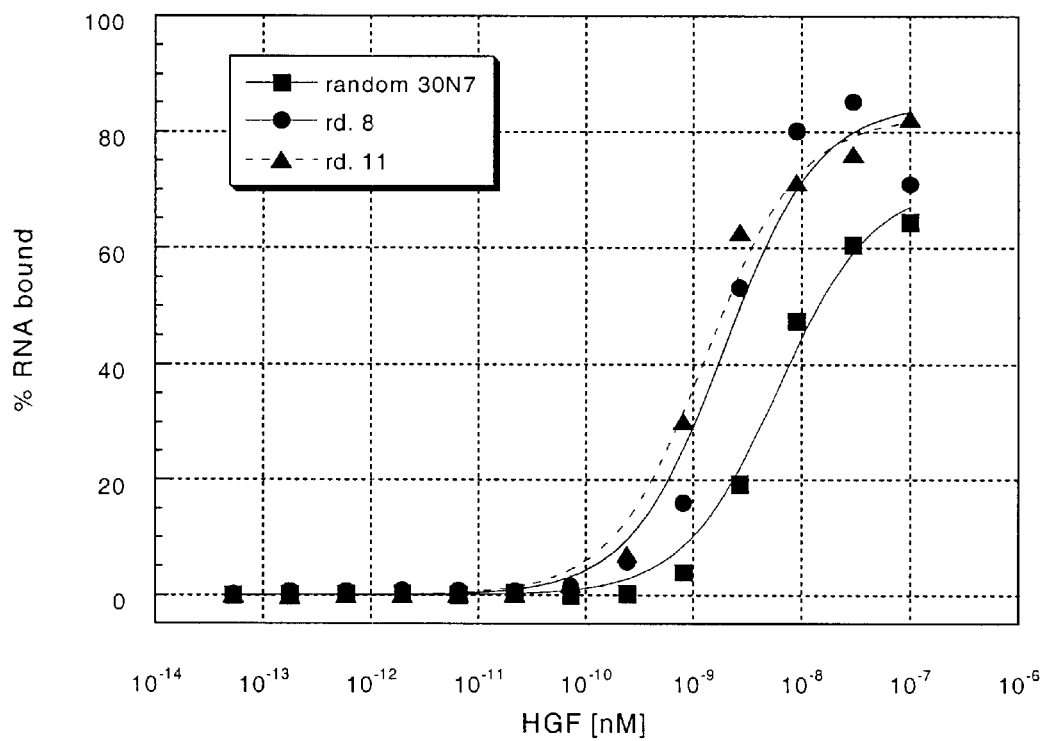
FIG. 4B illustrates conventional pool binding.

RNA pools from HGF SELEX 3 were subjected to competition with heparin (FIG. 4A). This experiment demonstrates that random RNA is considerably more sensitive to competition for binding to HGF than are the evolved pools. These data are compared to those obtained from a binding curve with the same three RNA pools (FIG. 4B). In the absence of heparin competition, binding of random RNA to HGF is nearly as good as that of the evolved pools, whereas the heparin competition reveals that the evolved pools are significantly different in composition from random RNA. In addition, while rounds 8 and 11 are indistinguishable in conventional binding curves, round 11 exhibits improved binding based on increased resistance to heparin competition. These data contributed to the choice of round 11 as the maximally binding pool from which we cloned and sequenced.

Figure 5A:
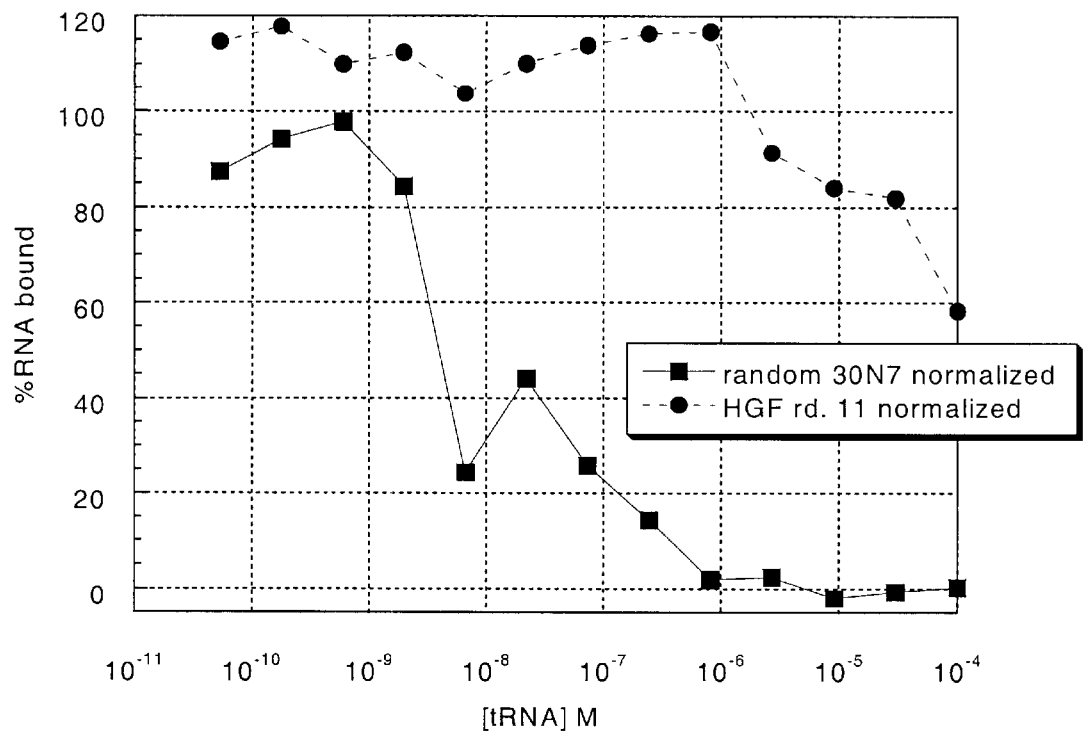
FIG. 5A shows that tRNA competes with RNA pools for binding to 2.7 nM HGF.
Figure 5B:
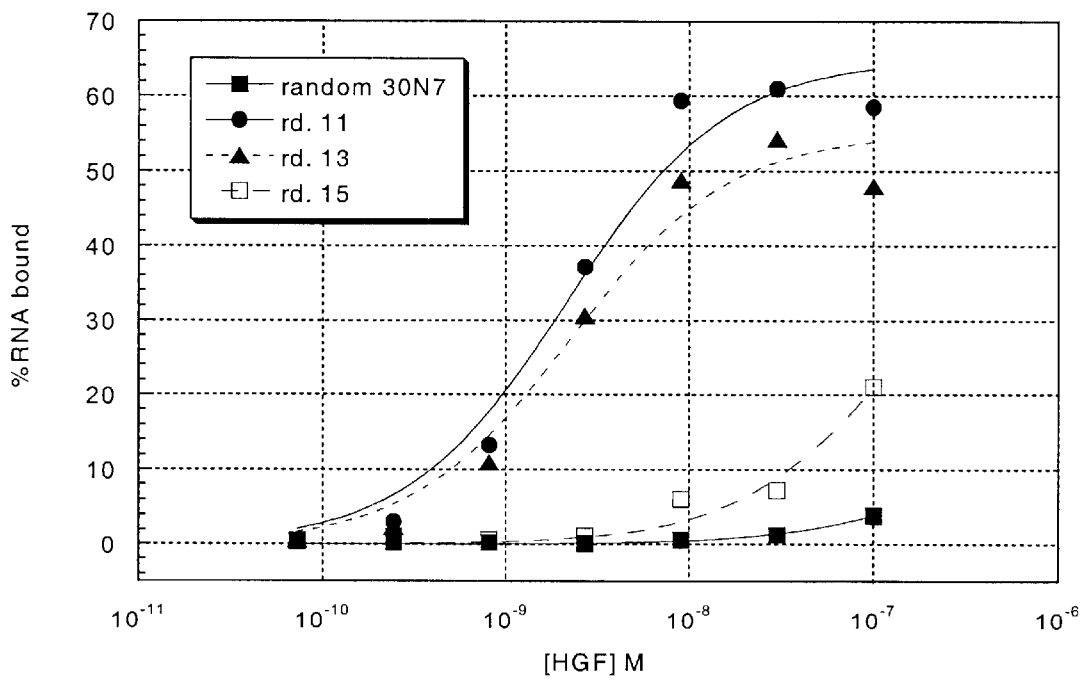
FIG. 5B shows conventional pool binding.

A similar, but more pronounced, effect was observed with tRNA as the competitor (FIG. 5A). These data indicate that the round 11 pool from HGF SELEX 3 are at least four orders of magnitude more resistant to competition for binding to HGF than is random RNA. From these curves, it was determined that 800 nM tRNA is the maximum concentration at which complete binding of evolved RNA persists. Therefore, binding curves were done at this tRNA concentration to compare the binding of different evolved pools (FIG. 5B). These curves were useful in determining that further SELEX rounds beyond round 11 did not improve binding.

Typical data from a similar set of binding competition experiments done for latter rounds of HGF SELEX 1 are summarized in Table 1.

Cloning and Sequence Analysis of HGF SELEXes 1, 2 and 3

Following determination of pool binding affinities for HGF, we subjected the optimal SELEX pools to cloning and sequencing in order to isolate and characterize individual aptamers. Data from 30N7 HGF SELEXes 1 and 3 are summarized in Table 2, including binding affinities for many of the aptamers. A similar data set was generated for 30N8 HGF SELEX 2 (Table 3). Sequences from HGF SELEX 1, 2 and 3 are designated 8-seq. number, 10-seq. number, and 11-seq. number, respectively, referring to the total number of SELEX rounds each cloned pool was subjected to. Sequences were analyzed and organized into groups with significant homology. Motifs were analyzed and predicted structures were drawn in order to analyze key features responsible for binding to HGF.

Inhibition of HGF-mediated Stimulation of Cell Proliferation

HGF, while not a potent mitogen, does stimulate moderate proliferation of many cell lines, which can be measured by incorporation of $^3$H-thymidine. We assayed the inhibitory activity of HGF aptamers by measuring their effect on proliferation of human umbilical vein endothelial cells (HUVECs), or monkey bronchial epithelial (4MBr-5) cells. Based on the binding data and sequence family analysis, fourteen aptamers were chosen for analysis in vitro because they bind to HGF with high affinity and are representative of different sequence families. The sequences are shown in Table 4 aligned by a rough consensus which contains bases in common to several families. All sequences are 30N7 except 10–2 which is 30N8.

Figure 6A:
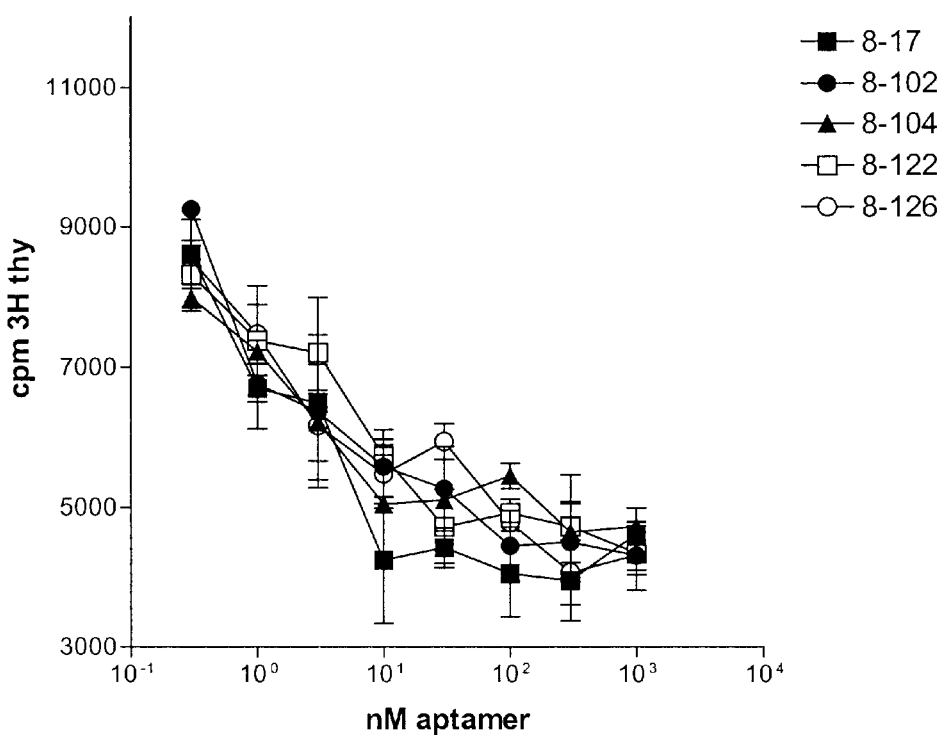
FIG. 6A shows a 1st set of aptamers.
Figure 6B:
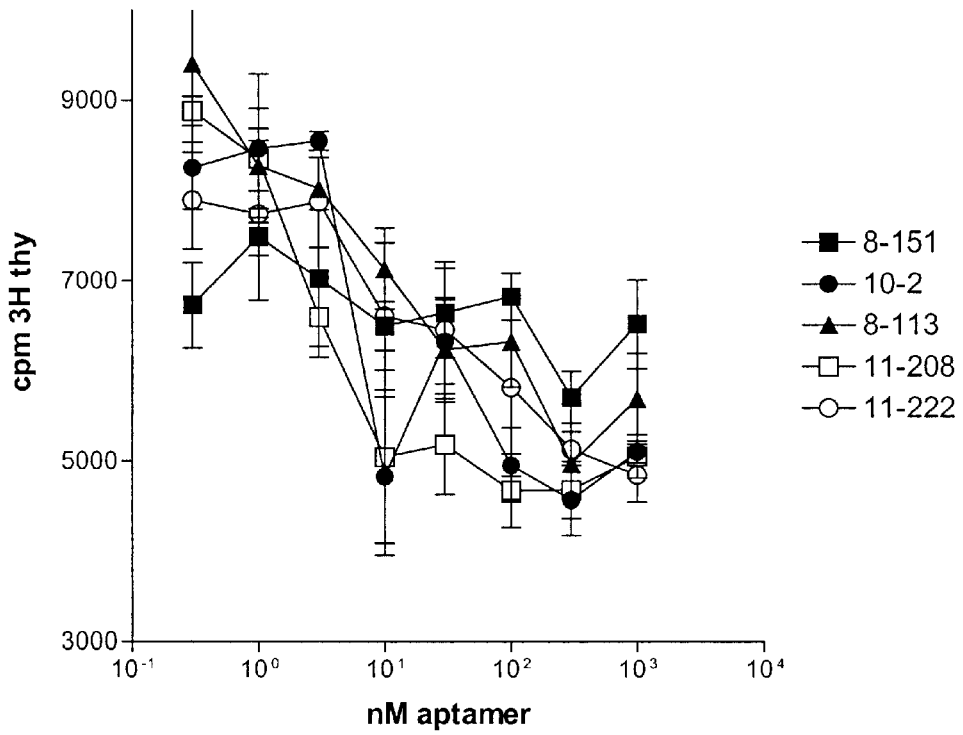
FIG. 6B illustrates a 2nd set of aptamers.

HGF stimulates proliferation of HUVECs by about two-to-three-fold (data not shown). The initial experiment indicated that aptamers 8-17, 8-102, 8-104, 8-122, 8-126, 10-2 and 11-208 were effective inhibitors of HGF-induced HUVEC proliferation with $K_i$ values in the low nanomolar range (FIG. 6). Aptamers 8-113 and 11-222 were less effective and 8-151 exhibited little or no concentrationdependent inhibition. The latter observation is consistent with the fact that aptamer 8-151 does not bind HGF with high affinity and actually binds worse than the random pool.

Several approaches were taken to reduce the length of aptamers which retained significant inhibition of HGF: 1) boundary determinations by biochemical separation of partially hydrolyzed aptamers; 2) sequence motif analysis and educated guessing; and 3) truncate SELEX.

Boundaries and Truncation

Boundary determinations were done for a subset of aptamers that demonstrated in vitro inhibition of HGF activity. Using a standard alkaline hydrolysis procedure with 5'-end-labeled RNA, we examined the 3'-boundaries of 8-17, 8-102, 8-104, 8-126, 10-1, and 10-2. Additionally, 3'-end-labeled RNA was used for 5'-boundary experiments with 8-17 and 8-102. These experiments were mostly uninformative, probably because the high degree of non-specific binding of RNA fragments, regardless of size, obscured the binding of truncated high-affinity aptamers to HGF. Non-specific binding of virtually all fragments gave no boundary information, and reducing the protein concentration did not help. Instead, we tried to use polyanionic competitors tRNA and heparin to eliminate nonspecific binding to reveal the actual boundaries. The competitors reduced non-specific binding, and HGF was predominantly bound only by full-length aptamers, revealing no boundary information beyond the possibility that full-length aptamers are strongly preferred.

Figure 7A:
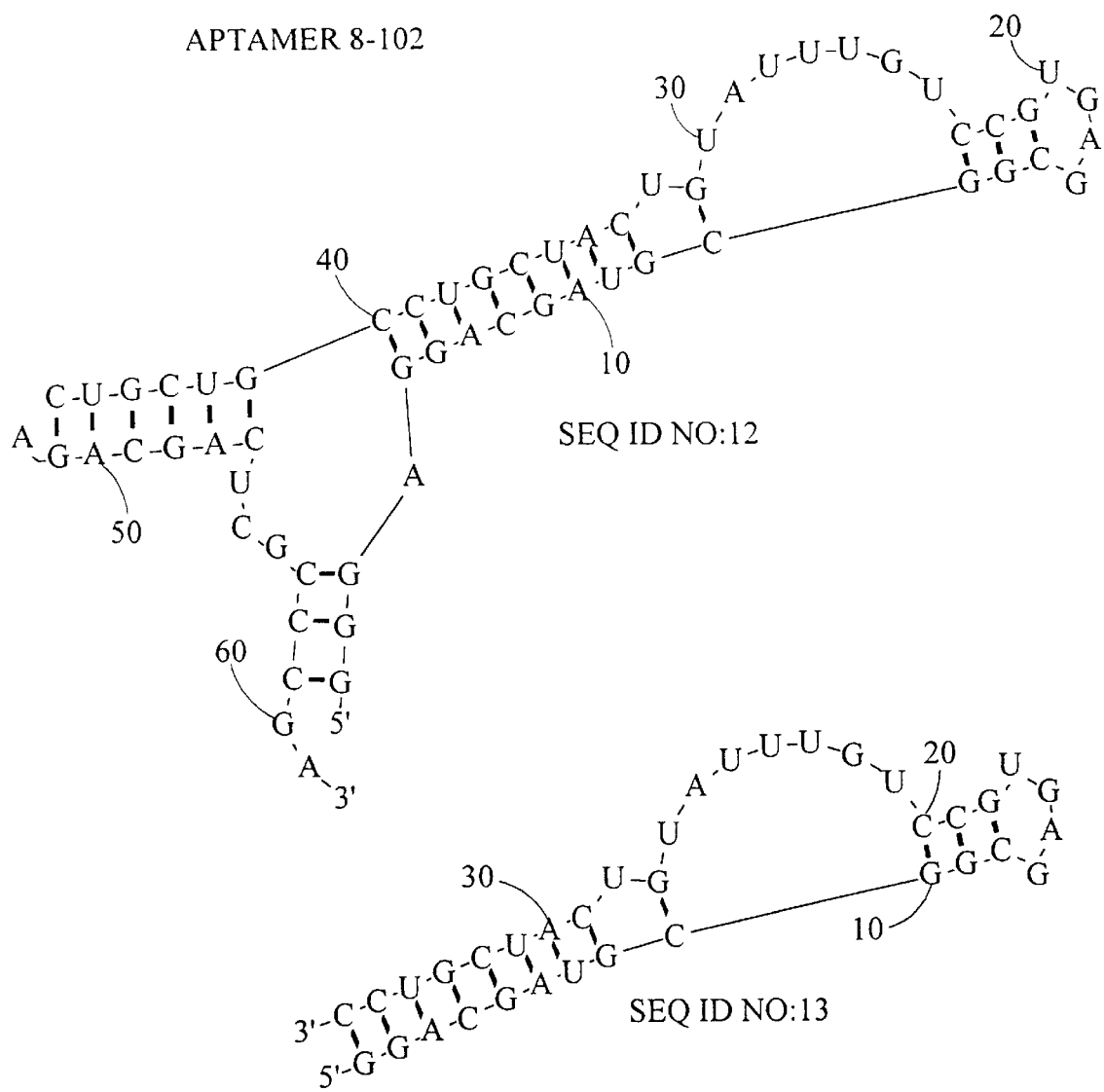
FIG. 7A shows predicted two-dimensional structures of full-length and truncated sequences.

The sole exception was aptamer 8-102 which had a plausible 3'-boundary between two possible endpoints which made sense with respect to computer-predicted structures (FIG. 7A). Based on the boundary data and structural data, two truncates of 8-102 were synthesized and analyzed for binding to HGF. The sequence of the full-length aptamer and the two truncates are shown, with fixed regions underlined:

gggaggacgaugcggcgagugccuguuuaugucaucguccgucgu
 cagacgacucgcccga 8-102                    SEQ ID NO:12 ggacgaugcggcgagugccuguuuaugucaucgucc (36mer) SEQ ID NO:13 gacgaugcggcgagugccuguuuauguc (28mer)       SEQ ID NO:14

Figure 7B:
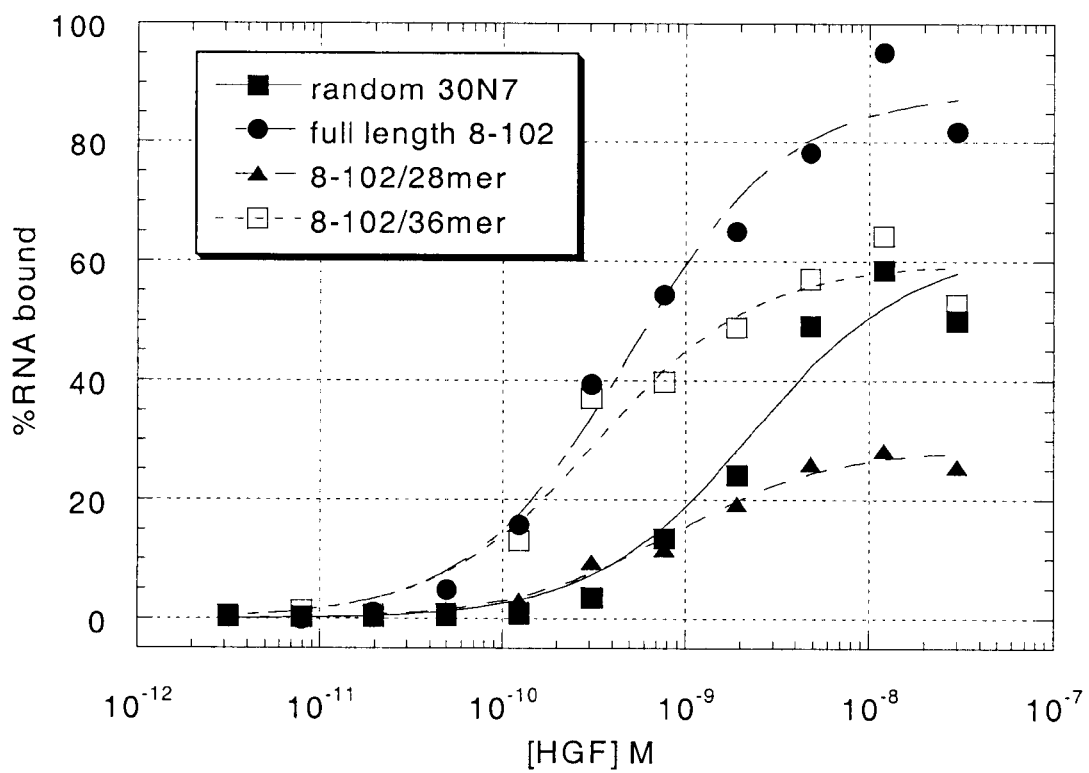
FIG. 7B shows binding of full-length and truncated aptamers to HGF.

In binding to HGF, the 36mer bound almost as well as the full-length aptamer, while the 28mer bound no better than random 30N7 (FIG. 7B), suggesting that the boundary data were correct.

Truncation By Sequence Structure Prediction

Figure 8B:
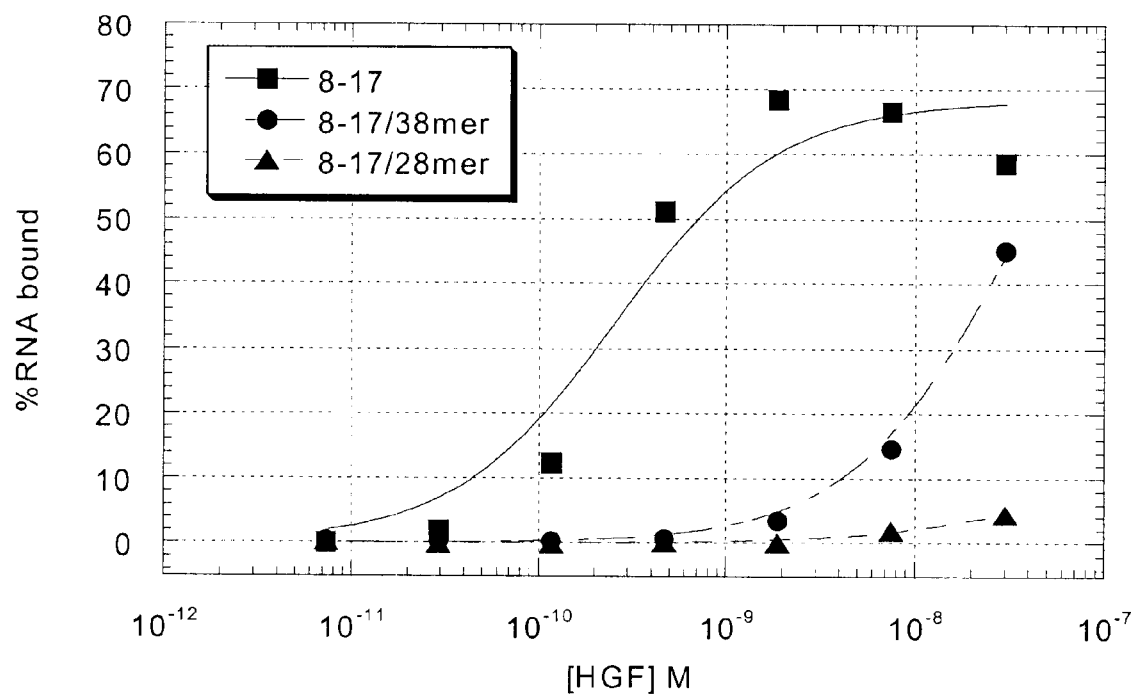
FIG. 8B shows binding of full-length and truncated aptamers to HGF.

Several attempts were made to base truncation on motif analysis and predicted structures, but these did not succeed in producing truncates which retained binding to HGF. For example, aptamer 8-17 folded into a reasonable predicted structure which suggested two obvious points of truncation from its 3-prime terminus, into a 38mer or 28mer (FIG. 8A). However, binding analysis revealed that neither of these truncates retained significant binding to HGF (FIG. 8B). These data suggest either that the predicted structure is incorrect or that some of the 3-prime region past base 38 is critical for high-affinity binding of aptamer 8-17 to HGF. These two hypotheses are not mutually exclusive. Nevertheless, we did not succeed in obtaining a useful truncate of 8-17 by boundary and structural prediction.

Truncate SELEX

In order to generate additional short aptamers, we subjected advanced rounds of the earlier SELEXes to additional rounds of truncate SELEX, using the Truncation SELEX method described in U.S. patent application Ser. No. 09/275, 850, filed Mar. 24, 1999, entitled "The Truncation SELEX Method", incorporated herein by reference in its entirety. Binding of RNaseH cleaved pools was examined to determine which were the appropriate rounds to use to initiate truncate SELEX (data not shown). None of the RNaseH-cleaved evolved pools was clearly superior to another in binding to HGF, therefore, the pools which had been previously cloned were chosen to use in truncate SELEX. The encouraging result from this experiment was that after RNaseH treatment, the evolved pools bound better to HGF than did random RNA, suggesting that even in the absence of the fixed regions, significant binding affinity was retained. This observation was sufficient evidence to suggest that truncate SELEX could enrich for sequences which bound to HGF in the absence of fixed regions.

Three rounds of hybridization truncate SELEX were done in parallel, using as starting pools HGF SELEX 1 round 8 and HGF SELEX 3 round 11. The truncate SELEX rounds were done at equi-molar RNA and protein, starting at 1 nM and decreasing to 0.5 and 0.1 nM. Signal-to-noise ratios were very high during selection. Subsequent manipulations were satisfactory even though the amount or recovered RNA was sub-picomolar.

Figure 9A:
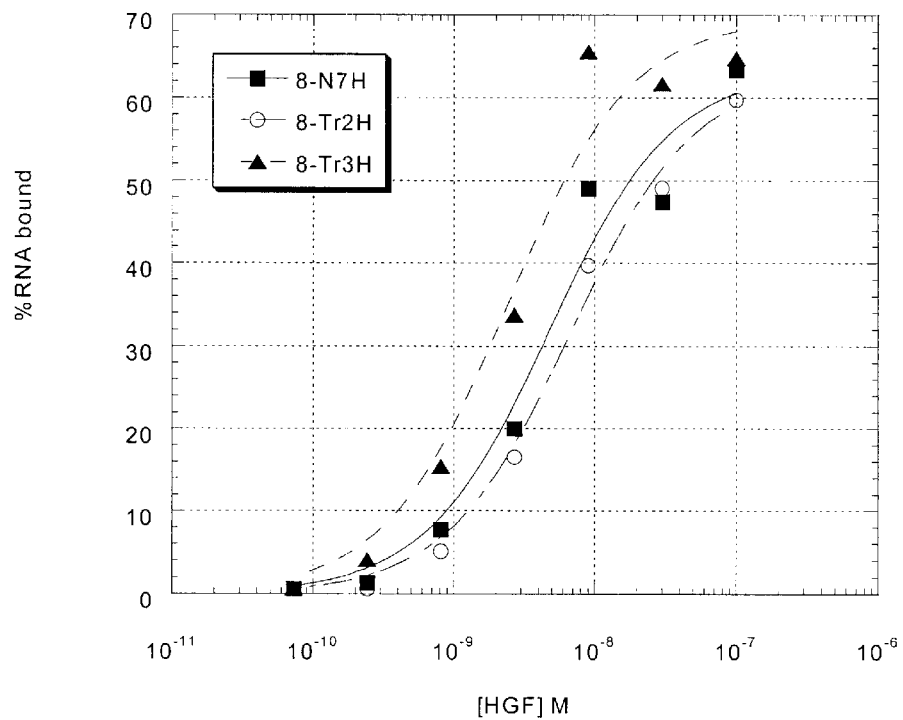
FIG. 9A shows the HGF SELEX 4 30N7 series.
Figure 9B:
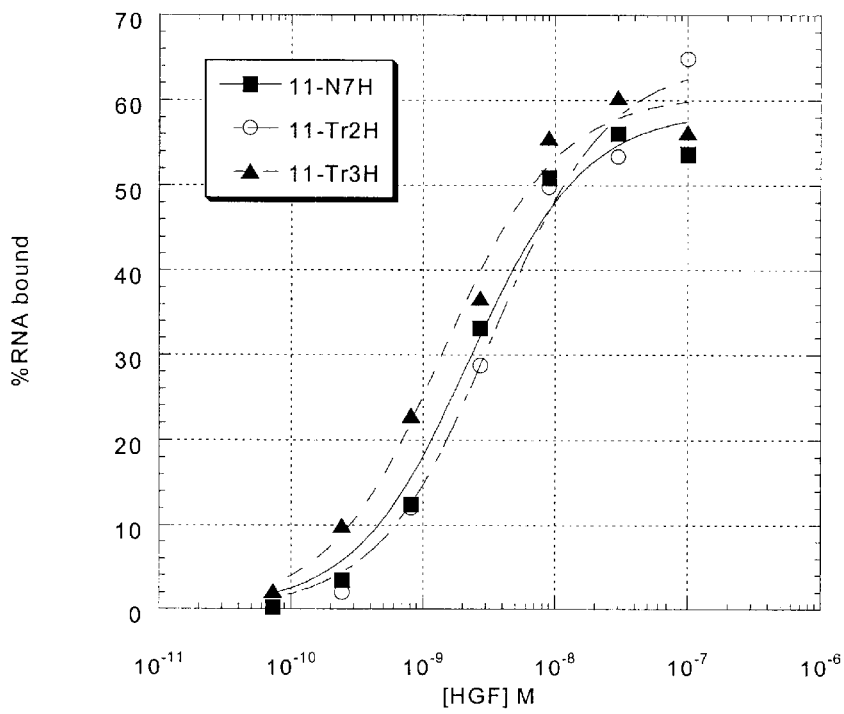
FIG. 9B shows the HGF SELEX 5 30N7 series.

To evaluate the progress of the SELEX, binding affinities of truncate rounds two and three were determined compared to those of the RNaseH-cleaved starting pools (FIG. 9). For both SELEXes, the third round pools bound with improved affinity for HGF compared with the earlier rounds. Interestingly, the second rounds did not bind HGF better than the staring material. The dissociation constants for the third round truncate SELEX pools are 1–2 nM, representing a 2–3 fold improvement. While the magnitude of this improvement is not large, it is probably significant since HGF as a target did not easily yield affinity enrichment, probably because of its intrinsically high affinity for RNA.

The two pools were cloned and sequenced, and binding affinities were determined (Table 5). The truncated aptamer with the best binding affinity, Tr51, is among several sequences which are novel, that is, they were not found in the clones sequenced from the full-length SELEX pools. The emergence of novel sequences suggests that the truncate SELEX succeeded in amplifying aptamers which were relatively rare in the full-length pools. Aptamer Tr51 appeared more frequently than any other sequence, consistent with the observation that it has better binding affinity than any other truncate. Other sequences which appeared multiple times also tend to be those with binding affinities near or better than the pool $K_d$ of 1–2 nM.

HGF Inhibition By the 36mer Aptamer Modified With 40K-PEG

Figure 10:
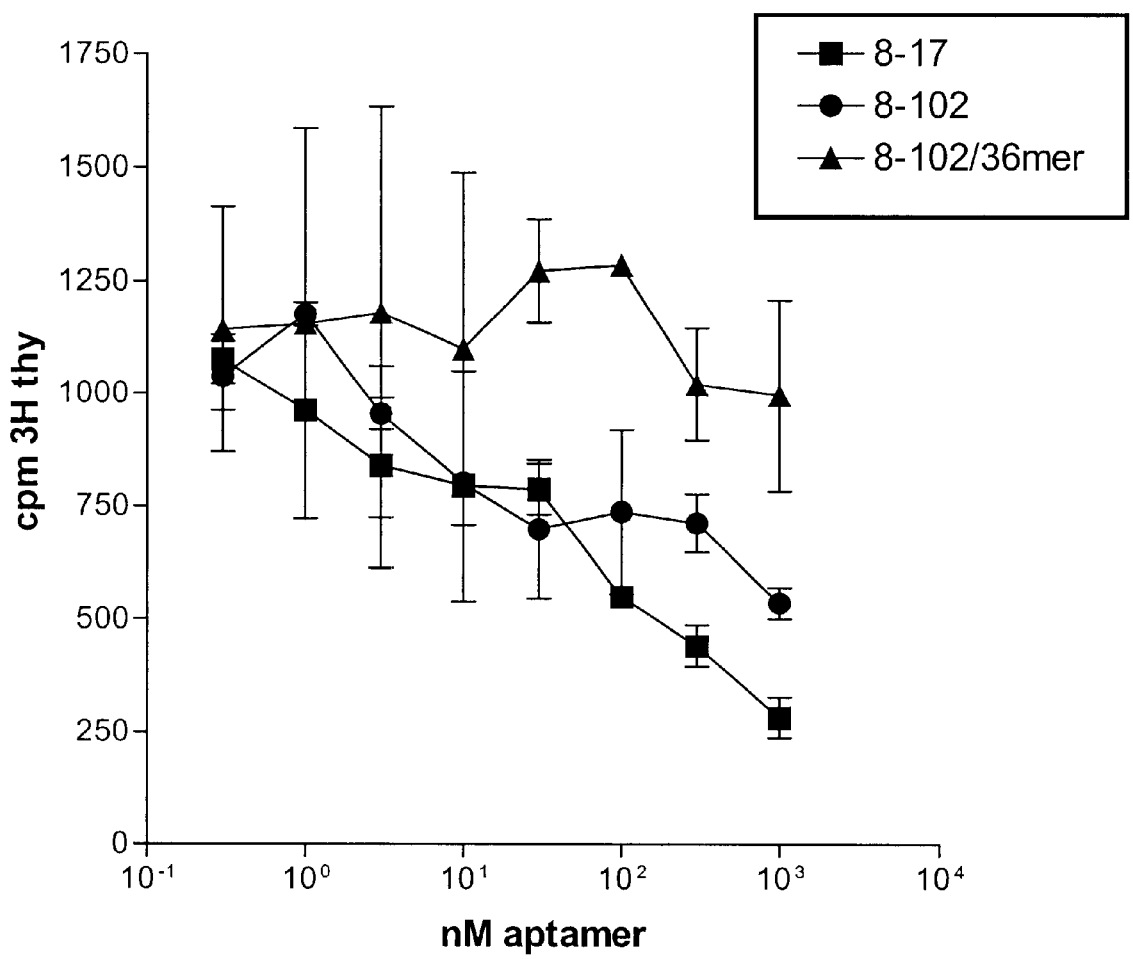
FIG. 10 shows aptamer inhibition of 100 ng/ml HGF stimulation of 4MBr-5 cells.

The 36mer derivative of aptamer 8-102 described above was tested for inhibition in vitro in a 4MBr-5 cell proliferation assay (FIG. 10). Although the 36mer retained high-affinity binding to HGF, it did not retain inhibitory activity in vitro comparable to its parent aptamer 8-102 and aptamer 8-17 (FIG. 10).

Figure 11A:
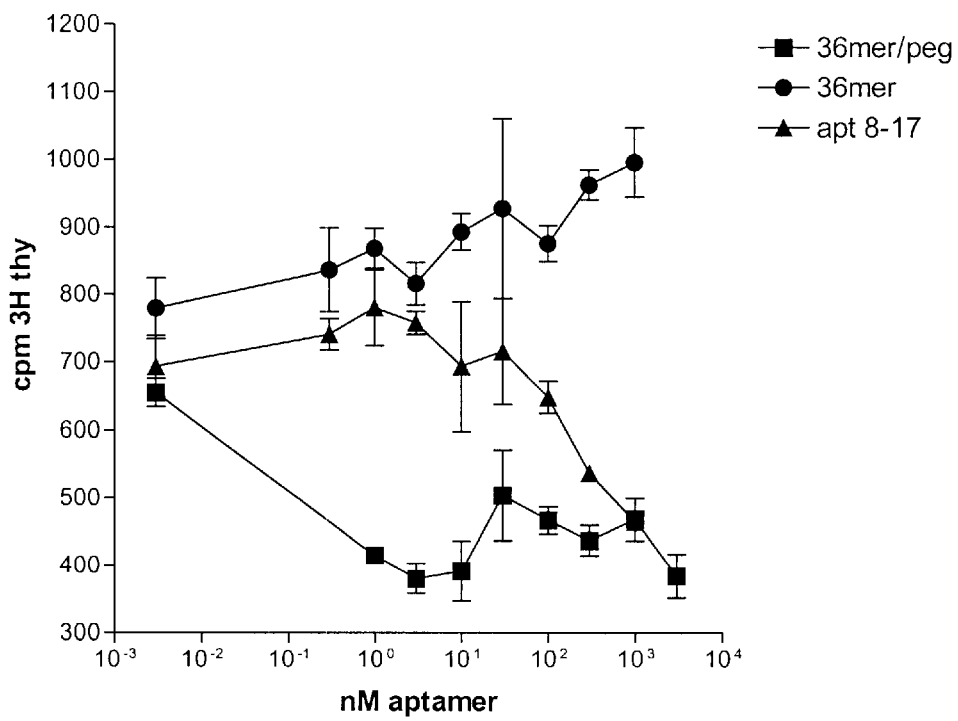
FIG. 11A shows the effect of PEGylation of 36mer.
Figure 11B:
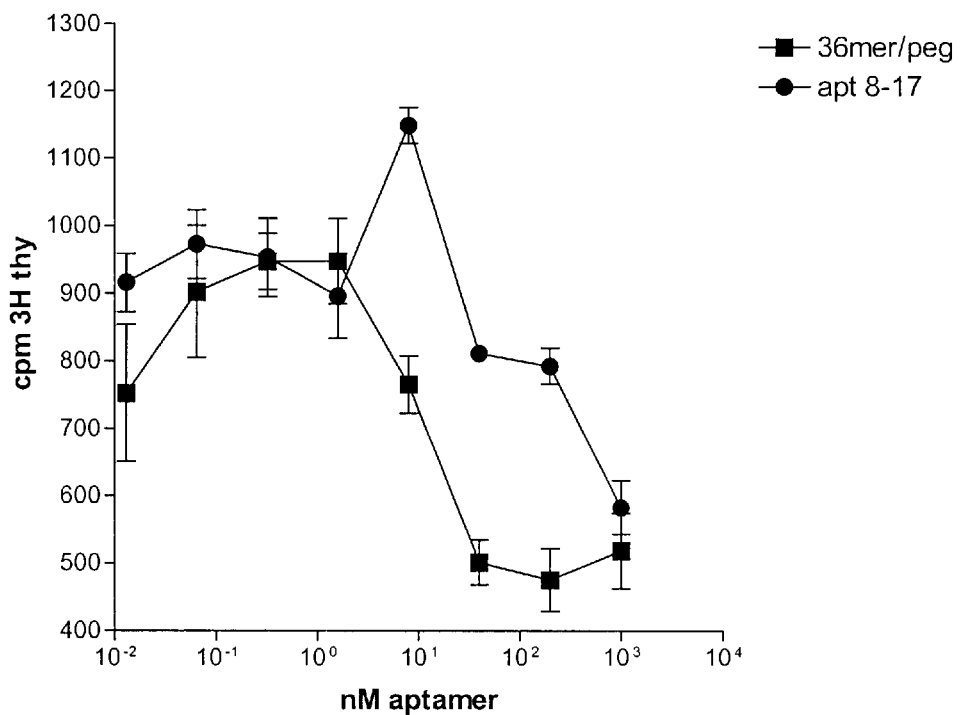
FIG. 11B shows a comparison of PEGylated 36mer to best full-length inhibitor 8–17.
Figure 12:
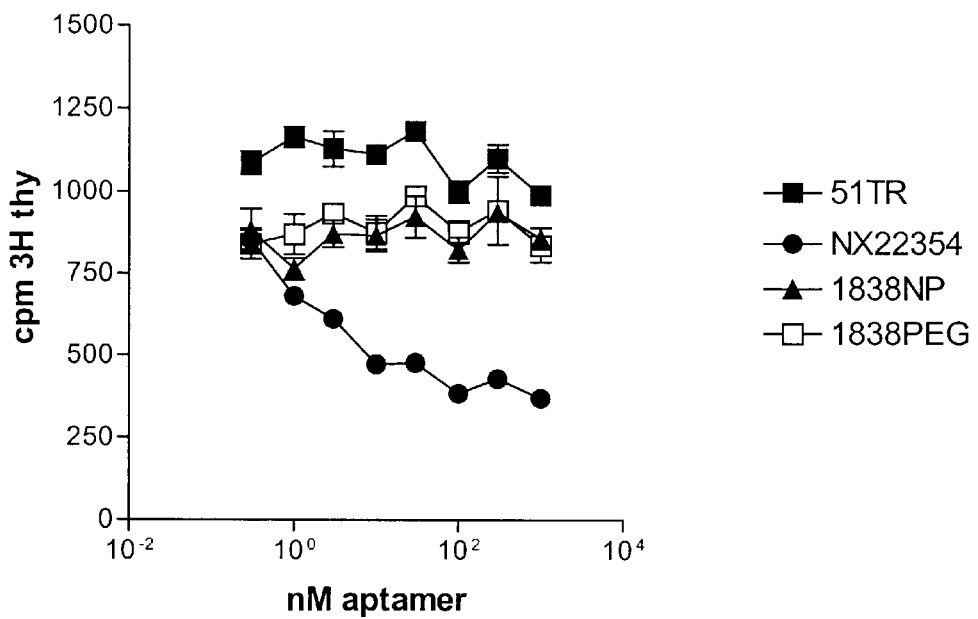
FIG. 12 shows aptamer inhibition of 50 ng/ml HGF stimulation of 4MBr-5 cells.

In order to improve the activity of the 36mer, we tested it in a formulation with a 3'-dT cap and 5'-40K PEG. The modified aptamer, designated NX22354, was tested for inhibition of HGF-mediated proliferation 4MBr-5 cells (FIG. 11A). The data indicate that the 36mer-PEG aptamer inhibits HGF, and that it performs at least as well as the full-length aptamer 8-17, which had previously exhibited the strongest inhibition of all aptamers tested. As expected, the non-PEGylated 36mer did not inhibit HGF, suggesting that the addition of PEG and/or the 3'-cap contribute to the aptamer's bioactivity. This experiment was also done at lower aptamer concentrations, supporting the previous result and showing more clearly that 36mer-PEG aptamer is a better inhibitor that the 8-17 full-length aptamer (FIG. 11B). Also tested by this assay was a non-binding aptamer containing a 3'-dT cap and 5'-40K PEG, the VEGF aptamer NX1838, which had no effect on HGF stimulation (FIG. 12). In this same experiment, a non-PEGylated version of NX1838 and the truncate SELEX aptamer Tr51 were shown to have no inhibitory effect on HGF (FIG. 12). This suggests that Tr51, similar to the 36mer base aptamer of NX22354, may require 5'-40K-PEG to inhibit HGF function.

Inhibition of HGF-mediated Stimulation of Cell Migration

HGF readily stimulates cell movement, hence the name, scatter factor. We assayed the inhibitory effect of HGF aptamers by measuring their effect on A549 cell migration across a Matrigel coated membrane with 8.0 micron pores as described in Materials and Methods (Table 6). The NX22354 aptamer fully inhibited HGF-mediated migration at both 1 and 0.2 µM concentrations, but at 0.04 µM, the effect was negligible. The monoclonal antibody control (sample 3) was moderately effective at the 1 µg/ml dose, which is above its published $EC_{50}$ value of 0.1–0.3 µg/ml for inhibition of 4MBr-5 cell proliferation.

Combined Inhibitory Effect of HGF and VEGF Aptamners on HUVEC Proliferation

Figure 13:
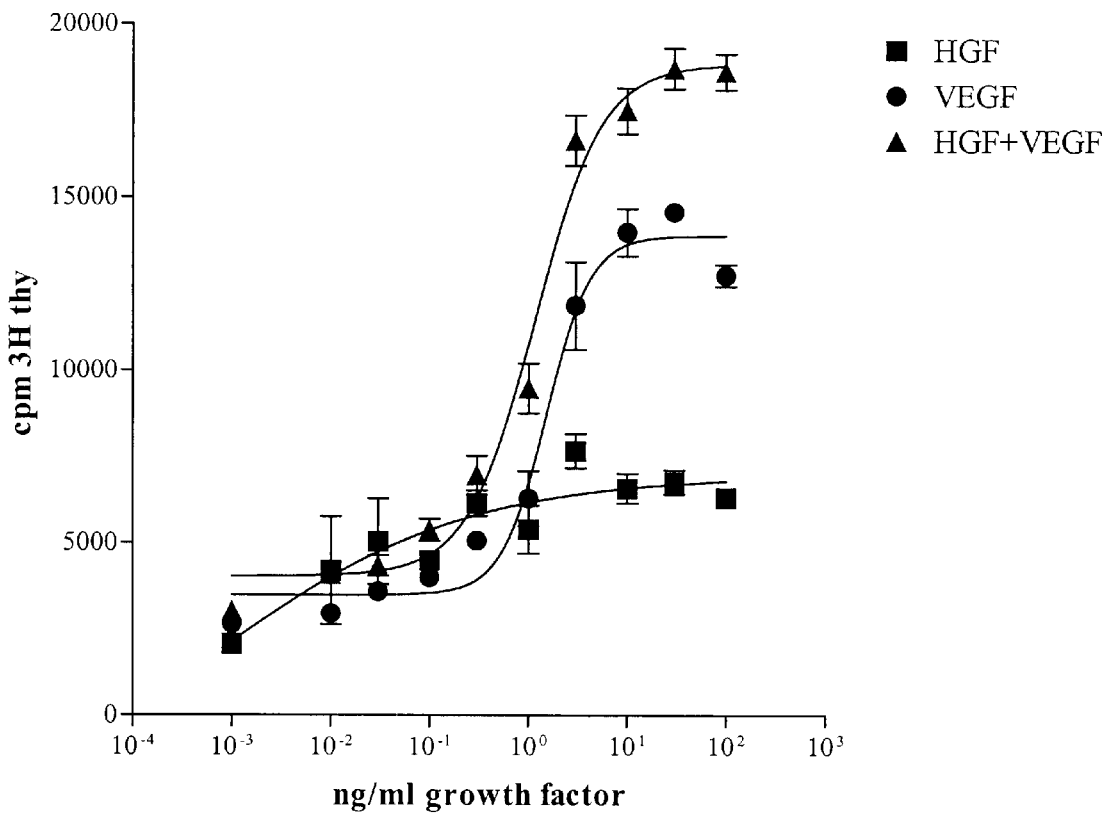
FIG. 13 shows HUVEC mitogenesis by 10 ng/ml HGF, 10 ng/ml VEGF, or both HGF and VEGF.

It was reported that VEGF and HGF have an additive stimulatory effect on HUVEC proliferation (Van Belle 1998, Circulation. 97:381–90). We observed this effect when VEGF and HGF were added, singly and in combination, to HUVECs, and we measured incorporation of $^3$H-thymidine (FIG. 13). As expected, stimulation by HGF was relatively weak compared with that of VEGF and together, the stimulatory effect was greater than that elicited by VEGF alone.

Figure 14A:
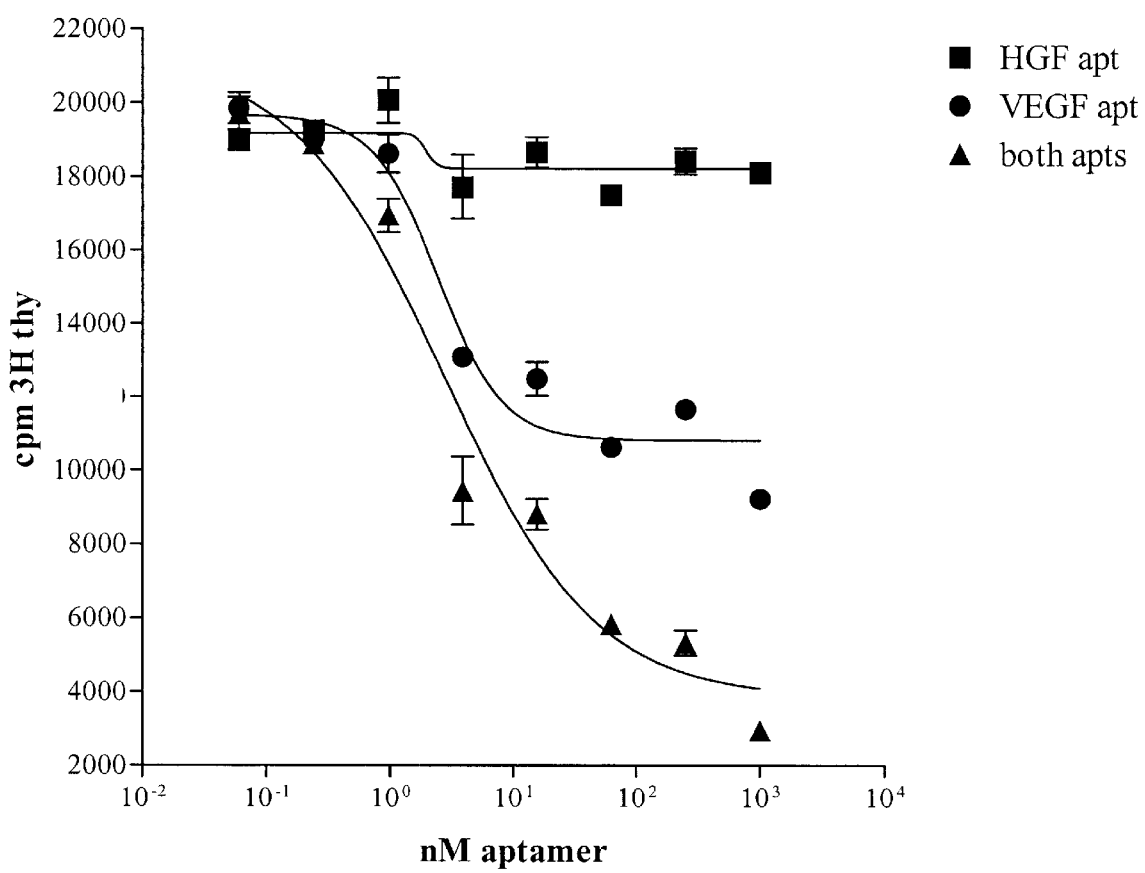
FIG. 14A shows stimulation by both HGF and VEGF inhibited by either HGF or VEGF aptamers or both.

Based on these curves, we chose to add each cytokine at 10 ng/ml for optimal stimulation in the aptamer inhibition experiments. We then tested the effect of adding one or both aptamers to the doubly-stimulated cells in the presence of both growth factors (FIG. 14A). We observed that each aptamer partially inhibits the stimulation and that both aptamers result in complete inhibition. Interestingly, the magnitude of the inhibitory effect of each aptamer roughly corresponds with the magnitude of the stimulation conferred by each cytokine. This observation suggests that the stimulatory effect of each cytokine can be inhibited independently, and that the two cytokines stimulate HUVECs independently.

Figure 14B:
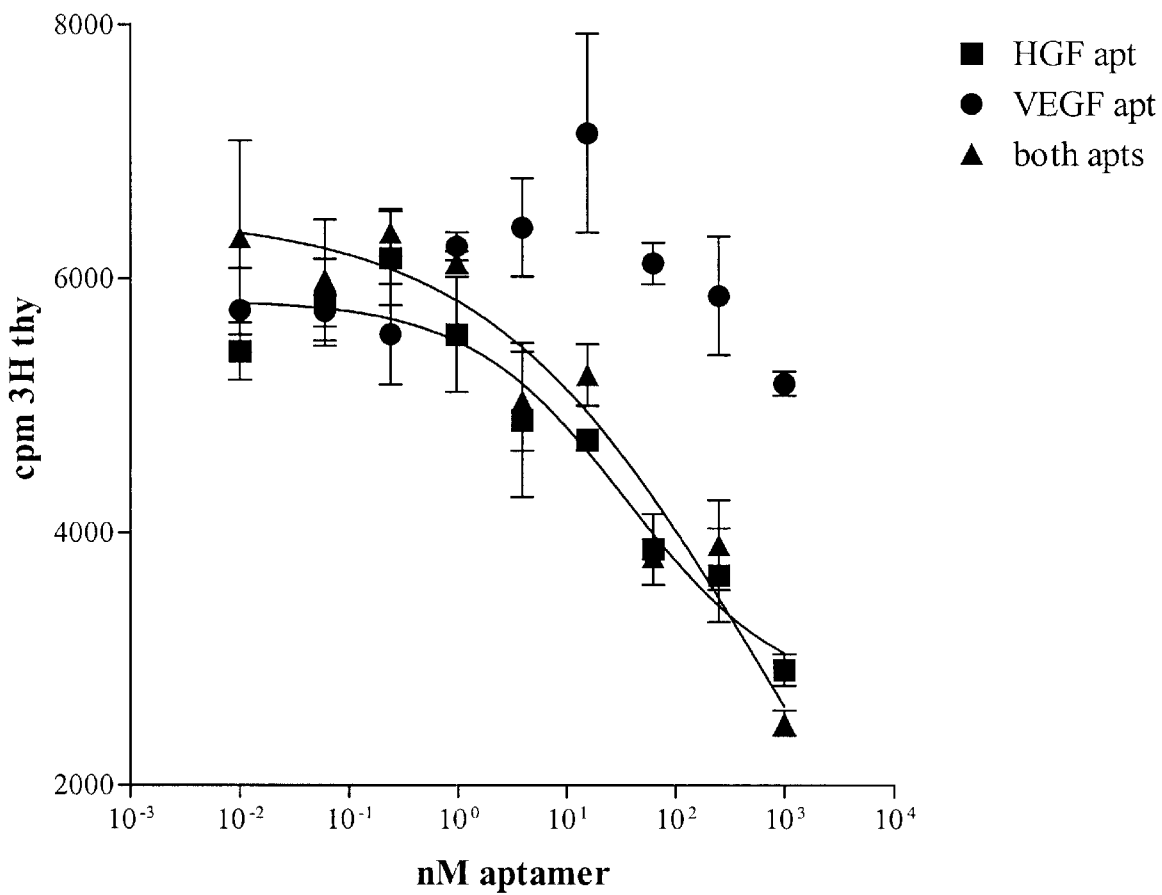
FIG. 14B illustrates stimulation by HGF alone inhibited by either HGF or VEGF aptamer or both.
Figure 14C:
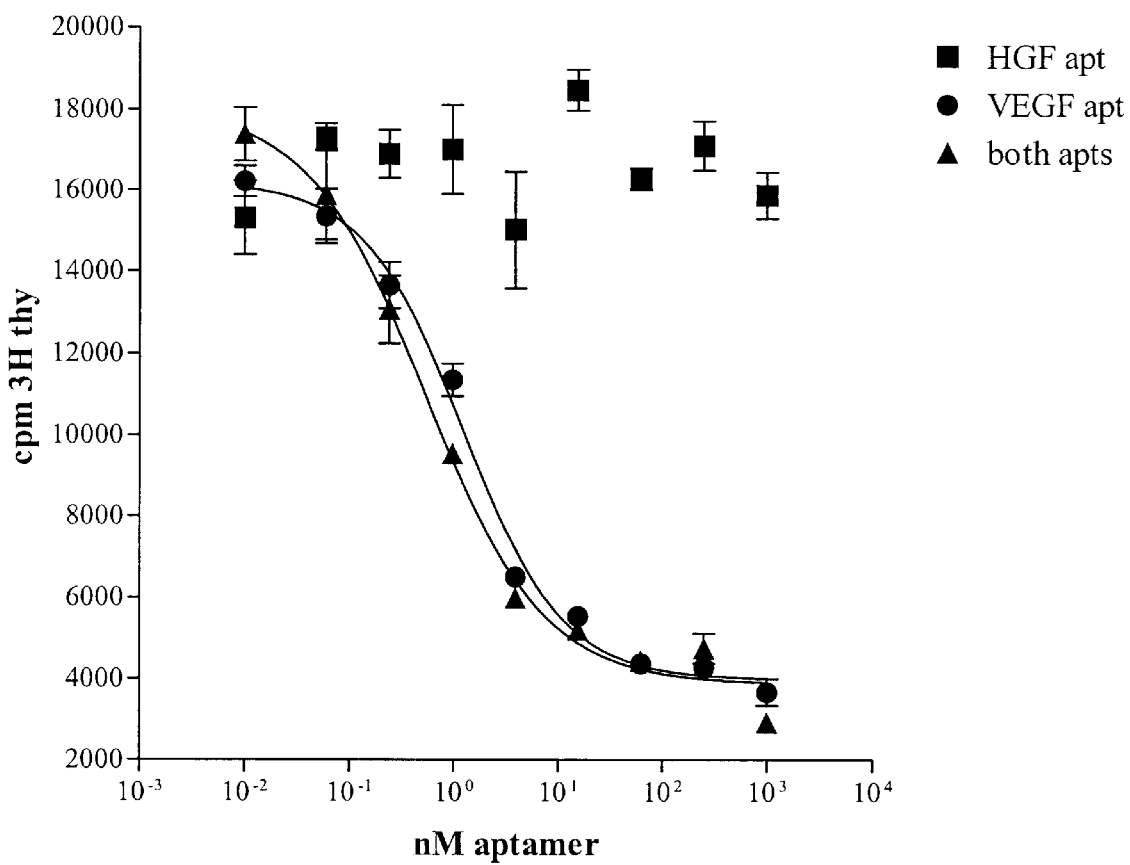
FIG. 14C illustrates stimulation by VEGF alone inhibited by either HGF or VEGF aptamer or both.

The remaining two panels of FIG. 14 (FIG. 14B and FIG. 14C) are controls in which each cytokine being administered separately, demonstrating that the HGF and VEGF aptamers do not cross-react, that is, each aptamer affects only the cytokine against which it was selected. For the HGF stimulated cells, we observed inhibition by the HGF aptamer NX22354, but not by the VEGF aptamer NX1838 (FIG. 14B). Conversely, stimulation by VEGF was inhibited by the VEGF aptamer NX1838, but was unaffected by the HGF aptamer NX22354 (FIG. 14C).

These data, along with the fact that HGF, like VEGF, is an angiogenesis factor make it intriguing to consider dual administration of VEGF and HGF aptamers to treat tumors. Furthermore, the availability of aptamers which inhibit other growth factors suggests further combinations of the VEGF or the HGF aptamer in combination with other aptamers, for example, aptamers that inhibit bFGF, platelet-derived growth factor (PDGF), transforming growth factor beta (TGF), keratinocyte growth factor (KGF), and/or their receptors allowing for the possibility that any combination of these inhibitors may be relevant. The goal is to have an array of aptamer-inhibitors of cytokines and their receptors and to be able to tailor combination treatments for specific disease states.

2'-O-methyl-purine Substitution of HGF Aptamer NX22354

Figure 15:
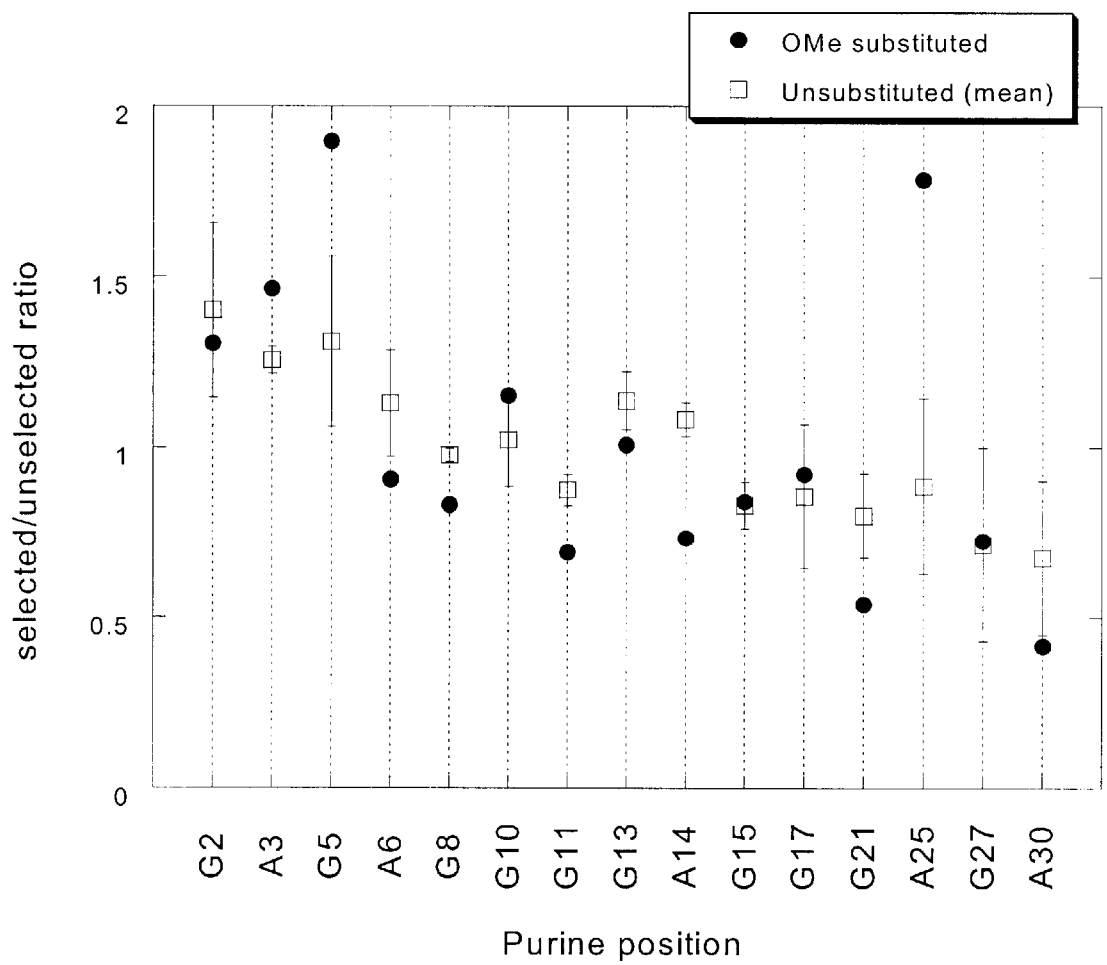
FIG. 15 depicts ratios of selected to unselected partially 2'-O-methyl substituted purines in aptamer NX22354.

To improve the stability and pharmacokinetics of NX223 54, we determined which of the 17 2'-OH purines could be replaced. We did this by synthesizing four partially substituted 2'-O-methyl-purine variants of the base sequence of NX22354 followed by analysis as described in Materials and Methods. The four partially-substituted oligonucleotides were synthesized with a 1:1 ratio of 2'-O-methyl amidite:2'-OH amidite (Table 7). The data analysis measures the ratios of the selected to unselected RNA at each substituted purine position, based on quantitation of bands from the gel. The data are summarized by position (FIG. 15). At each position, the three unsubstituted aptamers provide an important comparison, which is expressed as an average of the three unsubstituted aptamers with standard deviation represented by the error bars. Points that occur at ratios higher than that of the nearby positions are likely to require 2'-OH for binding.

The data strongly indicate that two positions, G5 and A25, do not tolerate 2'-OMe substitution. Two other positions, A3 and G10, show a slight preference above the standard deviation of the unselected RNA.

The set of OMe aptamers were also examined for binding to HGF (data not shown). The binding data indicate that the OMe1 and OMe3 bind as well as the parent unsubstituted 36mer, whereas OMe2 and OMe4 bind less well. This suggests that the substitutions in OMe2 and OMe4 are less well tolerated with respect to HGF binding in solution, consistent with the fact that OMe2 and OMe4 are substituted at A25 and G5, respectively.

To confirm these results, two aptamers were synthesized which are fully 2'-O-methyl substituted at the apparently well-tolerated positions. The sequences are shown below, with the 2'-OH-purines shown underlined. All other purines have 2'-OMe and the pyrimidines are 2'-fluoro substituted.

4×Sub 2'-OH. GGACGAUGCGGCGAGUGCCUGUUU
    AUGUCAUCGUCC                    SEQ ID NO:186

2×Sub 2'-OH. GGACGAUGCGGCGAGUGCCUGUUU
    AUGUCAUCGUCC                    SEQ ID NO:187

Sequence 4×Sub 2'-OH contains all four of the 2'-OH-purines in question, while 2×Sub 2'-OH has only the two 2'-OH-purines most likely to be required.

Figure 16:
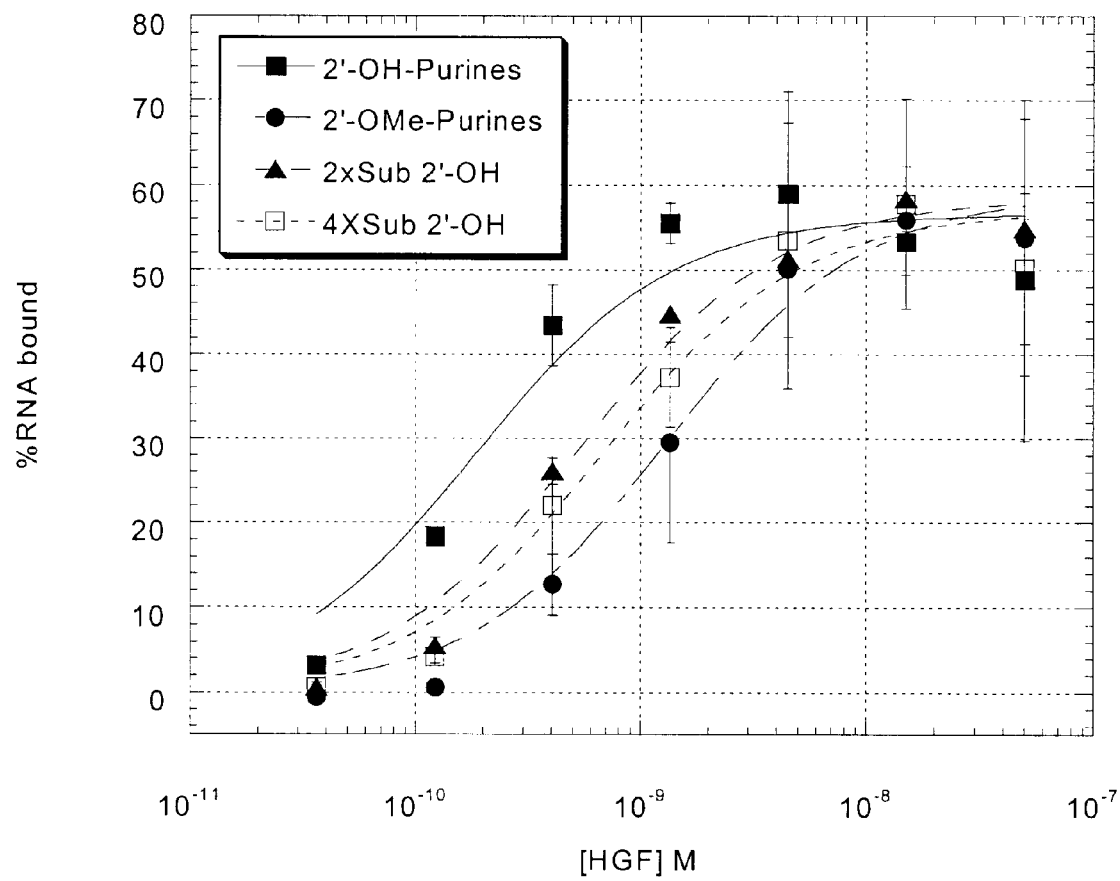
FIG. 16 illustrates 2'-O-methyl substituted derivatives of NX22354 binding to HGF: average of two experiments.

Binding of these oligomers to HGF was examined compared to the unsubstituted parent and the fully 2'-O-methyl substituted RNA (FIG. 16). Based on these binding curves, NX22354 tolerates 2'-OMe substitution at all purines except G5 and A25 (aptamer 2×Sub 2'-OH) with minimal loss of binding affinity. The other two positions in question apparently are not required to be 2'-OH since aptamer 4×Sub 2'-OH binds no better than aptamer 2×Sub 2'-OH.

Two aptamers have been synthesized with 5'-40K-PEG and a 3'-dT cap: one is fully 2'-O-methyl substituted and the other contains 2'-OH at positions G5 and A25. One of these will presumably supplant NX22354 as the lead HGF aptamer for further testing in vitro and in vivo.

Results—c-met c-Met SELEX

In the c-Met plate SELEX experiments, the concentration of nucleic acids was lowered initially, but then raised in later rounds so that the ratio of the nucleic acid to protein would be very high. This was done in order to create conditions of high stringency which may select for higher affinity aptamers. Stringency was also applied by increasing the number of washes.

SELEX Pool Binding

Figure 17A:
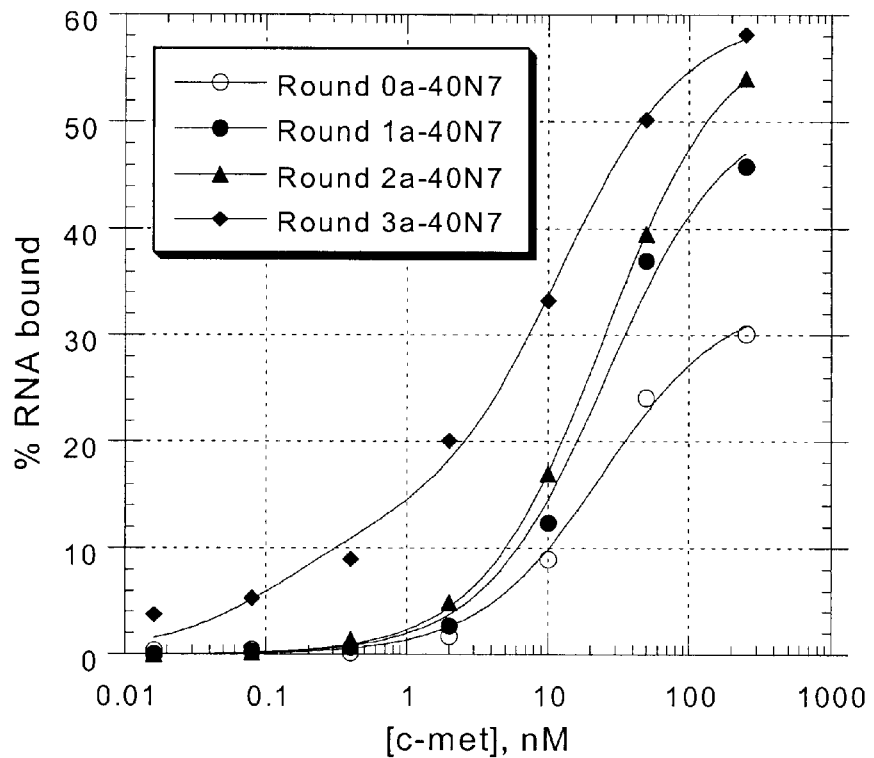
FIG. 17A shows c-Met SELEX 40N7.
Figure 17B:
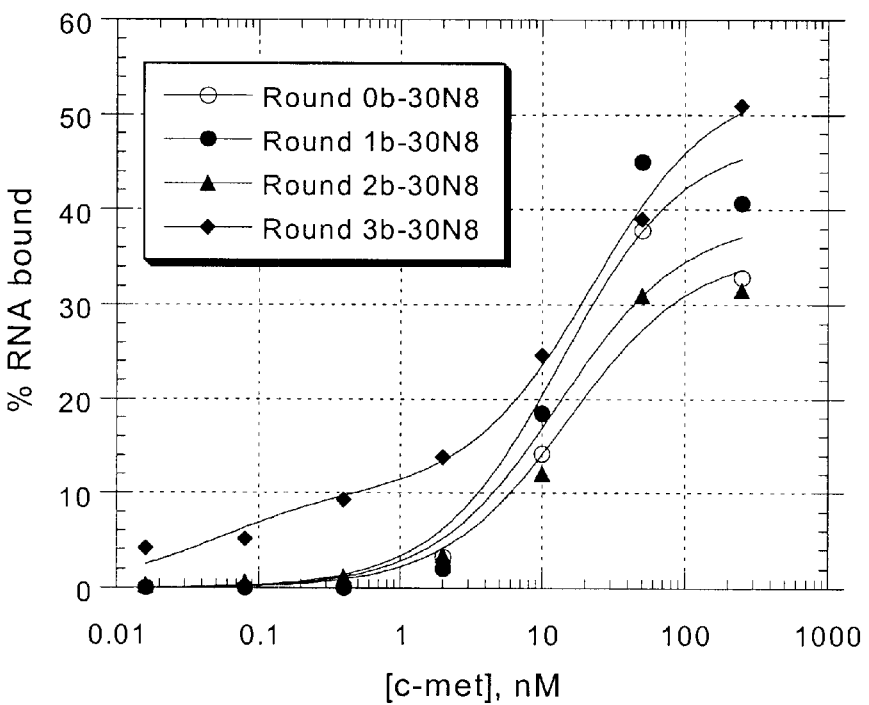
FIG. 17B shows c-Met SELEX 30N8.
Figure 17C:
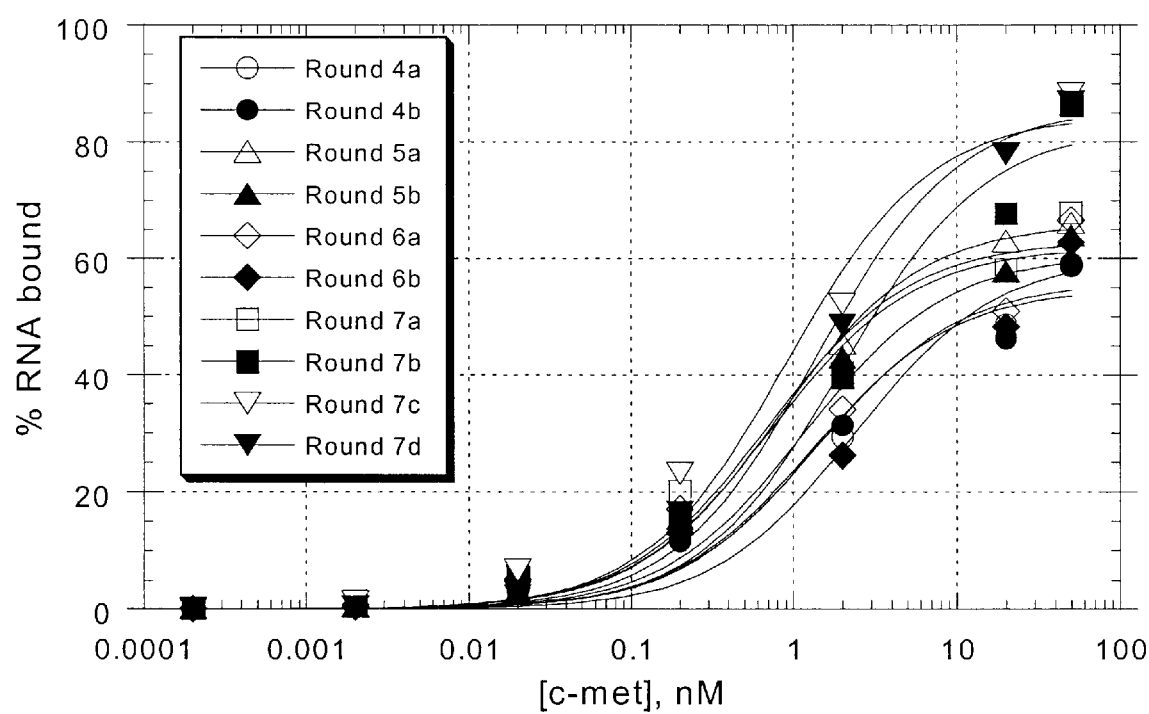
FIG. 17C shows both SELEXes: a, c pools, 40N7; b, d pools, 30N8.

Binding of SELEX pools to c-met was assessed through round 7 (FIG. 17). The binding data indicate that the SELEX resulted in about a 20 fold improvement in $K_d$ from 20 nM to 1 nM for both "a" (40N 7) and "b" (30N8) pools.

Since the c-met protein used in SELEX is an IgG fusion protein, we tested random 40N7 and round 7c RNA pools for binding to human $IgG_1$ and c-met. The binding dissociation constants obtained are as follows:

TABLE 8 binding and dissociation constants

| SELEX round | Protein | $K_d$ |
|---|---|---|
| random | $IgG_1$ | ~1 μM |
| 7c | $IgG_1$ | 23 nM |
| random | c-met | 100 nM |
| 7c | c-met | 2 nM |

The affinity of round 7c RNA for both $IgG_1$ and c-met proteins improved about 50-fold. There are several interpretations to this result. Aptamers may have been selected which bind with better affinity to both proteins. This assumes that the difference in binding between $IgG_1$ and c-met is due to c-met specific aptamers. However, the two proteins were made in different cell lines which may have different glycosylation patterns which could influence binding. Thus, if the differences in affinity are due to differences between the free $IgG_1$ protein and the $IgG_1$ domain in c-met, then there might be few if any c-met specific aptamers in the round 7 pool.

Figure 18:
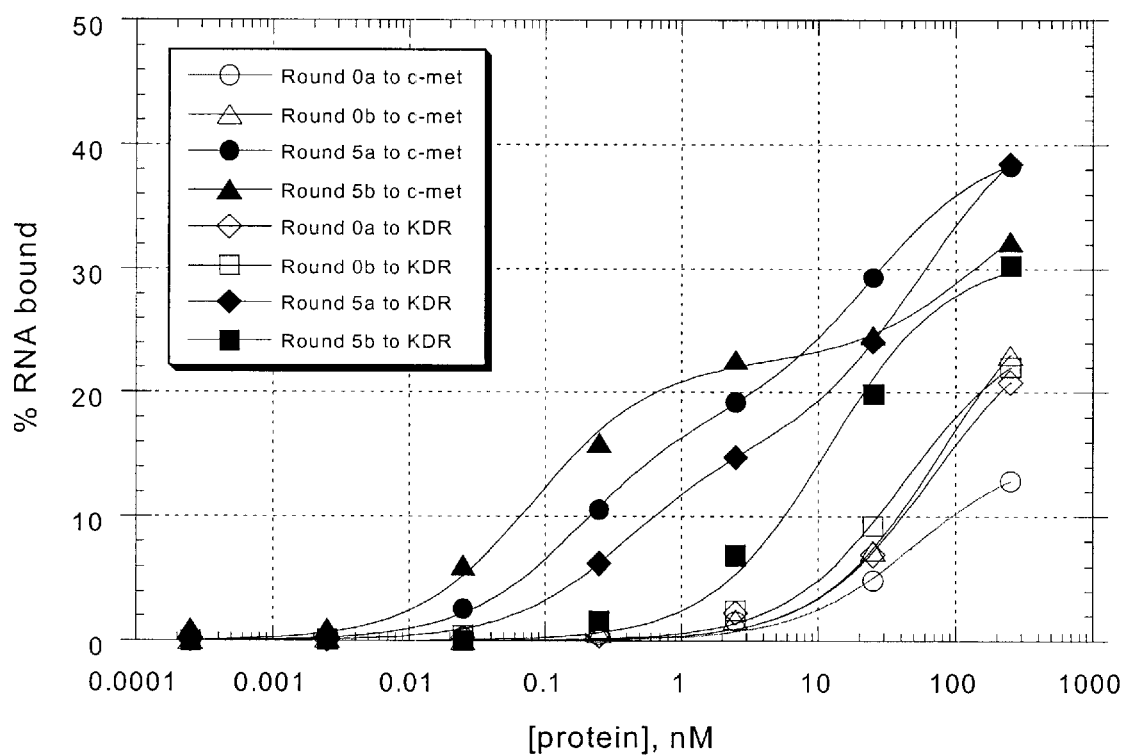
FIG. 18 illustrates binding of c-met SELEX pools to c-met and KDR Ig fusion proteins.

In order to address these issues further, random and round 5 RNA pools from both libraries were examined for binding to the c-met and KDR proteins (FIG. 18). Both of these proteins were made in the same cell line and contain the same $IgG_1$-$His_6$ sequence. Random RNA from both libraries binds about the same to each protein ($K_d$=~50 nM). Round 5 from the both libraries of c-met SELEX binds better to c-met than to KDR (~100-fold better for the 30N8 pool and 3-fold better for the 40N7 pool). However, round 5 RNA pools do bind better than random RNA to KDR. These results imply that, while there are probably aptamers which bind to human $IgG_1$ or $(HIS)_6$ tag in the round 5 pools, there may also be c-met aptamers.

Detection of IgG Aptamers By PCR

Another approach for determining if $IgG_1$ aptamers are present in the SELEX pools was to subject them to PCR. Predominant $IgG_1$ aptamers have been isolated from N7 type libraries which have a known sequence (Nikos Pagratis and Chinh Dang, personal communication). For the PCR, a DNA oligonucleotide:

ML-124; 5'-ACGAGTTTATCGAAAAAGAACGATGGT-
   TCCAATGGAGCA-3'  SEQ ID NO:188 was used that is complementary to the most prevalent N7-series human $IgG_1$ aptamer sequence, and differs by only a few bases from most other $IgG_1$ aptamers. This PCR primer is the same length as the selected sequence of the major $IgG_1$ so that it can tolerate mismatches and hybridize to similar sequences.

The ML-124 3'-primer:

ML-34; 5'-CGCAGGATCCTAATACGACTCA-
   CTATA-3'  SEQ ID NO:189 was used with a 5'-primer containing the T7-promoter sequence present in all cloned aptamers to amplify 40N7 series nucleic acids pools: random, 1a, 2a, 3a and 4a (data not shown). Since $IgG_1$ aptamers have not been isolated from an N8 type library, this analysis was not done for the 30N8 SELEX. PCR of random and c-met SELEX round 1a pools yielded no signal after 20 cycles. However, rounds 2a, 3a, and 4a had steadily increasing signals that were easily detectable after 10 PCR cycles. Thus $IgG_1$ aptamers appeared relatively early in the 40N7 SELEX experiment. For a negative control, PCR was done with a nucleic acid pool from a SELEX known to lack $IgG_1$ aptamers. For positive controls, PCR was done with pools from either an N7-based $IgG_1$ or CTLA4-$IgG_1$ SELEX. $IgG_1$ aptamers were first isolated from both of these SELEXes. The negative control had no detectable $IgG_1$ aptamers after 20 PCR cycles. The positive controls had detectable signals after 10 PCR cycles.

C-met Aptamers

The sequences of 19 clones from round 7c-40N7 fall into five families with two sequences each, a group with three unrelated members, and six sequences closely related to known $IgG_1$ aptamer sequences (Table 9). Thus, at least 6 of the 19 clones (32%) are human $IgG_1$ aptamers. This confirms the results of previous analysis that indicated the presence of $IgG_1$ aptamers in this SELEX experiment.

Of the 13 clones sequenced from round 7b-30N8, six are almost identical, another five are closely related, and two are distinct (Table 10).

Nine clones were tested for binding to c-met or KDR, six from the 40N7 series and three from the 30N8 series. These clones were chosen for the following reasons. Clone 7b-4 is the most frequent clone in family 1 and is representative of almost all of the sequences isolated from the 7b-30N8 library. Clones 7b-10 and 7b-12 are the two clones from the 7b-30N8 library that bad different sequences. From the 7c-40N7 pool, the chosen representatives were: family 1 (clone 7c-1), family 2 (clone 7c-4), family 3 (clone 7c-23), family 4 (clone 7c-26), family 5 (clone 7c-25), and the presumed IgG1 family (clone 7c-3).

Figure 19A:
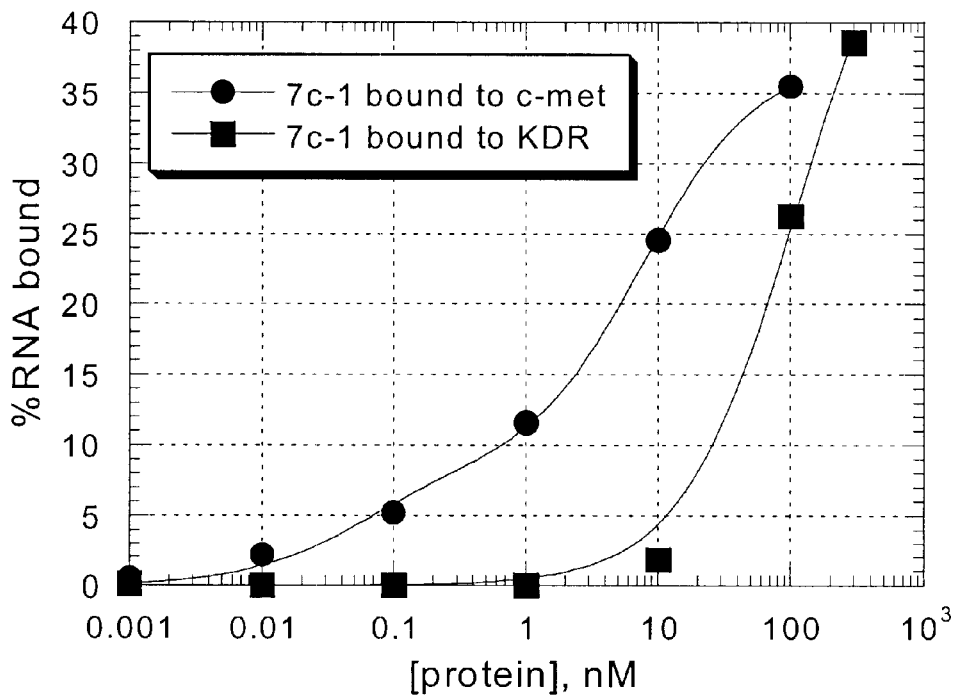
FIG. 19A shows clone 7c-1.
Figure 19B:
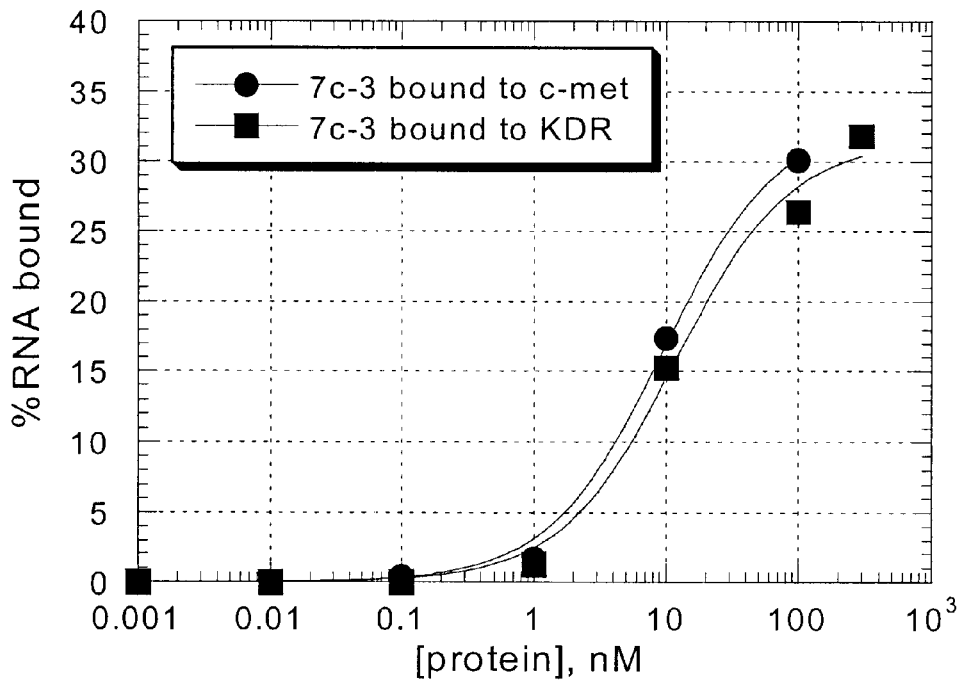
FIG. 19B shows clone7c-3.

Results are shown for only two clones, including 7c-1 which was the only one observed to bind to c-met better than KDR (FIG. 19A). Clone 7c-1, which appeared twice in the 40N7 series, may exhibit biphasic binding behavior with a high affinity binding $K_d$ of ~50 pM and a lower affinity binding $K_d$ of ~5 nM. All eight other clones bound to KDR as well as to c-met, including 7c-3, which is shown here as representative example (FIG. 19B). Clone 7c-3 and all others besides 7c-1 are presumed to be $IgG_1$ aptamers.

In summary, two clones (identical to 7c-1) out of 32 apparently bind c-met specifically and with high affinity. The remaining clones appear to be $IgG_1$ aptamers.

TABLE 1

Binding affinities of HGF SELEX 1 pools
with and without competitor tRNA.

| RNA pool | $K_d$ (nM) | $K_d$ (nM)/tRNA |
|---|---|---|
| random 30N7 | 1.6 | 550 |
| HGF SELEX 1 Rd.8 | 0.07 | 0.35 |
| HGF SELEX 1 Rd.9 | 0.09 | 0.42 |

TABLE 2

HGF 30N7 aptamer sequences and binding affinities.

| Seq. no.[a] | 30N7 random region[b] | SEQ. ID. No. | $K_d$(nM) |
|---|---|---|---|
| 8-122 (2,1) | CGGUGUGAACCUGUUUAUGUCCGCGUACCC | 18 | 0.097 |
| 8-108 | CGGUGUGGACCUGUUUAUGUCCGCGUACCC | 19 | ND[c] |
| 8-115 | AGUGAUCCUAUUUAUGACAUCGCGGCUGC | 20 | ND |
| 8-125 | UGUGAACCUGUUUAUGUCAUCUUUUGUCGU | 21 | 0.075 |
| 8-155 (1,1) | UGUGAACCUAUUUAUGCCAUCUCGAGUGCC | 22 | 0.093 |
| 8-162 | CGUGAGCCUAUUUAUGUCAUCAUGUCUGUC | 23 | ND |
| 8-165 | CGAGAGCCUAUUUAUGUCAUCAUGCCUGUG | 24 | 0.100 |
| 8-171 | CGGGAGCCUUUUUAUGUCAUCAUGUCUGUG | 25 | 0.120 |
| 8-114 (4,2) | CGUGAGCCUAUUUAUGUCAUCAUGUCUGUG | 26 | 0.071 |
| 8-203 | CGCGAGCCUAUUUAUGUCAUCAUGUCUGUG | 27 | 0.140 |
| 8-215 | CGUGAGCCUAUUUAUGUCAUCAUGUCUGGU | 28 | 0.077 |
| 8-217 | CGUGAGCCUAUUUACGUCAUCAUGUCUGUG | 29 | ND |
| 8-222 | UGUGAACCUAUUUAUGCCAUUAUGUCUGUG | 30 | 0.130 |
| 8-225 | CGUGAGCCUAUUUAUGUCAUCAAGUCUGUG | 31 | ND |
| 8-102 | CGAGUGCCUGUUUAUGUCAUCGUCCGUCGU | 12 | 0.060 |
| 11-9 | CGUGAGCCUGUUUAUGACCUCGUCCAUGGC | 32 | 0.074 |
| 11-58 | CGUGAGCCUAUUUAUGACAUGUCCCUCGAG | 33 | ND |
| 11-59 | CGUGAGCCUGUAUAUGUCAUUGUUCUCCGG | 34 | 0.110 |
| 11-57 | UGAGUACCUGUUUAUGUCACCACUUUCCCC | 35 | ND |
| 11-103 | UGAUUACCUA UUAUGUC UCGCCCUCUC | 36 | 0.200 |
| 11-110 | UGAUUACCUAUUUAUGUCAUGCUCCUCCCC | 37 | 0.086 |
| 11-65 | UGAUAACCUGUUUAUGCCAUCGUGCUGGGC | 38 | 0.110 |
| 11-167 | UGAUAACCUGUUUAUGUCAUCGUGCUGGGC | 39 | ND |
| 11-201 | UGAGAACCUAUUUAUGUCAUCUGGC | 40 | ND |
| 11-162 | UGAUAACCUAUUUAUGACGUCGUGGCUCCC | 41 | ND |
| 11-202 | UGGGAACCUAUUUAUGUCAUC UCCGUCCC | 42 | ND |
| 11-106 | CGAUGAUGCCUGUUUAUGUCGAUGUCCCCC | 43 | 0.120 |
| 11-158 | CGAUAGCCUAUUUAUGACCUCGUCCCCGUG | 44 | 0.170 |
| 11-112 | CGUGAGCCUAUUUAUGACAUCGUUCUUGGC | 45 | ND |
| 11-124 | CGUGAGCCUAUCUAUGUCAUCGUGUGUGCC | 46 | ND |
| 11-122 | UGAGUACUAUUUAUGUCGUCGUUCGUGCC | 47 | ND |
| 11-217 | CGUGAGCCUUCCAAUGACGUCGUCCUUGGC | 48 | 0.071 |
| 8-104 | GCGACUCAAUCUGAAUCGUCUUGUCCCGUG | 49 | 0.050 |
| 11-76 | UCAGCGGCGCGAGCCUGUUUAUGUC UGCUG | 50 | 0.076 |
| "consensus" | CGUGAGCCUAUUUAUGUCAUCGU-C-UG | 51 | |
| | | | |
| 11-8 | UCAGUAUGACU UUUAUAGCA CGUUCGCCC | 52 | 0.150 |
| 11-153 | ACAGGUAGUCU UCUAUAGCA CUUCCUCCCC | 53 | 0.190 |
| 11-157 | UCAGAAUGACU UUCAUAGCA CGCUUUCCC | 54 | 0.260 |
| 11-222 | ACAUAAGUCU UCUAUAGC UCGUCCUUUGUG | 55 | 0.077 |
| 11-223 | UCAGUAUGGCU UCUAUAGC UCGUUCCUCGG | 56 | 0.120 |
| | | | |
| 8-126 (3,1) | GUGACUCAAAAUGGUGAUCCUCG UUUCCGC | 57 | 0.099 |
| 8-101 | GUGACUCAAAAUGGUGAUCCUCGAUUUCCGC | 58 | 0.095 |
| 8-105 | GUGACUCAAAAUGGUGAUCCUCGAUUGCCGC | 59 | ND |
| 8-103 | GCCGAAAAU UCGUCGACAUCUCCCUGUCUG | 60 | 0.120 |
| | | | |
| 8-118 | GGCGACUUUCCUCCAAUUCUCACCUCUGCA | 61 | 0.160 |
| 8-119 | GCCAUUCGAUCGA UUCUCCGCCGGAUCGUG | 62 | 0.110 |
| "consensus" | CGUGAGCCUAUUUAUGUCAUCGU-C-UG | 51 | |
| | | | |
| 8-3 (2) | AUCCCGCGAC CAGGGCGUU UCUUCCUCGUCC | 63 | 0.130 |
| 8-112 (3) | UCCCGAAUUUAAGUGCGUU UCCUCGCGUC | 64 | 0.130 |
| 8-154 (3) | UCCCAAGAUUCAGGGCGUU UCUUCCUCGUC | 65 | 0.120 |
| 8-117 | UCCCAAGUUUCAGGGCGUU UCUUCCUCGUC | 15 | 0.130 |
| 8-123 | UCCCGAGUUUGAGGGCGUU UCUUCUUCGUC | 66 | 0.210 |
| 11-121 | UCCCAGUUUCAgGGGCGAU UCCUCUUCGUC | 67 | ND[c] |
| | | | |
| 8-17 (7,1) | GCGGCU CGAUG UCGUCUUAUCCCUUUGCCC | 68 | 0.095 |
| 8-16 | GCGGGCU CGAUG UCGUCUUAUCCCCUUUGCCCC | 69 | ND |
| 8-158 | CCCGGCU CGAUG UCGUCUUA CCCCUUUGCCC | 70 | 0.310 |
| 11-104 | GUUUGAG UGAUG UCGUCUUGUCCCGCCUGC | 71 | 0.091 |
| 11-111 | GUUAGAG UUUG UCGUCUUGUCCCAUGUG | 72 | ND |
| 11-163 | GCUUGAGUC UUUG AUCGUCUUAUCCCUCGU | 73 | 0.082 |
| 11-208 | GUUUGAG UGACG AUCGUCUUGUCCCAUGUG | 74 | 0.060 |
| 11-212 | GUUUGAG UUAAA CAUCGGUUUUCUCCUG | 75 | 0.075 |
| 11-6 | GACGCG UUGAUU CAUCGUCUUAUCCUGCUG | 76 | 0.240 |
| 11-126 | GUUUGGGUCU UGAUC UCGUCUUGUCCCGUG | 77 | 0.170 |
| 11-165 | gUUGAUAGG AGUCAU CAUCGUCUUGUCCGC | 78 | 0.073 |
| 11-215 | GUAGUGAG UUUUCAUU GUCGUCCCCGUG | 79 | 0.091 |
| 11-151 | UGAGUCAUAGUGUUG AUCGUCGUAUCCCGU | 80 | 0.170 |
| 11-7 | GUGGAGUCAA AUCGUCUUGUCCCUUGUCCU | 81 | 0.110 |
| 11-166 | GUUUGAG UUCUGACA CGUCUUGUCCCAUGC | 82 | 0.079 |
| 11-17 | GUUAGAGC GUGACAG UCGUCUUAUCCCGGGUCA | 83 | 0.130 |

TABLE 2-continued

HGF 30N7 aptamer sequences and binding affinities.

| Seq. no.[a] | 30N7 random region[b] | SEQ. ID. No. | $K_d$(nM) |
|---|---|---|---|
| 8-113 (2) | UGAAUUCCUCUGGCUGAAAAU GACUUGUGC | 84 | 0.083 |
| 8-60 | UGAAUUCCUUUGGCUGAAAAU GACUUGUGC | 85 | ND |
| 11-221 | GCAGAGCGAAAAUCGUCUUGUCCCCGACGC | 86 | 0.062 |
| ORPHANS | | | |
| 11-123 | GUGACUCAAAAUGGUGAUCCUCGUUUCGC | 87 | 0.090 |
| 8-151 | AGGACUAAUCCCUAAGGAAUAGCUUGCCCG | 88 | 8 |
| 8-174 | UCGAGCUUCUGAGUUAAA CUGGGGCCUCCU | 89 | 0.230 |
| 8-160 | GUCCCCGAAUUUAAAGUGCGUUUUCCUCCGGG | 90 | 0.150 |
| 11-203 | GGUUUUUCUUUUCUUGUUCUCUUCUUUCCCC | 91 | 0.260 |
| 11-224 | ACAGCGGCGACUAGCCUGUUCAUGCCUGCC | 92 | 0.110 |
| 11-107 | GUUCUGUGUGUCCACGUUCUUACCCCUGUG | 93 | 0.140 |

[a]Clone series 8 is from HGF SELEX 1; series 11 is from HGF SELEX 3. Numbers in parentheses refer to repeat occurrences of the same exact sequence. For the series 8 clones, a second number refers to an exact match which was isolated in series 11.
[b]N7 fixed sequences are not shown. (5'-GGGAGGACGAUGCGG-N-CAGACGACUCGCCCGA-3' (SEQ ID NO:2)
[c]ND, not determined.

TABLE 3

HGF 30N8 aptamer sequences and binding affinities.

| Seq. no.[a] | 30N8 random region[b] | SEQ. ID. No. | $k_d$(nM) |
|---|---|---|---|
| 10-28 | CCUGUUCUGAAC GCAAAAUGGCGUGGUGGC | 94 | 0.860 |
| 10-40 | UGUCGUUAGUUUAUUGACAAGGCCCGAAG | 95 | 0.350 |
| 10-52 | UCUUAUUGUGUCCAGCUUCUCCCUGCAGGC | 96 | 0.160 |
| 10-72 | UGUGGCAC UGUUGUCCACAAGGGCCUCA | 97 | 0.450 |
| 10-8 | UUGACAAGGUACCUGUUGCCUGGCGUUUCU | 98 | 0.920 |
| 10-76 | AGUUAGGCUUUAAAGC ACG AUAAUCAGCA | 99 | 0.170 |
| 10-47 | GUCAAGAGG AAAUGACACGG CUCCACUUUUA | 100 | 0.390 |
| 10-2 (10) | GCCUGAGUUAAACAUGACGG UUUGUGACCC | 101 | 0.069 |
| 10-3 | GCCUGAGUUAAACAUGACGGGUUUUGUGACCCCU | 102 | 0.072 |
| 10-23 (4) | GUCUGAGUUGGACACAACGC AUUGAGACCC | 103 | 0.330 |
| 10-24 | GUCUGAGUUgGUCACAACGC AUUGAGACCC | 104 | ND[c] |
| 10-37 | GUCUGAGUCCGU AGGGCGA UUUGUGUCCC | 105 | 3.05 |
| 10-7 | UGCCUUAAGAGCGGAA CUCCCUGACCCACC | 106 | 1.45 |
| 10-13 | GAUCUGUUGGCGU GU CUACCCGACCCUCCU | 107 | 0.720 |
| 10-17 | AACCCUGUUGGCGU GA CGUCCCGACCCUCC | 108 | 0.560 |
| 10-36 | CGUUAGCAUCUGAACGAUGCCCAGCCUCAA | 109 | 1.94 |
| 10-62 | GUUAGACUCAACAUGAGUCCCAGCCUCAA | 110 | 0.440 |
| 10-29 | UCUGUUGGCGUCGU UCUCCUGACCCUCCUC | 111 | 1.75 |
| 10-48 | GAGUUCCCUGUUGAC UCGC UCUCCUGACCC | 112 | 0.310 |
| 10-16 | UACAGCGUGUUGGUCCCGGACGGGACUUAU | 113 | 0.210 |
| 10-11 | CGCCUGGACCGUUUGUUUAUCCCCGUAGUC | 114 | 0.610 |
| 10-18 | CGUGAUUCCUACCAUCA GGUACCUAUCUUG | 115 | 0.300 |
| 10-1 (2) | AGUGAUGUGAGAG CGUGCCUCUAGUCGGUG | 116 | 0.094 |
| 10-57 | CGAGCCUCCUACCGUUU AGGUACC AUCUUG | 117 | 0.140 |
| 10-27 | UUAGCCUCCGACCG UAA GGUCCUUUUCUUG | 118 | 0.830 |
| 10-53 | GGCCUCCAACCGCUAAA GGUUCCAUUCUUG | 119 | 0.310 |
| 10-49 | CCCGACCUCCUGUAACUGGUUGA GGCACUA | 120 | 0.240 |
| 10-31 (2) | GGGUUCCUGAUUGACCCUGUCUCUAGACCC | 121 | 1.90 |
| 10-58 | GGGGAGGCCCUUCAGCCGUCUCCUUGACCC | 122 | 0.440 |
| 10-63 | UGUGAUGUGAGGGC GUGCUUCCUAACGGUG | 123 | 0.190 |
| 40N8 "hitchhiker" sequences | | | |
| 10-19 | UUCAUUAUGCAUCGAACAGUAUACCACAGGUGUUCAUGUG | 124 | ND |
| 10-35 | AUCCAAAUUCUGGUCAUGAGGCGCUGCAGAUACUGCUGCG | 125 | 2.33 |
| 10-38 | UCUGCGGACGGUGAGGUUAAGUUGCAACGACUGCUUGGCG | 126 | 7.38 |
| 10-42 | CAGACCGUGCAAACCCCCCUUAGAGGGUUUUGUCAUUUAC | 127 | ND |

TABLE 3-continued

HGF 30N8 aptamer sequences and binding affinities.

| Seq. no.[a] | 30N8 random region[b] | SEQ. ID. No. | $k_d$(nM) |
|---|---|---|---|
| 10-56 | CCUUAGGGCUCCCAAAAAUCGGGCC CGUCGGGCCGAUCAC | 128 | 0.280 |
| 10-68 | CGCGGGAUUCUCUGAGGACGAGGCACGUGUGGGUAAUUCG | 129 | 1.00 |
| 10-67 | UCGGGCUUGGAUGUGGACGUGUAUUUCUAGCUGUGUACGC | 130 | 0.640 |
| 10-4 | UUGGGUCGGGACUCGAAAGGAUUUGAUAGGAUACAUGAAU | 131 | 0.610 |

[a]Clone series 10 is from HGF SELEX 2. Numbers in parentheses refer to repeat occurrences of the same exact sequence.
[b]N8 fixed sequences are not shown. (5'-GGGAGAUAAGAAUAAACGCUCAA-N-UUCGACAGGAGGCUCACAACAGGC-3')(SEQ ID NO:6)
[c]ND, not detennined.

TABLE 4

List of HGF aptamers and their binding affinities which were tested in vitro for inhibition of activity.

| Seq. no. | random region | Kd (nM) |
|---|---|---|
| "consensus" | CGUGAGCCUAUUUAUGUCAUCGU-C-UG | |
| 8-17 | GCGGCU CGAUG UCGU CUUAUCCCUUUGCCC | 0.095 |
| 8-102 | CGAGUGCCUGUUUAUGUCAUCGUCCGUCGU | 0.060 |
| 8-104 | GCGACUCAAUCUGAAUCGUCUUGUCCCGUG | 0.050 |
| 8-112 | UCCCGAAUUUAAGUGCGUU UCCUCCGCGUC | 0.130 |
| 8-113 | UGAAUUCCUCUGGCUGAAAAUGA CUUGUGC | 0.083 |
| 8-122 | CGGUGUGAACCUGUUUAUGUCCGCGUACCC | 0.097 |
| 8-126 | GUGACUCAAAAUGGUGAUCCUCG UUUCCGC | 0.099 |
| 11-8 | UCAGUAUGACU UUUAUAGCA CGUUCGCCC | 0.150 |
| 11-76 | UCAGCGGCGCGAGCCUGUUUAUGUC UGCUG | 0.076 |
| 11-166 | GUUUGAG UUCUGACA CGUCU UGUCCCAUGC | 0.079 |
| 11-208 | GUUUGAG UGACG AUCGUCU UGUCCCAUGUG | 0.060 |
| 11-222 | ACAUAAGUCU UCUAUAGC UCGUCCUUUGUG | 0.077 |
| 10-2* | GCCGAG UUAAACAUGACG GUUUGUGACCC | 0.069 |
| 8-151 | AGGACUAAUCCCUAAGGAAUAGCUUGCCCG | 8 |

*10-2 contains N8 fixed sequences; all others are N7.

TABLE 5

HGF truncate SELEX 30N sequences.

| Trunc Seq#[a] | # of hits | Sequence of random region (G)G-30N-CA | Identity to full-length | [b] $K_d$(nM) | SEQ. I No. |
|---|---|---|---|---|---|
|  |  | GGACGAUGCGGCGAGUGCCUGUUUAUGUCAUCGUCC | NX22354 | 0.1 | 13 |
| Tr7 | (5) | CGGUGUGAACCUGUUUAUGUCCGCGUACCC | 8-122 | 0.67 | 132 |
| Tr45 | (3) | UGGGAACCUAUUUAUGUCAUCUCCGUCCC | 11-202 | 1.7 | 133 |
| Tr70 |  | UGGGAACCUAUUUAUGUCAUCGUCUGUGCC | New | 2.4 | 134 |
| Tr6 |  | CGUGAGCCUAUUUAUGUCAUCAUGUCUGUG | 8-114 | 9.0 | 135 |
| Tr20 |  | UGUGAACCUGUUUAUGCCAUCUCGAGUCCC | New | 3.4 | 136 |
| Tr23 |  | UGUGAACCUAUUUAUGCCAUCUCGAGUGCC | 8-155 | ND[c] | 137 |
| Tr42 |  | UGAUAACCUAUUUAUGACGUCGUGGCUCCC | 11-162 | 6.1 | 138 |
| Tr44 |  | AGUGAUCCUAUUUAUGCCGUCGCUUCUCGC | New | 6.5 | 139 |
| Tr65 |  | AGAGNUCCUAUUUAUGACAUCCCAUGCCCC | New | 1.4 | 140 |
| Tr48 |  | UGAUCACCUGUUUAUGCCAUCGUUCUGGGC | 11-65 | 1.8 | 141 |
| Tr28 |  | GGUGACCCUUUUUAUGACAUCGCGUCUGGC | New | 4.0 | 142 |
| Tr51 | (6) | AAUCACAGGAAUCAACUUCUAUUCCCGCCC | New | 0.06 | 143 |
| Tr67 |  | AAUCACAGGAAUCGACUUUUAUUCCUGCCC | New | ND | 144 |
| Tr17 |  | GC GGCUCGAUGUCGUCUUAUCCCUUUGCCC | 8-17 | 3.0 | 145 |
| Tr27 |  | UC GGCUCGUUGUCGUCUUAUCCCUUUGCCC | New | ND | 146 |
| Tr18 |  | GCUGGCUCGAUGUCAGGUUAUCCCUUUGCCC | New | ND | 147 |
| Tr4 | (4,2)[d] | GUGACUCAAAAUGGUGAUCCUCGUUUCCGC | 8-126 | 1.4 | 148 |
| Tr31 | (2) | UGAAUUCCUCUGGCUGAAAAUGACUUGUGC | 8-113 | 9.2 | 149 |
| Tr15 |  | GUUUGAGUGACGAUCGUCUUGUCCCAUGUG | 11-208 | 8.8 | 150 |
| Tr1 |  | AUUGAUUCACUGCAUCCUUGACUCUUCCCC | New | 7.3 | 151 |
| Tr5 |  | CAGACGACUCGCCCGAAGGACGAUGCGG | New | 28 | 152 |
| Tr14 |  | GAGUUAUAUUUCGUCACCCGUUCCUUUGCCC | New | 2.2 | 153 |

TABLE 5-continued

HGF truncate SELEX 30N sequences.

| Trunc Seq#[a] | # of hits | Sequence of random region (G)G-30N-CA | Identity to full-length | [b] $K_d$(nM) | SEQ. I No. |
|---|---|---|---|---|---|
| Tr59 | | ACAGUUUGUCUUCUAUAGCUCGUCGCCCC | New | 7.2 | 154 |
| Tr71 | | UCAGAAUGACUUUCAUAGCUCGCUUUCCCC | New | 7.7 | 155 |

[a]Tr1-36 and Tr37-72 clones are from series which were carried through 8 and 11 conventional rounds, respectively.
[b]Sequences indicated are identical to full length aptamers derived from series 8 or 11; NX22354 is a synthetic truncate based on boundary experiments, derived from sequence 8-102, shown here for comparative purposes.
[c]ND, not determined.
[d](4,2) refers to 4 occurrences in the first series and two in the second series.

TABLE 6

Invasion of A549 cells through Matrigel is inhibited by HGF aptamer NX22354.

| Sample | HGF 10 ng/ml | Inhibitor | Cells migrated |
|---|---|---|---|
| 1 | − | — | 40 |
| 2 | + | — | 240 |
| 3 | + | mAb[a], 1 g/ml | 120 |
| 4 | + | NX22354, 1 uM | 40 |
| 5 | + | NX22354, 0.2 uM | 25 |
| 6 | + | NX22354, 0.04 uM | 200 |

[a]Anti-HGF antibody was MAB294 from R&D Systems, Inc.

TABLE 7

Partially 2'-O-methyl substituted variants of NX22354.

| SEQUENCE | SEQ. ID. No. |
|---|---|
| NX22354 GGACGAUGCGGCGAGUGCCUGUUUAUGUCAUCGUCC (parent) *** ** * ** *** *  *  * * * * | 13 |

TABLE 7-continued

Partially 2'-O-methyl substituted variants of NX22354.

| SEQUENCE | SEQ. ID. No. |
|---|---|
| HGFOMe1 GGACGAUGCGGCGAGUGCCUGUUUAUGUCAUCGUCCg | 156 |
| HGFOMe2 GGACGAUGCGGCGAGUGCCUGUUUAUGUCAUCGUCCg | 157 |
| HGFOMe3 GGACGAUGCGGCGAGUGCCUGUUUAUGUCAUCGUCCg | 158 |
| HGFOMe4 GGACGAUGCGGCGAGUGCCUGUUUAUGUCAUCGUCCg | 159 |

Parent 36mer sequence of NX22354 (purines marked with asterisks). The substituted positions are indicated by underlines. The OMe1 sequence has five substitutions while the others have four. For technical reasons, a G residue was added at the 3'-end of each aptamer.

TABLE 9

40N7 sequences isolated from a plate SELEX on human c-met.

| Clone name: | (number of isolates). | Sequence[a] | SEQ ID NO: |
|---|---|---|---|
| FAMILY 1: | | | |
| 7C -1: | (2) | UUUGACUAUGUCUGACGGGUCUGUGGUCAAUUCCGCCCC | 160 |
| FAMILY 2 | | | |
| 7C -4: | (1) | AUCCGUGUUGAUGUCCAUAUAACCUUAUCCCGUCGCUCCC | 161 |
| 7C -5: | (1) | GUGUUGACUUCUAGCCAGAAUAACAUUUUGUACCCCUCCC | 162 |
| FAMILY 3 | | | |
| 7C -2: | (1) | UCGUUGAGCUUUUGAUAGGGCUUGUUCUUCGAGCGUCCC | 163 |
| 7C-23: | (1) | UGAUCUUGGGGUUUGAUCGUAAUUACUUCACCCUCCGUCCC | 164 |
| FAMILY 4 | | | |
| 7C-26: | (2) | CUCCUUUUCCGCUAAACAAGACCACUUUGAGCCCUGCCCC | 165 |

TABLE 9-continued

40N7 sequences isolated from a plate SELEX on human c-met.

| Clone name: | (number of isolates). Sequence[a] | SEQ ID NO: |
|---|---|---|
| FAMILY 5 | | |
| 7C-25: | (1) CCACCUCGUUACGUACUGAUUUUGGCAUCGCAGUUUGCCC | 166 |
| 7C-27: | (1) GGGCACCUCGAUACGUACUGAUUUUGAAUAUCAGUUAGCCCC | 167 |
| OTHERS | | |
| 7C-21: | (1) CGAUUCGUCGUAUAGAAAUGAUUUGAAUGCACCUCCUCCC | 168 |
| 7C-24: | (1) UGUGUUUGUGUGUUGUGUUUGUUAUUCCUGUUUGUGUCCU | 169 |
| 7C-32: | (1) UCGGUCGUAAAAAAUCGUUGGUGUCUAUCUAUUGUUCUCCC | 170 |
| Presumed IgG₁ aptamers | | |
| 7C -3: | (1) UGCUCCAGAGGAACCAUCGUUUACUUCAUUUAUUCGCCC | 171 |
| 7C-22: | (1) UGCUCCUUAGGAACCAUCGUCUAUAUCCCAUUCUGACUGCC | 172 |
| 7C-30: | (1) UGCUCCUCAGGAACCAUCGUUUUUCCCAUGUCCUUCUGCC | 173 |
| 7C-29: | (3) UGCUCCUUGGAUUACCAAGGAACCAUUUUCCUCUACCCCC | 174 |

[a]N7 fixed sequences are not shown. (5'-GGGAGGACGAUGCGG-N-CAGACGACUCGCCCGA-3')(SEQ ID NO:2)

TABLE 10

30N8 sequences isolated from a plate SELEX on human c-met.

| Clone name: | (number of isolates). Sequence[a] | SEQ. ID. NO: |
|---|---|---|
| FAMILY 1: | | |
| 7b-1: | (4) GUGCUCAUUACGAACUUGACCGAUGCCUA | 175 |
| 7b-9: | (1) GGUGCUCAUUACGAACUUGACCGAAGCCUA | 176 |
| 7b-18: | (1) GGUGCUCAUUACGAACUUGACCGAUGCCUA | 177 |
| 7b-3: | (1) AGUGCUCCAAUGAACUUUGCUCGCUGA | 178 |
| 7b-8: | (1) GGUGCUCCGUUUGGAACUUGAUCGGUAGGA | 179 |
| 7b-7: | (1) GUGCUCAUUCAGAACUUGACGUAUAACCA | 180 |
| 7b-14: | (1) GGUGCUCCUUAGGAACUUGACCGUCCGCCA | 181 |
| 7b-16: | (1) GUGGUGCUCCACUAACCAAGUGGAACCUUG | 182 |
| consensus: | GUGCUC-UU--GAACUUGACCG | 183 |
| OTHERS: | | |
| 7b-10: | (1) ACGAUAAGUGGGAGUGAGUAAGUUUGAGUA | 184 |
| 7b-12: | (1) CCUAGACCCCCAGGUUCCUCCCCACUAGUC | 185 |

[a]N8 fixed sequences are not shown. (5'-GGGAGAUAAGAAUAAACGCUCAA-N-UUCGACAGGAGGCUCACAACAGGC-3')(SEQ ID NO:6)

What is claimed is:

1. A method for the isolation of nucleic acid ligands to HGF, comprising:

a) preparing a candidate mixture of nucleic acids;

b) contacting the candidate mixture of nucleic acids with HGF, wherein nucleic acids having an increased affinity to HGF relative to the candidate mixture may be partitioned from the remainder of the candidate mixture;

c) partitioning the increased affinity nucleic acids from the remainder of the candidate mixture;

d) amplifying the increased affinity nucleic acids to yield a mixture of nucleic acids enriched for nucleic acids with relatively higher affinity and specificity for binding to HGF, whereby a nucleic acid ligand of HGF may be identified.

2. The method of claim 1 wherein said candidate mixture comprises single-stranded nucleic acids.

3. The method of claim 2 wherein said single-stranded nucleic acids comprise ribonucleic acids.

* * * * *

SEQUENCE LISTING

<160> NUMBER OF SEQ ID NOS: 192

<210> SEQ ID NO 1
<211> LENGTH: 78
<212> TYPE: DNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(78)
<223> OTHER INFORMATION: N at positions 33-62 is any base.

<400> SEQUENCE: 1
taatacgact cactataggg augacgaugc ggnnnnnnnn nnnnnnnnnn nnnnnnnnn    60 nncagacgac ucgcccga                                                    78

<210> SEQ ID NO 2
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(61)
<223> OTHER INFORMATION: All pyrimidines are 2'F.
<220> FEATURE:
<221> NAME/KEY: modified_base
<222> LOCATION: (1)..(61)
<223> OTHER INFORMATION: N at positions 16-45 is any base.

<400> SEQUENCE: 2
gggaggacga ugcggnnnnn nnnnnnnnnn nnnnnnnnnn nnnnncagac gacucgcccg     60
a                                                                      61

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 3
taatacgact cactataggg augacgaugc gg                                    32

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 4
tcgggcgagt cgtctg                                                      16

<210> SEQ ID NO 5
<211> LENGTH: 94
<212> TYPE: DNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(94)
<223> OTHER INFORMATION: N at positions 41-70 is any base.

<400> SEQUENCE: 5
taatacgact cactataggg agacaagaat aaacgctcaa nnnnnnnnnn nnnnnnnnnn     60
nnnnnnnnnn ttcgacagga ggctcacaac aggc                                  94

<210> SEQ ID NO 6
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence

```
<220> FEATURE:
<221> NAME/KEY: modified_base
<222> LOCATION: (1)..(77)
<223> OTHER INFORMATION: All pyrimidines are 2'F.
<220> FEATURE:
<221> NAME/KEY: modified_base
<222> LOCATION: (1)..(77)
<223> OTHER INFORMATION: N at positions 24-53 is any base.

<400> SEQUENCE: 6
gggagauaag aauaaacgcu caannnnnnn nnnnnnnnnn nnnnnnnnnn nnnuucgaca      60
ggaggcucac aacaggc                                                    77

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 7
taatacgact cactataggg agacaa                                          26

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 8
gcctgttgtg agcctcctgt cgaa                                            24

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(15)
<223> OTHER INFORMATION: Purines and pyrimidines are 2'OMe; purines and
      pyrimidines at postions 1-11 are RNA; purines and
      pyrimidines at positions 12-15 are DNA.

<400> SEQUENCE: 9
cccuccugcu acgcc                                                      15

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(16)
<223> OTHER INFORMATION: Purines and pyrimidines are 2'OMe; purines and
      pyrimidines at positons 1-4 are DNA; purines and
      pyrimidines at positions 5-16 are RNA.

<400> SEQUENCE: 10
gtctgcugag cgggcu                                                     16
```

<210> SEQ ID NO 11
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(34)
<223> OTHER INFORMATION: All pyrimidines are 2'F.
<220> FEATURE:
<221> NAME/KEY: modified_base
<222> LOCATION: (1)..(34)
<223> OTHER INFORMATION: N at positions 3-32 is any base.

<400> SEQUENCE: 11
ggnnnnnnnn nnnnnnnnnn nnnnnnnnnn nnca                                    34

<210> SEQ ID NO 12
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(61)
<223> OTHER INFORMATION: All pyrimidines are 2'F.

<400> SEQUENCE: 12
gggaggacga ugcggcgagu gccuguuuau gucaucgucc gucgucagac gacucgcccg         60
a                                                                        61

<210> SEQ ID NO 13
<211> LENGTH: 36
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(36)
<223> OTHER INFORMATION: All pyrimidines are 2'F.

<400> SEQUENCE: 13
ggacgaugcg gcgagugccu guuuauguca ucgucc                                  36

<210> SEQ ID NO 14
<211> LENGTH: 28
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(28)
<223> OTHER INFORMATION: All pyrimidines are 2'F.

<400> SEQUENCE: 14
gacgaugcgg cgagugccug uuuauguc                                           28

<210> SEQ ID NO 15
<211> LENGTH: 88
<212> TYPE: DNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(88)
<223> OTHER INFORMATION: N at positions 33-72 is any base.

<400> SEQUENCE: 15
taatacgact cactataggg augacgaugc ggnnnnnnnn nnnnnnnnnn nnnnnnnnnn      60
nnnnnnnnnn nncagacgac ucgcccga                                        88

<210> SEQ ID NO 16
<211> LENGTH: 28
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(28)
<223> OTHER INFORMATION: All pyrimidines are 2'F.

<400> SEQUENCE: 16
ggacgaugcg ggcggcucga ugucgucu                                        28

<210> SEQ ID NO 17
<211> LENGTH: 38
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(38)
<223> OTHER INFORMATION: All pyrimidines are 2'F.

<400> SEQUENCE: 17
gggaggacga ugcgggcggc ucgaugucgu cuuauccc                             38

<210> SEQ ID NO 18
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 18
gggaggacga ugcggcggug ugaaccuguu uauguccgcg uacccagac gacucgcccg       60 a                                                                     61

<210> SEQ ID NO 19
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 19
gggaggacga ugcggcggug uggaccuguu uauguccgcg uacccagac gacucgcccg    60 a                                                                   61

<210> SEQ ID NO 20
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 20
gggaggacga ugcggaguga uccuauuuau gacaucgcgg gcugccagac gacucgcccg    60
a                                                                   61

<210> SEQ ID NO 21
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 21
gggaggacga ugcggguguga accuguuuau gucaucuuuu gucgucagac gacucgcccg    60
a                                                                   61

<210> SEQ ID NO 22
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 22
gggaggacga ugcgguguga accuauuuau gccaucucga gugcccagac gacucgcccg    60
a                                                                   61

<210> SEQ ID NO 23
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 23
gggaggacga ugcggcguga gccuauuuau gucaucaugu cuguccagac gacucgcccg    60
a                                                                   61

<210> SEQ ID NO 24
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 24
gggaggacga ugcggcgaga gccuauuuau gucaucaugc cugugcagac gacucgcccg    60
a                                                                   61

<210> SEQ ID NO 25
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 25
gggaggacga ugcggcggga gccuuuuuau gucaucaugu cugugcagac gacucgcccg    60
a                                                                   61

<210> SEQ ID NO 26
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 26
gggaggacga ugcggcguga gccuauuuau gucaucaugu cugugcagac gacucgcccg    60
a                                                                   61

<210> SEQ ID NO 27
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 27
gggaggacga ugcggcgcga gccuauuuau gucaucaugu cugugcagac gacucgcccg    60
a                                                                   61

<210> SEQ ID NO 28
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 28
gggaggacga ugcggcguga gccuauuuau gucaucaugu cuggucagac gacucgcccg    60
a                                                                  61

<210> SEQ ID NO 29
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 29
gggaggacga ugcggcguga gccuauuuac gucaucaugu cugugcagac gacucgcccg    60
a                                                                  61

<210> SEQ ID NO 30
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 30
gggaggacga ugcgguguga accuauuuau gccauuaugu cugugcagac gacucgcccg    60
a                                                                  61

<210> SEQ ID NO 31
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 31
gggaggacga ugcggcguga gccuauuuau gucaucaagu cugugcagac gacucgcccg    60
a                                                                  61

<210> SEQ ID NO 32

```
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 32
gggaggacga ugcggcguga gccuguuuau gaccucgucc auggccagac gacucgcccg    60
a                                                                   61

<210> SEQ ID NO 33
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 33
gggaggacga ugcggcguga gccuauuuau gacauguccc ucgagcagac gacucgcccg    60
a                                                                   61

<210> SEQ ID NO 34
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 34
gggaggacga ugcggcguga gccuguauau gucauuguuc uccggcagac gacucgcccg    60
a                                                                   61

<210> SEQ ID NO 35
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 35
gggaggacga ugcggugagu accuguuuau gucaccacuu uccccagac gacucgcccg     60 a                                                                   61

<210> SEQ ID NO 36
<211> LENGTH: 58
<212> TYPE: RNA
<213> ORGANISM: Artificial Sequence
```

```
<220> FEATURE:
<223> OTHER INFORMATION: Description of Artificial Sequence: Synthetic
      Sequence
<220> FEATURE:
<221> NAME/KEY: modified_base
<222> LOCATION: (1)..(57)
<223> OTHER INFORMATION: All pyrimidines are 2'F.

<400> SEQUENCE: 36
gggaggacga ugcggugauu accauuaug ucucgcccuc uccagacgac ucgcccga         58

<210> SEQ ID NO 37
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 37
gggaggacga ugcggugauu accauuuau gucaugcucc uccccagac gacucgcccg        60
a                                                                     61

<210> SEQ ID NO 38
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 38
gggaggacga ugcggugaua accuguuuau gccaucgugc ugggccagac gacucgcccg      60
a                                                                     61

<210> SEQ ID NO 39
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 39
gggaggacga ugcggugaua accuguuuau gucaucgugc ugggccagac gacucgcccg      60
a                                                                     61

<210> SEQ ID NO 40
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
```

```
<222> LOCATION: (1)..(60)
<223> OTHER INFORMATION: All pyrimidines are 2'F.

<400> SEQUENCE: 40
gggaggacga ugcggugaga accuauuuau gucaucgugu cuggccagac gacucgcccg    60
a                                                                   61

<210> SEQ ID NO 41
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 41
gggaggacga ugcggugaua accuauuuau gacgucgugg cucccagac gacucgcccg     60 a                                                                   61

<210> SEQ ID NO 42
<211> LENGTH: 60
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(59)
<223> OTHER INFORMATION: All pyrimidines are 2'F.

<400> SEQUENCE: 42
gggaggacga ugcgguggga accuauuuau gucauccg ucccagacg acucgccga        60

<210> SEQ ID NO 43
<211> LENGTH: 59
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(58)
<223> OTHER INFORMATION: All pyrimidines are 2'F.

<400> SEQUENCE: 43
gggaggacga ugcggcgaug augccuguuu augucgaugu ccccgggag acgaugcgg      59

<210> SEQ ID NO 44
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 44
gggaggacga ugcggcgaua gccuauuuau gaccucgucc ccgugcagac gacucgcccg    60
```

<210> SEQ ID NO 45
<211> LENGTH: 61
<212> TYPE: RNA
<213> ORGANISM: Artificial Sequence
<220> FEATURE:
<223> OTHER INFORMATION: Description of Artificial Sequence: Synthetic Sequence
<220> FEATURE:
<221> NAME/KEY: modified_base
<222> LOCATION: (1)..(60)
<223> OTHER INFORMATION: All pyrimidines are 2'F.

<400> SEQUENCE: 45
gggaggacga ugcggcguga gccuauuuau gacaucguuc uuggccagac gacucgcccg    60
a                                                                  61

<210> SEQ ID NO 46
<211> LENGTH: 61
<212> TYPE: RNA
<213> ORGANISM: Artificial Sequence
<220> FEATURE:
<223> OTHER INFORMATION: Description of Artificial Sequence: Synthetic Sequence
<220> FEATURE:
<221> NAME/KEY: modified_base
<222> LOCATION: (1)..(60)
<223> OTHER INFORMATION: All pyrimidines are 2'F.

<400> SEQUENCE: 46
gggaggacga ugcggcguga gccuaucuau gucaucgugu gugcccagac gacucgcccg    60
a                                                                  61

<210> SEQ ID NO 47
<211> LENGTH: 60
<212> TYPE: RNA
<213> ORGANISM: Artificial Sequence
<220> FEATURE:
<223> OTHER INFORMATION: Description of Artificial Sequence: Synthetic Sequence
<220> FEATURE:
<221> NAME/KEY: modified_base
<222> LOCATION: (1)..(59)
<223> OTHER INFORMATION: All pyrimidines are 2'F.

<400> SEQUENCE: 47
gggaggacga ugcggugagu acuauuuaug ucgucguucg ugcccagacg acucgcccga    60

<210> SEQ ID NO 48
<211> LENGTH: 61
<212> TYPE: RNA
<213> ORGANISM: Artificial Sequence
<220> FEATURE:
<223> OTHER INFORMATION: Description of Artificial Sequence: Synthetic Sequence
<220> FEATURE:
<221> NAME/KEY: modified_base
<222> LOCATION: (1)..(60)
<223> OTHER INFORMATION: All pyrimidines are 2'F.

<400> SEQUENCE: 48
gggaggacga ugcggcguga gccuuccaau gacgucgucc uuggccagac gacucgcccg    60
a                                                                  61

<210> SEQ ID NO 49
<211> LENGTH: 61

```
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 49
gggaggacga ugcgggcgac ucaaucugaa ucgucuuguc ccgugcagac gacucgcccg     60
a                                                                   61

<210> SEQ ID NO 50
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 50
gggaggacga ugcggucagc ggcgcgagcc uguuuauguc ugcugcagac gacucgcccg     60
a                                                                   61

<210> SEQ ID NO 51
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(56)
<223> OTHER INFORMATION: All pyrimidines are 2'F.

<400> SEQUENCE: 51
gggaggacga ugcggcguga gccuauuuau gucaucgucu gcagacgacu cgcccga        57

<210> SEQ ID NO 52
<211> LENGTH: 60
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(59)
<223> OTHER INFORMATION: All pyrimidines are 2'F.

<400> SEQUENCE: 52
gggaggacga ugcggucagu augacuuuua uagcacguuc gccccagacg acucgccga      60

<210> SEQ ID NO 53
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
```

```
<222> LOCATION: (1)..(60)
<223> OTHER INFORMATION: All pyrimidines are 2'F.

<400> SEQUENCE: 53
gggaggacga ugcggacagg uagucuucua uagcacuucc uccccagac gacucgcccg    60 a                                                                  61

<210> SEQ ID NO 54
<211> LENGTH: 60
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(59)
<223> OTHER INFORMATION: All pyrimidines are 2'F.

<400> SEQUENCE: 54
gggaggacga ugcggucaga augacuuuca uagcacgcuu uccccagacg acucgcccga   60

<210> SEQ ID NO 55
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 55
gggaggacga ugcggacaua agucuucuau agcucguccu uugugcagac gacucgcccg   60
a                                                                  61

<210> SEQ ID NO 56
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 56
gggaggacga ugcggucagu auggcuucua uagcucguuc cucggcagac gacucgcccg   60
a                                                                  61

<210> SEQ ID NO 57
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 57
```
gggaggacga ugcgggugac ucaaaauggu gauccucguu uccgccagac gacucgcccg    60
a                                                                   61

<210> SEQ ID NO 58
<211> LENGTH: 62
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(61)
<223> OTHER INFORMATION: All pyrimidines are 2'F.

<400> SEQUENCE: 58
gggaggacga ugcgggugac ucaaaauggu gauccucgau uuccgccaga cgacucgccc    60
ga                                                                  62

<210> SEQ ID NO 59
<211> LENGTH: 62
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(61)
<223> OTHER INFORMATION: All pyrimidines are 2'F.

<400> SEQUENCE: 59
gggaggacga ugcgggugac ucaaaauggu gauccucgau ugccgccaga cgacucgccc    60
ga                                                                  62

<210> SEQ ID NO 60
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 60
gggaggacga ugcgggccga aaauucgucg acaucucccu gucugcagac gacucgcccg    60
a                                                                   61

<210> SEQ ID NO 61
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 61
gggaggacga ugcggggcga cuuuccucca auucucaccu cugcacagac gacucgcccg    60
a                                                                   61

<210> SEQ ID NO 62
<211> LENGTH: 61
<212> TYPE: RNA
<213> ORGANISM: Artificial Sequence
<220> FEATURE:
<223> OTHER INFORMATION: Description of Artificial Sequence: Synthetic Sequence
<220> FEATURE:
<221> NAME/KEY: modified_base
<222> LOCATION: (1)..(60)
<223> OTHER INFORMATION: All pyrimidines are 2'F.

<400> SEQUENCE: 62
gggaggacga ugcgggccau ucgaucgauu cuccgccgga ucgugcagac gacucgcccg    60
a                                                                   61

<210> SEQ ID NO 63
<211> LENGTH: 62
<212> TYPE: RNA
<213> ORGANISM: Artificial Sequence
<220> FEATURE:
<223> OTHER INFORMATION: Description of Artificial Sequence: Synthetic Sequence
<220> FEATURE:
<221> NAME/KEY: modified_base
<222> LOCATION: (1)..(61)
<223> OTHER INFORMATION: All pyrimidines are 2'F.

<400> SEQUENCE: 63
gggaggacga ugcggauccc gcgaccaggg cguuucuucc ucgucccaga cgacucgccc    60
ga                                                                  62

<210> SEQ ID NO 64
<211> LENGTH: 61
<212> TYPE: RNA
<213> ORGANISM: Artificial Sequence
<220> FEATURE:
<223> OTHER INFORMATION: Description of Artificial Sequence: Synthetic Sequence
<220> FEATURE:
<221> NAME/KEY: modified_base
<222> LOCATION: (1)..(60)
<223> OTHER INFORMATION: All pyrimidines are 2'F.

<400> SEQUENCE: 64
gggaggacga ugcggucccg aauuuaagug cguuccucc gcguccagac gacucgcccg     60
a                                                                   61

<210> SEQ ID NO 65
<211> LENGTH: 61
<212> TYPE: RNA
<213> ORGANISM: Artificial Sequence
<220> FEATURE:
<223> OTHER INFORMATION: Description of Artificial Sequence: Synthetic Sequence
<220> FEATURE:
<221> NAME/KEY: modified_base
<222> LOCATION: (1)..(60)
<223> OTHER INFORMATION: All pyrimidines are 2'F.

<400> SEQUENCE: 65
gggaggacga ugcgguccca agauucaggg cguuucuucc ucguccagac gacucgcccg    60
a                                                                   61

<210> SEQ ID NO 66

```
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 66
gggaggacga ugcgguccccg aguuugaggg cguuucuucu ucguccagac gacucgcccg    60
a                                                                     61

<210> SEQ ID NO 67
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 67
gggaggacga ugcgguccca guuucagggg cgauuccucu ucguccagac gacucgcccg    60
a                                                                     61

<210> SEQ ID NO 68
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 68
gggaggacga ugcgggcggc ucgaugucgu cuuaucccuu ugccccagac gacucgcccg    60
a                                                                     61

<210> SEQ ID NO 69
<211> LENGTH: 64
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(63)
<223> OTHER INFORMATION: All pyrimindines are 2'F.

<400> SEQUENCE: 69
gggaggacga ugcgggcggg cucgaugucg ucuuauccccc uuugccccca gacgacucgc    60
ccga                                                                  64

<210> SEQ ID NO 70
<211> LENGTH: 61
<212> TYPE: RNA
<213> ORGANISM: Artificial Sequence
```

```
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 70
gggaggacga ugcggccggc ucgaugucgu cuuacgccuu ugccccagac gacucgcccg    60
a                                                                   61

<210> SEQ ID NO 71
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimindines are 2'F.

<400> SEQUENCE: 71
gggaggacga ugcggguuug agugaugucg ucuugucccg ccugccagac gacucgcccg    60
a                                                                   61

<210> SEQ ID NO 72
<211> LENGTH: 60
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(59)
<223> OTHER INFORMATION: All pyrimidines are 2'F.

<400> SEQUENCE: 72
gggaggacga ugcggguuag aguuuugucg ucuuguccca ugugcagacg acucgcccga    60

<210> SEQ ID NO 73
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 73
gggaggacga ugcgggcuug agucuuugau cgucuuaucc cucgucagac gacucgcccg    60
a                                                                   61

<210> SEQ ID NO 74
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
```

```
<222> LOCATION: (1)..(60)
<223> OTHER INFORMATION: All pyrimidines are 2'F.

<400> SEQUENCE: 74
gggaggacga ugcggguuug agugacgauc gucuugucccc augugcagac gacucgcccg    60
a                                                                    61

<210> SEQ ID NO 75
<211> LENGTH: 59
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(58)
<223> OTHER INFORMATION: All pyrimidines are 2'F.

<400> SEQUENCE: 75
gggaggacga ugcgggguuug aguuaaacau cgguuuucuc cugcagacga cucgcccga     59

<210> SEQ ID NO 76
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 76
gggaggacga ugcgggacgc guugauucau cgucuuaucc ugcugcagac gacucgcccg    60
a                                                                    61

<210> SEQ ID NO 77
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 77
gggaggacga ugcgggguuug ggucuugauc ucgucuuguc ccgugcagac gacucgcccg    60
a                                                                    61

<210> SEQ ID NO 78
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 78
```
gggaggacga ugcggguuga uaggagucau caucgucuug uccgccagac gacucgcccg    60
a    61

<210> SEQ ID NO 79
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 79
gggaggacga ugcgguagu gaguuuucau ugucuugucc ccgugcagac gacucgcccg    60
a    61

<210> SEQ ID NO 80
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 80
gggaggacga ugcggugagu cauaguguug aucgucguau cccgucagac gacucgcccg    60
a    61

<210> SEQ ID NO 81
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 81
gggaggacga ugcgggugga gucaaaucgu cuugucccuu guccucagac gacucgcccg    60
a    61

<210> SEQ ID NO 82
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 82
gggaggacga ugcggguuug aguucugaca cgucuugucc caugccagac gacucgcccg    60
a    61

<210> SEQ ID NO 83
<211> LENGTH: 64
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(63)
<223> OTHER INFORMATION: All pyrimidines are 2'F.

<400> SEQUENCE: 83
gggaggacga ugcggguuag agcgugacag ucgucuuauc ccggucaca gacgacucgc      60 ccga                                                                  64

<210> SEQ ID NO 84
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 84
gggaggacga ugcggugaau uccucuggcu gaaaaugacu ugugccagac gacucgcccg      60
a                                                                     61

<210> SEQ ID NO 85
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 85
gggaggacga ugcggugaau uccuuuggcu gaaaaugacu ugugccagac gacucgcccg      60
a                                                                     61

<210> SEQ ID NO 86
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 86
gggaggacga ugcgggcaga gcgaaaaucg ucuugucccc gacgccagac gacucgcccg      60
a                                                                     61

<210> SEQ ID NO 87

```
<211> LENGTH: 60
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(59)
<223> OTHER INFORMATION: All pyrimidines are 2'F.

<400> SEQUENCE: 87
gggaggacga ugcgggugac ucaaaauggu gauccucguu ucgccagacg acucgcccga    60

<210> SEQ ID NO 88
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 88
gggaggacga ugcggaggac uaaucccuaa ggaauagcuu gcccgcagac gacucgcccg    60
a                                                                    61

<210> SEQ ID NO 89
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 89
gggaggacga ugcggucgag cuucugaguu aaacuggggc cuccucagac gacucgcccg    60
a                                                                    61

<210> SEQ ID NO 90
<211> LENGTH: 63
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(62)
<223> OTHER INFORMATION: All pyrimidines are 2'F.

<400> SEQUENCE: 90
gggaggacga ugcggguccc cgaauuuaaa gugcguuuuc cuccgggcag acgacucgcc    60
cga                                                                  63

<210> SEQ ID NO 91
<211> LENGTH: 62
<212> TYPE: RNA
<213> ORGANISM: Artificial Sequence
<220> FEATURE:
<223> OTHER INFORMATION: Description of Artificial Sequence: Synthetic
```

```
            Sequence
<220> FEATURE:
<221> NAME/KEY: modified_base
<222> LOCATION: (1)..(61)
<223> OTHER INFORMATION: All pyrimidines are 2'F.

<400> SEQUENCE: 91
gggaggacga ugcggggutu uucuuuucuu guucucuucu uucccccaga cgacucgccc      60
ga                                                                    62

<210> SEQ ID NO 92
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 92
gggaggacga ugcggacagc ggcgacuagc cuguucaugc cugcccagac gacucgcccg      60
a                                                                     61

<210> SEQ ID NO 93
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(60)
<223> OTHER INFORMATION: All pyrimidines are 2'F.

<400> SEQUENCE: 93
gggaggacga ugcggguucu guguguccac guucuuaccc cugugcagac gacucgcccg      60
a                                                                     61

<210> SEQ ID NO 94
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 94
gggagauaag aauaaacgcu caaccuguuc ugaacgcaaa auggcguggu ggcuucgaca      60
ggaggcucac aacaggc                                                    77

<210> SEQ ID NO 95
<211> LENGTH: 76
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
```

<222> LOCATION: (1)..(76)
<223> OTHER INFORMATION: All pyrimidines are 2'F.

<400> SEQUENCE: 95
gggagauaag aauaaacgcu caaugucguu aguuuauuga caaggcccga aguucgacag    60
gaggcucaca acaggc                                                   76

<210> SEQ ID NO 96
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 96
gggagauaag aauaaacgcu caaucuuauu guguccagcu ucucccugca ggcuucgaca    60
ggaggcucac aacaggc                                                  77

<210> SEQ ID NO 97
<211> LENGTH: 75
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(75)
<223> OTHER INFORMATION: All pyrimidines are 2'F.

<400> SEQUENCE: 97
gggagauaag aauaaacgcu caauguggca cuguugucca caagggccuc auucgacagg    60
aggcucacaa caggc                                                    75

<210> SEQ ID NO 98
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 98
gggagauaag aauaaacgcu caauugacaa gguaccuguu gccuggcguu ucuuucgaca    60
ggaggcucac aacaggc                                                  77

<210> SEQ ID NO 99
<211> LENGTH: 76
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(76)
<223> OTHER INFORMATION: All pyrimidines are 2'F.

<400> SEQUENCE: 99
gggagauaag aauaaacgcu caaaguuagg cuuuaaagca cgauaaucag cauucgacag    60
gaggcucaca acaggc    76

<210> SEQ ID NO 100
<211> LENGTH: 78
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(78)
<223> OTHER INFORMATION: All pyrimidines are 2'F.

<400> SEQUENCE: 100
gggagauaag aauaaacgcu caagucaaga ggaaaugaca cggcuccacu uuuauucgac    60
aggaggcuca caacaggc    78

<210> SEQ ID NO 101
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 101
gggagauaag aauaaacgcu caagccugag uuaaacauga cgguuuguga cccuucgaca    60
ggaggcucac aacaggc    77

<210> SEQ ID NO 102
<211> LENGTH: 81
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(81)
<223> OTHER INFORMATION: All pyrimidines are 2'F.

<400> SEQUENCE: 102
gggagauaag aauaaacgcu caagccugag uuaaacauga cggguuuugu gaccccuuuc    60
gacaggaggc ucacaacagg c    81

<210> SEQ ID NO 103
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 103
gggagauaag aauaaacgcu caagucugag uuggacacaa cgcauugaga cccuucgaca    60
ggaggcucac aacaggc    77

<210> SEQ ID NO 104
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 104
gggagauaag aauaaacgcu caagucugag uuggucacaa cgcauugaga cccuucgaca    60
ggaggcucac aacaggc    77

<210> SEQ ID NO 105
<211> LENGTH: 76
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(76)
<223> OTHER INFORMATION: All pyrimidines are 2'F.

<400> SEQUENCE: 105
gggagauaag aauaaacgcu caagucugag uccguagggc gauuuguguc ccuucgacag    60
gaggcucaca acaggc    76

<210> SEQ ID NO 106
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 106
gggagauaag aauaaacgcu caaugccuua agagcggaac ucccugaccc accuucgaca    60
ggaggcucac aacaggc    77

<210> SEQ ID NO 107
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 107
gggagauaag aauaaacgcu caagaucugu uggcgugucu acccgacccu ccuucgaca    60 ggaggcucac aacaggc    77

<210> SEQ ID NO 108
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 108
gggagauaag aauaaacgcu caagaucugu uggcgugucu acccgacccu ccuuucgaca    60
ggaggcucac aacaggc                                                  77

<210> SEQ ID NO 109
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 109
gggagauaag aauaaacgcu caacguuagc aucugaacga ugcccagccu caauucgaca    60
ggaggcucac aacaggc                                                  77

<210> SEQ ID NO 110
<211> LENGTH: 76
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(76)
<223> OTHER INFORMATION: All pyrimidines are 2'F.

<400> SEQUENCE: 110
gggagauaag aauaaacgcu caaguuagac ucaacaugag ucccagccuc aauucgacag    60
gaggcucaca acaggc                                                   76

<210> SEQ ID NO 111
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 111
gggagauaag aauaaacgcu caaucuguug gcgucguucu ccugacccuc ucuuucgaca    60
ggaggcucac aacaggc                                                  77

<210> SEQ ID NO 112
<211> LENGTH: 77

```
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 112
gggagauaag aauaaacgcu caagaguucc cuguugacuc gcucuccuga cccuucgaca      60
ggaggcucac aacaggc                                                    77

<210> SEQ ID NO 113
<211> LENGTH: 78
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(78)
<223> OTHER INFORMATION: All pyrimidines are 2'F.

<400> SEQUENCE: 113
gggagauaag aauaaacgcu caauacagcg uguuggucccc ggacggggac uuauuucgac     60
aggaggcuca caacaggc                                                   78

<210> SEQ ID NO 114
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 114
gggagauaag aauaaacgcu caacgccugg accguuuguu uaucccgua gucuucgaca       60 ggaggcucac aacaggc                                                    77

<210> SEQ ID NO 115
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 115
gggagauaag aauaaacgcu caacgugauu ccuaccauca gguaccuauc uuguucgaca      60
ggaggcucac aacaggc                                                    77

<210> SEQ ID NO 116
<211> LENGTH: 77
<212> TYPE: RNA
<213> ORGANISM: Artificial Sequence
<220> FEATURE:
```

```
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 116
gggagauaag aauaaacgcu caaagugaug ugagagcgug ccucuagucg guguucgaca      60
ggaggcucac aacaggc                                                    77

<210> SEQ ID NO 117
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 117
gggagauaag aauaaacgcu caacgagccu ccuaccguuu agguaccauc uuguucgaca      60
ggaggcucac aacaggc                                                    77

<210> SEQ ID NO 118
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 118
gggagauaag aauaaacgcu caauuagccu ccgaccguaa gguccuuuuc uuguucgaca      60
ggaggcucac aacaggc                                                    77

<210> SEQ ID NO 119
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 119
gggagauaag aauaaacgcu caaggccucc aaccgcuaaa gguuccauuc uuguucgaca      60
ggaggcucac aacaggc                                                    77

<210> SEQ ID NO 120
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
```

<221> NAME/KEY: modified_base
<222> LOCATION: (1)..(77)
<223> OTHER INFORMATION: All pyrimidines are 2'F.

<400> SEQUENCE: 120
gggagauaag aauaaacgcu caacccgacc uccuguaacu gguugaggca cuauucgaca    60
ggaggcucac aacaggc                                                   77

<210> SEQ ID NO 121
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 121
gggagauaag aauaaacgcu caaggguucc ugauugaccc ugucucuaga cccuucgaca    60
ggaggcucac aacaggc                                                   77

<210> SEQ ID NO 122
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 122
gggagauaag aauaaacgcu caaggggagg cccuucagcc gucuccuuga cccuucgaca    60
ggaggcucac aacaggc                                                   77

<210> SEQ ID NO 123
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 123
gggagauaag aauaaacgcu caaugugaug ugagggcgug cuuccuaacg guguucgaca    60
ggaggcucac aacaggc                                                   77

<210> SEQ ID NO 124
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2'F.

```
<400> SEQUENCE: 124
gggagauaag aauaaacgcu caauucauua ugcaucgaac aguauaccac agguguucau      60
guguucgaca ggaggcucac aacaggc                                         87

<210> SEQ ID NO 125
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2'F.

<400> SEQUENCE: 125
gggagauaag aauaaacgcu caaauccaaa uucuggucau gaggcgcugc agauacugcu      60
gcguucgaca ggaggcucac aacaggc                                         87

<210> SEQ ID NO 126
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2'F.

<400> SEQUENCE: 126
gggagauaag aauaaacgcu caaucugcgg acggugaggu uaaguugcaa cgacugcuug      60
gcguucgaca ggaggcucac aacaggc                                         87

<210> SEQ ID NO 127
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2'F.

<400> SEQUENCE: 127
gggagauaag aauaaacgcu caacagaccg ugcaaacccc ccuuagaggg uuuugucauu      60
uacuucgaca ggaggcucac aacaggc                                         87

<210> SEQ ID NO 128
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2'F.

<400> SEQUENCE: 128
```

```
gggagauaag aauaaacgcu caaccuuagg gcucccaaaa aucgggcccg ucgggccgau    60
cacuucgaca ggaggcucac aacaggc                                      87
```

<210> SEQ ID NO 129
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2'F.

<400> SEQUENCE: 129

```
gggagauaag aauaaacgcu caacgcggga uucucugagg acgaggcacg uguggguaau    60
ucguucgaca ggaggcucac aacaggc                                      87
```

<210> SEQ ID NO 130
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2'F.

<400> SEQUENCE: 130

```
gggagauaag aauaaacgcu caaucgggcu uggaugugga cguguauuuc uagcugugua    60
cgcuucgaca ggaggcucac aacaggc                                      87
```

<210> SEQ ID NO 131
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2'F.

<400> SEQUENCE: 131

```
gggagauaag aauaaacgcu caauugdgguc gggacucgaa aggauuugau aggauacaug    60
aauuucgaca ggaggcucac aacaggc                                      87
```

<210> SEQ ID NO 132
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 132

```
cggugugaac cuguuuaugu ccgcguaccc                                   30
```

<210> SEQ ID NO 133
<211> LENGTH: 29
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(29)
<223> OTHER INFORMATION: All pyrimidines are 2'F.

<400> SEQUENCE: 133
ugggaaccua uuuaugucau cuccguccc                                      29

<210> SEQ ID NO 134
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 134
ugggaaccua uuuaugucau cgucugugcc                                     30

<210> SEQ ID NO 135
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 135
cgugagccua uuuaugucau caugucugug                                     30

<210> SEQ ID NO 136
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 136
ugugaaccug uuuaugccau cucgaguccc                                     30

<210> SEQ ID NO 137
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 137
ugugaaccua uuuaugccau cucgagugcc                                          30

<210> SEQ ID NO 138
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 138
ugauaaccua uuuaugacgu cguggcuccc                                          30

<210> SEQ ID NO 139
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 139
agugauccua uuuaugccgu cgcuucucgc                                          30

<210> SEQ ID NO 140
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 140
agagnuccua uuuaugacau cccaugcccc                                          30

<210> SEQ ID NO 141
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 141
ugaucaccug uuuaugccau cguucgggc                                           30

<210> SEQ ID NO 142
<211> LENGTH: 30
<212> TYPE: RNA
<213> ORGANISM: Artificial Sequence
<220> FEATURE:

```
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 142
ggugacccuu uuuaugacau cgcgucuggc                                    30

<210> SEQ ID NO 143
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 143
aaucacagga aucaacuucu auucccgccc                                    30

<210> SEQ ID NO 144
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimindines are 2'F.

<400> SEQUENCE: 144
aaucacagga aucgacuuuu auuccugccc                                    30

<210> SEQ ID NO 145
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimindines are 2'F.

<400> SEQUENCE: 145
gcggcucgau gucgucuuau cccuuugccc                                    30

<210> SEQ ID NO 146
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimindines are 2'F.

<400> SEQUENCE: 146
ucggcucguu gucgucuuau cccuuugccc                                    30
```

```
<210> SEQ ID NO 147
<211> LENGTH: 31
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(31)
<223> OTHER INFORMATION: All pyrimidines are 2'F.

<400> SEQUENCE: 147
gcuggcucga ugucagguua ucccuuugcc c                                    31

<210> SEQ ID NO 148
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 148
gugacucaaa auggugaucc ucguuuccgc                                      30

<210> SEQ ID NO 149
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 149
ugaauuccuc uggcugaaaa ugacuugugc                                      30

<210> SEQ ID NO 150
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 150
guuugaguga cgaucgucuu gucccaugug                                      30

<210> SEQ ID NO 151
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
```

<223> OTHER INFORMATION: All pyrimidines are 2'F.

<400> SEQUENCE: 151
auugauucac ugcauccuug acucuucccc                                    30

<210> SEQ ID NO 152
<211> LENGTH: 28
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(28)
<223> OTHER INFORMATION: All pyrimidines are 2'F.

<400> SEQUENCE: 152
cagacgacuc gcccgaagga cgaugcgg                                      28

<210> SEQ ID NO 153
<211> LENGTH: 31
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(31)
<223> OTHER INFORMATION: All pyrimidines are 2'F.

<400> SEQUENCE: 153
gaguuauauu ucgucacccg uuccuuugcc c                                  31

<210> SEQ ID NO 154
<211> LENGTH: 29
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(29)
<223> OTHER INFORMATION: All pyrimidines are 2'F.

<400> SEQUENCE: 154
acaguuuguc uucuauagcu cgucgcccc                                     29

<210> SEQ ID NO 155
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(30)
<223> OTHER INFORMATION: All pyrimidines are 2'F.

<400> SEQUENCE: 155
ucagaaugac uuucauagcu cgcuuucccc                                    30

<210> SEQ ID NO 156
<211> LENGTH: 37
<212> TYPE: RNA
<213> ORGANISM: Artificial Sequence

```
<220> FEATURE:
<223> OTHER INFORMATION: Description of Artificial Sequence: Synthetic
      Sequence
<220> FEATURE:
<221> NAME/KEY: modified_base
<222> LOCATION: (1)..(37)
<223> OTHER INFORMATION: All pyrimidines are 2'F.  Bases at positions
      1, 6, 13, 21, 33 are 2'OMe.

<400> SEQUENCE: 156
ggacgaugcg gcgagugccu guuuauguca ucguccg                            37

<210> SEQ ID NO 157
<211> LENGTH: 37
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(37)
<223> OTHER INFORMATION: All pyrimidines are 2'F.  Bases at positions
      2, 8, 14, 25 are 2'OMe.

<400> SEQUENCE: 157
ggacgaugcg gcgagugccu guuuauguca ucguccg                            37

<210> SEQ ID NO 158
<211> LENGTH: 37
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(37)
<223> OTHER INFORMATION: All pyrimidines are 2'F.  Bases at positions 3,
      10, 15 and 27 are 2'OMe.

<400> SEQUENCE: 158
ggacgaugcg gcgagugccu guuuauguca ucguccg                            37

<210> SEQ ID NO 159
<211> LENGTH: 37
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(37)
<223> OTHER INFORMATION: All pyrimidines are 2'F.   Bases at positions
      5, 11, 17, 30 are 2'OMe.

<400> SEQUENCE: 159
ggacgaugcg gcgagugccu guuuauguca ucguccg                            37

<210> SEQ ID NO 160
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2'F.
```

<400> SEQUENCE: 160
gggaggacga ugcgguuuga cuaugucuga cgggucugug gucaauuccg cccccagacg        60
acucgcccga        70

<210> SEQ ID NO 161
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(71)
<223> OTHER INFORMATION: All pyrimidines are 2'F.

<400> SEQUENCE: 161
gggaggacga ugcggauccg uguugauguc cauauaaccu uaucccgucg cuccccagac        60
gacucgcccg a        71

<210> SEQ ID NO 162
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(71)
<223> OTHER INFORMATION: All pyrimidines are 2'F.

<400> SEQUENCE: 162
gggaggacga ugcggguguu gacuucuagc cagaauaaca uuuguaccc cuccccagac        60 gacucgcccg a        71

<210> SEQ ID NO 163
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2'F.

<400> SEQUENCE: 163
gggaggacga ugcggucguu gagcuuuuga uagggcuugu ucuucgagcg uccccagacg        60
acucgcccga        70

<210> SEQ ID NO 164
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(71)
<223> OTHER INFORMATION: All pyrimidines are 2'F.

<400> SEQUENCE: 164
gggaggacga ugcggugauc uuggguuuga ucguaauuac uucacccucc gucccagac    60 gacucgcccg a    71

<210> SEQ ID NO 165
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(71)
<223> OTHER INFORMATION: All pyrimidines are 2'F.

<400> SEQUENCE: 165
gggaggacga ugcggcuccu uuuccgcuaa acaagaccac uuugagcccu gcccccagac    60
gacucgcccg a    71

<210> SEQ ID NO 166
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(71)
<223> OTHER INFORMATION: All pyrimidines are 2'F.

<400> SEQUENCE: 166
gggaggacga ugcggccacc ucguuacgua cugauuuugg caucgcaguu ugccccagac    60
gacucgcccg a    71

<210> SEQ ID NO 167
<211> LENGTH: 73
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(73)
<223> OTHER INFORMATION: All pyrimidines are 2'F.

<400> SEQUENCE: 167
gggaggacga ugcgggggca ccucgauacg uacugauuuu gaauaucagu uagcccccag    60
acgacucgcc cga    73

<210> SEQ ID NO 168
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(71)
<223> OTHER INFORMATION: All pyrimidines are 2'F.

<400> SEQUENCE: 168
gggaggacga ugcggcgauu cgucguauag aaaugauuug aaugcaccuc cucccagac    60 gacucgcccg a    71

<210> SEQ ID NO 169
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(71)
<223> OTHER INFORMATION: All pyrimidines are 2'F.

<400> SEQUENCE: 169
gggaggacga ugcggugugu uuguguguug uguuuguuau uccuguuugu guccucagac    60
gacucgcccg a                                                         71

<210> SEQ ID NO 170
<211> LENGTH: 72
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(72)
<223> OTHER INFORMATION: All pyrimidines are 2'F.

<400> SEQUENCE: 170
gggaggacga ugcggucggu cguaaaaaau cguuggaguc uaucuauugu ucucccaga    60 cgacucgccc ga                                                        72

<210> SEQ ID NO 171
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(70)
<223> OTHER INFORMATION: All pyrimidines are 2'F.

<400> SEQUENCE: 171
gggaggacga ugcggugcuc cagaggaacc aucguuuacu ucauuuauuc gccccagacg    60
acucgcccga                                                           70

<210> SEQ ID NO 172
<211> LENGTH: 72
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(72)
<223> OTHER INFORMATION: All pyrimidines are 2'F.

<400> SEQUENCE: 172
gggaggacga ugcggugcuc cuuaggaacc aucgucuaua ucccauucug acugcccaga    60
cgacucgccc ga                                                        72

<210> SEQ ID NO 173

<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(71)
<223> OTHER INFORMATION: All pyrimidines are 2'F.

<400> SEQUENCE: 173
gggaggacga ugcggugcuc cucaggaacc aucguuuuuc ccauguccuu cugcccagac    60
gacucgcccg a    71

<210> SEQ ID NO 174
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(71)
<223> OTHER INFORMATION: All pyrimidines are 2'F.

<400> SEQUENCE: 174
gggaggacga ugcggugcuc cuuggauuac caaggaacca uuuccucua cccccccagac    60 gacucgcccg a    71

<210> SEQ ID NO 175
<211> LENGTH: 76
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(76)
<223> OTHER INFORMATION: All pyrimidines are 2'F.

<400> SEQUENCE: 175
gggagauaag aauaaacgcu caagugcuca uuacgaacuu gaccgaugcc uauucgacag    60
gaggcucaca acaggc    76

<210> SEQ ID NO 176
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 176
gggagauaag aauaaacgcu caagugcuc auuacgaacu ugaccgaagc cuauucgaca    60
ggaggcucac aacaggc    77

<210> SEQ ID NO 177
<211> LENGTH: 77
<212> TYPE: RNA
<213> ORGANISM: Artificial Sequence

```
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 177
gggagauaag aauaaacgcu caaggugcuc auuacgaacu ugaccgaugc cuauucgaca        60
ggaggcucac aacaggc                                                      77

<210> SEQ ID NO 178
<211> LENGTH: 74
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(74)
<223> OTHER INFORMATION: All pyrimidines are 2'F.

<400> SEQUENCE: 178
gggagauaag aauaaacgcu caaagugcuc caaugaacuu ugcucgcuga uucgacagga        60
ggcucacaac aggc                                                         74

<210> SEQ ID NO 179
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 179
gggagauaag aauaaacgcu caaggugcuc cguuuggaac uugaucggua ggauucgaca        60
ggaggcucac aacaggc                                                      77

<210> SEQ ID NO 180
<211> LENGTH: 76
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(76)
<223> OTHER INFORMATION: All pyrimidines are 2'F.

<400> SEQUENCE: 180
gggagauaag aauaaacgcu caagugcuca uucagaacuu gacguauaac cauucgacag        60
gaggcucaca acaggc                                                       76

<210> SEQ ID NO 181
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
```

```
<220> FEATURE:
<221> NAME/KEY: modified_base
<222> LOCATION: (1)..(77)
<223> OTHER INFORMATION: All pyrimidines are 2'F.

<400> SEQUENCE: 181
gggagauaag aauaaacgcu caaggugcuc cuuaggaacu ugaccguccg ccauucgaca      60
ggaggcucac aacaggc                                                    77

<210> SEQ ID NO 182
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 182
gggagauaag aauaaacgcu caagugguge uccacuaacc aaguggaacc uuguucgaca      60
ggaggcucac aacaggc                                                    77

<210> SEQ ID NO 183
<211> LENGTH: 66
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(66)
<223> OTHER INFORMATION: All pyrimidines are 2'F.

<400> SEQUENCE: 183
gggagauaag aauaaacgcu caagugcucu ugaacuugac cguucgacag gaggcucaca      60
acaggc                                                                66

<210> SEQ ID NO 184
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
<223> OTHER INFORMATION: All pyrimidines are 2'F.

<400> SEQUENCE: 184
gggagauaag aauaaacgcu caaacgauaa gugggaguga guaaguuuga guauucgaca      60
ggaggcucac aacaggc                                                    77

<210> SEQ ID NO 185
<211> LENGTH: 77
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(77)
```

<223> OTHER INFORMATION: All pyrimidines are 2'F.

<400> SEQUENCE: 185
gggagauaag aauaaacgcu caaccuagac ccccagguuc cucccacua gucuucgaca    60 ggaggcucac aacaggc    77

<210> SEQ ID NO 186
<211> LENGTH: 36
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(36)
<223> OTHER INFORMATION: All pyrimidines are 2'F.  Purines at
      positions 1, 2, 6, 8, 11, 13-15, 17, 21, 27, 30, 33 are 2'OMe.

<400> SEQUENCE: 186
ggacgaugcg gcgagugccu guuuauguca ucgucc    36

<210> SEQ ID NO 187
<211> LENGTH: 36
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(36)
<223> OTHER INFORMATION: All pyrimidines are 2'F.  Purines at 1-3, 6, 8,
      10-11, 13-15, 17, 21, 27, 30, 33 are 2'OMe.

<400> SEQUENCE: 187
ggacgaugcg gcgagugccu guuuauguca ucgucc    36

<210> SEQ ID NO 188
<211> LENGTH: 39
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 188
acgagtttat cgaaaagaa cgatggttcc aatggagca    39

<210> SEQ ID NO 189
<211> LENGTH: 27
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 189
cgcaggatcc taatacgact cactata    27

<210> SEQ ID NO 190
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<220> FEATURE:

```
<221> NAME/KEY: modified_base
<222> LOCATION: (1)..(71)
<223> OTHER INFORMATION: All pyrimidines are 2'F.

<400> SEQUENCE: 190
gggaggacga ugcggnnnnn nnnnnnnnnn nnnnnnnnnn nnnnnnnnnn nnnnncagac    60
gacucgcccg a                                                         71

<210> SEQ ID NO 191
<211> LENGTH: 104
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 191
taatacgact cactataggg agacaagaat aaacgctcaa nnnnnnnnnn nnnnnnnnnn    60
nnnnnnnnnn nnnnnnnnnn ttcgacagga ggctcacaac aggc                    104

<210> SEQ ID NO 192
<211> LENGTH: 87
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(87)
<223> OTHER INFORMATION: All pyrimidines are 2'F.

<400> SEQUENCE: 192
gggagauaag aauaaacgcu caannnnnnn nnnnnnnnnn nnnnnnnnnn nnnnnnnnnn    60
nnnuucgaca ggaggcucac aacaggc                                        87
```